(12) United States Patent
Rodriguez-Navarro et al.

(10) Patent No.: US 10,905,511 B2
(45) Date of Patent: Feb. 2, 2021

(54) GRASPER WITH MAGNETICALLY-CONTROLLED POSITIONING

(71) Applicant: Levita Magnetics International Corp., San Mateo, CA (US)

(72) Inventors: Alberto Rodriguez-Navarro, San Francisco, CA (US); Bryan Loomas, Los Gatos, CA (US)

(73) Assignee: LEVITA MAGNETICS INTERNATIONAL CORP., San Mateo, CA (US)

( * ) Notice: Subject to any disclaimer, the term of this patent is extended or adjusted under 35 U.S.C. 154(b) by 264 days.

(21) Appl. No.: 15/728,302

(22) Filed: Oct. 9, 2017

(65) Prior Publication Data

US 2018/0092703 A1  Apr. 5, 2018

Related U.S. Application Data

(63) Continuation of application No. PCT/US2016/027390, filed on Apr. 13, 2016.
(Continued)

(51) Int. Cl.
*A61B 17/29* (2006.01)
*A61B 17/02* (2006.01)
(Continued)

(52) U.S. Cl.
CPC ......... *A61B 34/73* (2016.02); *A61B 17/0218* (2013.01); *A61B 17/29* (2013.01);
(Continued)

(58) Field of Classification Search
CPC ............ A61B 17/0218; A61B 17/0281; A61B 17/128–1285; A61B 17/29; A61B 34/73; A61B 2034/00283; A61B 2034/00876
See application file for complete search history.

(56) References Cited

U.S. PATENT DOCUMENTS 2,678,228 A    5/1954  Gerhardt
2,863,444 A   12/1958  Winsten
(Continued)

FOREIGN PATENT DOCUMENTS

CA    2 748 471 A1    7/2010
CA      2733465 A1    9/2011
(Continued)

OTHER PUBLICATIONS

Extended European Search Report dated Oct. 30, 2018, for EP Application No. 16 780 691.8, filed on Apr. 13, 2016, 6 pages.
(Continued)

*Primary Examiner* — Thaddeus B Cox
(74) *Attorney, Agent, or Firm* — Cooley LLP

(57) ABSTRACT

Devices, systems, and methods for providing remote traction to tissue may include a grasper and a control element. The grasper may have a first jaw, a second jaw, a main body, and a first magnetic element. The control element may include a second magnetic element. The first and second magnetic elements may attract the grasper to the control element such that the grasper is oriented parallel, perpendicularly, or at an angle between parallel and perpendicular with respect to the control element and/or a body. In some instances, the grasper may include first and second magnetic elements and the control element may include third and fourth magnetic elements.

19 Claims, 36 Drawing Sheets

Related U.S. Application Data

(60) Provisional application No. 62/276,752, filed on Jan. 8, 2016, provisional application No. 62/146,922, filed on Apr. 13, 2015.

(51) Int. Cl.
  *A61B 34/00* (2016.01)
  *A61B 90/00* (2016.01)
  *A61B 17/00* (2006.01)

(52) U.S. Cl.
  CPC .. *A61B 90/361* (2016.02); *A61B 2017/00283* (2013.01); *A61B 2017/00473* (2013.01); *A61B 2017/00477* (2013.01); *A61B 2017/00876* (2013.01); *A61B 2017/2902* (2013.01); *A61B 2017/2931* (2013.01); *A61B 2017/2933* (2013.01); *A61B 2017/2934* (2013.01)

(56) References Cited

U.S. PATENT DOCUMENTS

| | | |
|---|---|---|
| 3,146,381 A | 8/1964 | Louis |
| 3,674,014 A | 7/1972 | Tillander |
| 3,789,285 A | 1/1974 | Nishizawa |
| 3,794,091 A | 2/1974 | Ersek et al. |
| 4,364,377 A | 12/1982 | Smith |
| 4,380,999 A | 4/1983 | Healy |
| 4,756,312 A | 7/1988 | Epley |
| 4,901,405 A | 2/1990 | Grover et al. |
| 4,915,435 A | 4/1990 | Levine |
| 4,971,067 A | 11/1990 | Bolduc et al. |
| 4,976,723 A | 12/1990 | Schad |
| 5,002,557 A | 3/1991 | Hasson |
| 5,156,608 A | 10/1992 | Troidl et al. |
| 5,282,806 A | 2/1994 | Haber et al. |
| 5,304,183 A | 4/1994 | Gourlay et al. |
| 5,304,185 A | 4/1994 | Taylor |
| 5,307,805 A | 5/1994 | Byrne |
| 5,415,160 A | 5/1995 | Ortiz et al. |
| 5,417,701 A | 5/1995 | Holmes |
| 5,449,361 A | 9/1995 | Preissman |
| 5,449,365 A | 9/1995 | Green et al. |
| 5,450,842 A | 9/1995 | Tovey et al. |
| 5,458,603 A | 10/1995 | Futch, Sr. |
| 5,458,693 A | 10/1995 | Codorniu |
| 5,465,711 A | 11/1995 | Moll et al. |
| 5,496,317 A | 3/1996 | Goble et al. |
| 5,499,986 A | 3/1996 | Dimarco |
| 5,529,568 A | 6/1996 | Rayman |
| 5,538,098 A | 7/1996 | Sparhawk |
| 5,593,379 A | 1/1997 | Rayman |
| 5,595,562 A | 1/1997 | Grier |
| 5,654,864 A | 8/1997 | Ritter et al. |
| 5,665,100 A | 9/1997 | Yoon |
| 5,681,260 A | 10/1997 | Ueda et al. |
| 5,728,121 A | 3/1998 | Bimbo et al. |
| 5,733,292 A | 3/1998 | Gustilo et al. |
| 5,749,881 A | 5/1998 | Sackier et al. |
| 5,766,189 A | 6/1998 | Matsuno |
| 5,782,748 A | 7/1998 | Palmer et al. |
| 5,797,911 A | 8/1998 | Sherman et al. |
| 5,797,939 A | 8/1998 | Yoon |
| 5,848,969 A | 12/1998 | Panescu et al. |
| 5,849,015 A | 12/1998 | Haywood et al. |
| 5,888,196 A | 3/1999 | Bonutti |
| 5,893,873 A | 4/1999 | Rader et al. |
| 5,933,926 A | 8/1999 | Reiter |
| 6,015,414 A | 1/2000 | Werp et al. |
| 6,099,537 A | 8/2000 | Sugai et al. |
| 6,099,550 A | 8/2000 | Yoon |
| 6,123,657 A | 9/2000 | Ishikawa et al. |
| 6,126,647 A | 10/2000 | Posey et al. |
| 6,127,757 A | 10/2000 | Swinbanks |
| 6,165,180 A | 12/2000 | Cigaina et al. |
| 6,173,715 B1 | 1/2001 | Sinanan et al. |
| 6,212,419 B1 | 4/2001 | Blume et al. |
| 6,216,028 B1 | 4/2001 | Haynor et al. |
| 6,241,671 B1 | 6/2001 | Ritter et al. |
| 6,311,082 B1 | 10/2001 | Creighton, IV et al. |
| 6,315,709 B1 | 11/2001 | Garibaldi et al. |
| 6,330,467 B1 | 12/2001 | Creighton, IV et al. |
| 6,340,365 B2 | 1/2002 | Dittrich et al. |
| 6,358,196 B1 | 3/2002 | Rayman |
| 6,371,973 B1 | 4/2002 | Tepper |
| 6,398,791 B1 | 6/2002 | Que et al. |
| 6,399,146 B1 | 6/2002 | Harris et al. |
| 6,401,723 B1 | 6/2002 | Garibaldi et al. |
| 6,440,133 B1 | 8/2002 | Beale et al. |
| 6,459,924 B1 | 10/2002 | Creighton, IV et al. |
| 6,464,710 B1 | 10/2002 | Foster |
| 6,488,615 B1 | 12/2002 | Mitchiner et al. |
| 6,523,919 B1 | 2/2003 | Israelsen et al. |
| 6,537,196 B1 | 3/2003 | Creighton, IV et al. |
| 6,551,304 B1 | 4/2003 | Whalen et al. |
| 6,594,517 B1 | 7/2003 | Nevo |
| 6,630,879 B1 | 10/2003 | Creighton, IV et al. |
| 6,656,199 B1 | 12/2003 | Lafontaine |
| 6,677,752 B1 | 1/2004 | Creighton, IV et al. |
| 6,689,119 B1 | 2/2004 | Di Caprio et al. |
| 6,702,804 B1 | 3/2004 | Ritter et al. |
| 6,705,989 B2 | 3/2004 | Cuschieri et al. |
| 6,719,765 B2 | 4/2004 | Bonutti |
| 6,761,681 B2 | 7/2004 | Schmid et al. |
| 6,786,219 B2 | 9/2004 | Garibaldi et al. |
| 6,817,364 B2 | 11/2004 | Garibaldi et al. |
| 6,824,511 B1 | 11/2004 | Bell et al. |
| 6,916,314 B2 | 7/2005 | Schneider et al. |
| 7,017,584 B2 | 3/2006 | Garibaldi et al. |
| 7,094,245 B2 | 8/2006 | Adams et al. |
| 7,169,104 B2 | 1/2007 | Ueda et al. |
| 7,182,089 B2 | 2/2007 | Ries |
| 7,182,775 B2 | 2/2007 | De Guillebon et al. |
| 7,189,198 B2 | 3/2007 | Harburn et al. |
| 7,264,584 B2 | 9/2007 | Ritter et al. |
| 7,311,107 B2 | 12/2007 | Harel et al. |
| 7,313,429 B2 | 12/2007 | Creighton, IV et al. |
| 7,341,063 B2 | 3/2008 | Garbibaldi et al. |
| 7,344,553 B2 | 3/2008 | Opolski et al. |
| 7,390,298 B2 | 6/2008 | Chu |
| 7,416,335 B2 | 8/2008 | Munger |
| 7,429,259 B2 | 9/2008 | Cadeddu et al. |
| 7,431,726 B2 | 10/2008 | Spence et al. |
| 7,566,038 B2 | 7/2009 | Scott et al. |
| 7,618,435 B2 | 11/2009 | Opolski |
| 7,686,827 B2 | 3/2010 | Hushka |
| 7,691,103 B2 | 4/2010 | Fernandez et al. |
| 7,691,731 B2 | 4/2010 | Bet et al. |
| 7,708,756 B2 | 5/2010 | Nobis et al. |
| 7,736,356 B2 | 6/2010 | Cooper et al. |
| 7,766,810 B2 | 8/2010 | Ohdaira |
| 7,769,427 B2 | 8/2010 | Shachar |
| 7,772,950 B2 | 8/2010 | Tunay |
| 7,774,046 B2 | 8/2010 | Werp et al. |
| 7,780,054 B2 | 8/2010 | Wales |
| 7,799,050 B2 | 9/2010 | Hensley et al. |
| 7,837,612 B2 | 11/2010 | Gill et al. |
| 7,850,591 B2 | 12/2010 | Spector |
| 7,963,903 B2 | 6/2011 | Ghiron et al. |
| 7,966,059 B2 | 6/2011 | Creighton, IV et al. |
| 7,967,830 B2 | 6/2011 | Ayala et al. |
| 8,038,612 B2 | 10/2011 | Paz |
| 8,043,290 B2 | 10/2011 | Harrison et al. |
| 8,057,472 B2 | 11/2011 | Walker et al. |
| 8,060,184 B2 | 11/2011 | Hastings et al. |
| 8,066,715 B2 | 11/2011 | Ducharme |
| 8,074,657 B2 | 12/2011 | Scott et al. |
| 8,082,035 B2 | 12/2011 | Glukhovsky |
| 8,133,254 B2 | 3/2012 | Dumbauld et al. |
| 8,136,888 B2 | 3/2012 | Suzuki et al. |
| 8,137,268 B2 | 3/2012 | Van Lue |
| 8,157,149 B2 | 4/2012 | Olson et al. |
| 8,187,286 B2 | 5/2012 | Jugenheimer et al. |
| 8,197,494 B2 | 6/2012 | Jaggi et al. |
| 8,235,272 B2 | 8/2012 | Nicholas et al. |

(56) References Cited

U.S. PATENT DOCUMENTS

| | | |
|---|---|---|
| 8,241,322 B2 | 8/2012 | Whitman et al. |
| 8,246,529 B2 | 8/2012 | Riehl et al. |
| 8,252,021 B2 | 8/2012 | Boulnois et al. |
| 8,267,854 B2 | 9/2012 | Asada et al. |
| 8,301,226 B2 | 10/2012 | Csavoy et al. |
| 8,303,495 B2 | 11/2012 | Ducharme |
| 8,313,497 B2 | 11/2012 | Walberg et al. |
| 8,316,861 B2 | 11/2012 | Brewer et al. |
| 8,316,862 B2 | 11/2012 | Shapiro et al. |
| 8,333,695 B2 | 12/2012 | Cuschieri |
| 8,360,972 B2 | 1/2013 | Paz |
| 8,364,277 B2 | 1/2013 | Glukhovsky |
| 8,377,044 B2 | 2/2013 | Coe et al. |
| 8,382,754 B2 | 2/2013 | Odom et al. |
| 8,480,668 B2 | 7/2013 | Fernandez et al. |
| 8,491,626 B2 | 7/2013 | Roy et al. |
| 8,517,931 B2 | 8/2013 | Minnelli et al. |
| 8,518,057 B2 | 8/2013 | Walberg et al. |
| 8,556,919 B2 | 10/2013 | Aguirre et al. |
| 8,579,787 B2 | 11/2013 | Shapiro et al. |
| 8,585,685 B2 | 11/2013 | Hagg |
| 8,602,981 B2 | 12/2013 | Deutch |
| 8,608,773 B2 | 12/2013 | Tierney et al. |
| 8,623,011 B2 | 1/2014 | Spivey |
| 8,628,529 B2 | 1/2014 | Aldridge et al. |
| 8,636,762 B2 | 1/2014 | Whitman et al. |
| 8,637,818 B2 | 1/2014 | Balakin |
| 8,685,043 B2 | 4/2014 | Jugenheimer et al. |
| 8,758,394 B2 | 6/2014 | Zimmerling et al. |
| 8,764,769 B1 | 7/2014 | Rodriguez-Navarro et al. |
| 8,790,245 B2 | 7/2014 | Rodriguez Fernandez et al. |
| 8,820,602 B2 | 9/2014 | Walberg et al. |
| 8,827,891 B2 | 9/2014 | Roberts |
| 8,828,024 B2 | 9/2014 | Farritor et al. |
| 8,894,574 B2 | 11/2014 | Ellman |
| 8,926,656 B2 | 1/2015 | Palermo et al. |
| 8,944,997 B2 | 2/2015 | Fernandez et al. |
| 8,968,332 B2 | 3/2015 | Farritor et al. |
| 8,968,356 B2 | 3/2015 | Mueller |
| 9,011,468 B2 | 4/2015 | Ketai et al. |
| 9,033,957 B2 | 5/2015 | Cadeddu et al. |
| 9,044,256 B2 | 6/2015 | Cadeddu et al. |
| 9,339,285 B2 | 5/2016 | Rodriguez-Navarro et al. |
| 9,386,973 B2 | 7/2016 | Deutch |
| 9,844,391 B2 | 12/2017 | Rodriguez Fernandez et al. |
| 9,962,148 B2 | 5/2018 | Deutch |
| 9,974,546 B2 | 5/2018 | Rodriguez Fernandez et al. |
| 10,010,370 B2 | 7/2018 | Rodriguez-Navarro et al. |
| 10,130,381 B2 | 11/2018 | Rodriguez-Navarro et al. |
| 10,537,348 B2 | 1/2020 | Rodriguez-Navarro et al. |
| 2001/0038683 A1 | 11/2001 | Ritter et al. |
| 2002/0100486 A1 | 8/2002 | Creighton, IV et al. |
| 2002/0107533 A1 | 8/2002 | Solingen |
| 2002/0116043 A1 | 8/2002 | Garibaldi et al. |
| 2002/0173805 A1 | 11/2002 | Matsuno et al. |
| 2003/0114731 A1 | 6/2003 | Cadeddu et al. |
| 2003/0125752 A1 | 7/2003 | Werp et al. |
| 2003/0208185 A1 | 11/2003 | Sheffer et al. |
| 2004/0050395 A1 | 3/2004 | Ueda et al. |
| 2004/0064153 A1 | 4/2004 | Creighton, IV et al. |
| 2004/0068173 A1 | 4/2004 | Viswanathan |
| 2004/0158972 A1 | 8/2004 | Creighton, IV et al. |
| 2004/0172057 A1 | 9/2004 | Guillebon et al. |
| 2004/0199074 A1 | 10/2004 | Ritter et al. |
| 2004/0230100 A1 | 11/2004 | Shluzas |
| 2004/0249262 A1 | 12/2004 | Werp et al. |
| 2005/0080440 A1 | 4/2005 | Durgin et al. |
| 2005/0113628 A1 | 5/2005 | Creighton, IV et al. |
| 2005/0131390 A1 | 6/2005 | Heinrich et al. |
| 2005/0165449 A1 | 7/2005 | Cadeddu et al. |
| 2005/0220583 A1 | 10/2005 | Lutz |
| 2005/0250988 A1 | 11/2005 | Ewers et al. |
| 2005/0277975 A1 | 12/2005 | Saadat et al. |
| 2006/0015178 A1 | 1/2006 | Moaddeb et al. |
| 2006/0074448 A1 | 4/2006 | Harrison et al. |
| 2006/0079897 A1 | 4/2006 | Harrison et al. |
| 2006/0089633 A1 | 4/2006 | L. Bleich et al. |
| 2006/0149135 A1 | 7/2006 | Paz |
| 2006/0152309 A1 | 7/2006 | Mintchev et al. |
| 2006/0228421 A1 | 10/2006 | Seeney et al. |
| 2006/0241691 A1 | 10/2006 | Wilk |
| 2006/0247522 A1 | 11/2006 | Mcgee |
| 2006/0293566 A1 | 12/2006 | Brown |
| 2007/0004958 A1 | 1/2007 | Ohdaira |
| 2007/0016010 A1 | 1/2007 | Creighton, IV et al. |
| 2007/0027458 A1 | 2/2007 | Sixto, Jr. et al. |
| 2007/0043359 A1 | 2/2007 | Altarac et al. |
| 2007/0073102 A1 | 3/2007 | Matsuno et al. |
| 2007/0135678 A1 | 6/2007 | Suzuki |
| 2007/0135685 A1 | 6/2007 | Cuschieri |
| 2007/0135802 A1 | 6/2007 | Suzuki |
| 2007/0135803 A1 | 6/2007 | Belson |
| 2007/0156028 A1 | 7/2007 | Van Lue et al. |
| 2007/0191670 A1 | 8/2007 | Spector |
| 2007/0255273 A1 | 11/2007 | Fernandez et al. |
| 2007/0270629 A1 | 11/2007 | Charles |
| 2007/0282311 A1 | 12/2007 | Scott et al. |
| 2008/0081883 A1 | 4/2008 | King et al. |
| 2008/0097496 A1 | 4/2008 | Chang et al. |
| 2008/0108860 A1 | 5/2008 | Bell et al. |
| 2008/0134474 A1 | 6/2008 | Uryasov |
| 2008/0171907 A1 | 7/2008 | Long et al. |
| 2008/0243106 A1 | 10/2008 | Coe et al. |
| 2008/0249534 A1 | 10/2008 | Gruber et al. |
| 2008/0269779 A1 | 10/2008 | Cadeddu et al. |
| 2008/0300458 A1* | 12/2008 | Kim .................. A61B 1/00158 600/118 |
| 2009/0005636 A1 | 1/2009 | Pang et al. |
| 2009/0043246 A1 | 2/2009 | Dominguez |
| 2009/0054909 A1 | 2/2009 | Farritor et al. |
| 2009/0062772 A1 | 3/2009 | Wakeford et al. |
| 2009/0076536 A1 | 3/2009 | Rentschler et al. |
| 2009/0137984 A1 | 5/2009 | Minnelli |
| 2009/0187074 A1 | 7/2009 | Saadat et al. |
| 2009/0192344 A1 | 7/2009 | Bakos et al. |
| 2009/0267717 A1 | 10/2009 | Baskett |
| 2010/0030026 A1 | 2/2010 | Uchiyama et al. |
| 2010/0036394 A1 | 2/2010 | Mintz et al. |
| 2010/0036399 A1 | 2/2010 | Viola |
| 2010/0081876 A1 | 4/2010 | Linenkugel et al. |
| 2010/0105984 A1 | 4/2010 | Brewer et al. |
| 2010/0113872 A1 | 5/2010 | Asada et al. |
| 2010/0114126 A1 | 5/2010 | Neff |
| 2010/0145147 A1 | 6/2010 | Pinsky et al. |
| 2010/0152539 A1 | 6/2010 | Ghabrial et al. |
| 2010/0160739 A1 | 6/2010 | Van Lue |
| 2010/0168523 A1 | 7/2010 | Ducharme |
| 2010/0174234 A1 | 7/2010 | Werp et al. |
| 2010/0193566 A1 | 8/2010 | Scheib et al. |
| 2010/0204727 A1 | 8/2010 | Dominguez |
| 2010/0217245 A1 | 8/2010 | Prescott |
| 2010/0237206 A1 | 9/2010 | Barker |
| 2010/0256636 A1 | 10/2010 | Fernandez et al. |
| 2010/0268254 A1 | 10/2010 | Golden et al. |
| 2010/0298645 A1 | 11/2010 | Deutch |
| 2011/0040152 A1 | 2/2011 | Kim et al. |
| 2011/0054306 A1 | 3/2011 | Del Nido et al. |
| 2011/0087223 A1 | 4/2011 | Spivey |
| 2011/0087224 A1 | 4/2011 | Cadeddu et al. |
| 2011/0087249 A1 | 4/2011 | Rodrigues et al. |
| 2011/0105848 A1 | 5/2011 | Sadovsky et al. |
| 2011/0121050 A1 | 5/2011 | Nicholas et al. |
| 2011/0130787 A1 | 6/2011 | Cinquin et al. |
| 2011/0184440 A1 | 7/2011 | Saldinger |
| 2011/0230726 A1 | 9/2011 | Viola |
| 2011/0276941 A1 | 11/2011 | Oi |
| 2011/0283822 A1 | 11/2011 | Cadeddu et al. |
| 2011/0284014 A1 | 11/2011 | Cadeddu et al. |
| 2011/0285488 A1 | 11/2011 | Scott et al. |
| 2011/0295067 A1 | 12/2011 | Rodriguez Fernandez et al. |
| 2011/0306840 A1 | 12/2011 | Allen et al. |
| 2011/0313415 A1 | 12/2011 | Fernandez et al. |
| 2012/0016362 A1 | 1/2012 | Heinrich et al. |
| 2012/0035416 A1 | 2/2012 | Fernandez et al. |

(56) References Cited

U.S. PATENT DOCUMENTS

| | | |
|---|---|---|
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078292 A1 | 3/2012 | Banju |
| 2012/0085358 A1 | 4/2012 | Cadeddu et al. |
| 2012/0101488 A1 | 4/2012 | Aldridge et al. |
| 2012/0116148 A1 | 5/2012 | Weinberg et al. |
| 2012/0227748 A1 | 9/2012 | Sanders |
| 2012/0238796 A1 | 9/2012 | Conlon |
| 2012/0330089 A1 | 12/2012 | Ritter et al. |
| 2013/0030462 A1 | 1/2013 | Keating et al. |
| 2013/0066304 A1 | 3/2013 | Belson et al. |
| 2013/0085341 A1 | 4/2013 | Nobis et al. |
| 2013/0090666 A1 | 4/2013 | Hess et al. |
| 2013/0109267 A1 | 5/2013 | Schweikardt et al. |
| 2013/0110128 A1 | 5/2013 | Schostek et al. |
| 2013/0123828 A1 | 5/2013 | Culmer et al. |
| 2013/0158348 A1 | 6/2013 | Nobis et al. |
| 2013/0158523 A1 | 6/2013 | Bergs et al. |
| 2013/0158659 A1 | 6/2013 | Bergs et al. |
| 2013/0158660 A1 | 6/2013 | Bergs et al. |
| 2013/0226226 A1 | 8/2013 | Garrison et al. |
| 2013/0245356 A1 | 9/2013 | Fernandez et al. |
| 2013/0253256 A1 | 9/2013 | Griffith et al. |
| 2013/0253275 A1 | 9/2013 | Ransden et al. |
| 2013/0253550 A1 | 9/2013 | Beisel et al. |
| 2013/0267788 A1* | 10/2013 | Duan ................. B25J 11/00 600/300 |
| 2013/0289579 A1 | 10/2013 | Yeung et al. |
| 2013/0289768 A1 | 10/2013 | Yeung et al. |
| 2013/0303851 A1 | 11/2013 | Griffith et al. |
| 2014/0066695 A1 | 3/2014 | Deutch |
| 2014/0084761 A1 | 3/2014 | Scott et al. |
| 2014/0135616 A1 | 5/2014 | Stein et al. |
| 2014/0243586 A1 | 8/2014 | Rohaninejad et al. |
| 2014/0243597 A1 | 8/2014 | Weisenburgh, II et al. |
| 2014/0257370 A1 | 9/2014 | Taylor et al. |
| 2014/0276335 A1 | 9/2014 | Pate |
| 2014/0277104 A1 | 9/2014 | Rodriguez-Navarro et al. |
| 2014/0350574 A1 | 11/2014 | Farritor et al. |
| 2014/0358229 A1 | 12/2014 | Bergs et al. |
| 2016/0038135 A1 | 2/2016 | Deutch |
| 2016/0120613 A1 | 5/2016 | Cadeddu et al. |
| 2016/0228138 A1 | 8/2016 | Rodriguez-Navarro et al. |
| 2016/0302811 A1 | 10/2016 | Rodriguez-Navarro et al. |
| 2018/0153633 A1 | 6/2018 | Rodriguez-Navarro et al. |
| 2018/0271550 A1 | 9/2018 | Rodriguez-Navarro |
| 2018/0296289 A1 | 10/2018 | Rodriguez-Navarro et al. |
| 2019/0133631 A1 | 5/2019 | Rodriguez-Navarro et al. |

FOREIGN PATENT DOCUMENTS

| | | |
|---|---|---|
| CN | 2244381 Y | 1/1997 |
| CN | 101090672 A | 12/2007 |
| CN | 201079412 Y | 7/2008 |
| CN | 201091596 Y | 7/2008 |
| CN | 101534725 A | 9/2009 |
| CN | 102068288 A | 5/2011 |
| CN | 102355865 A | 2/2012 |
| CN | 203953720 U | 11/2014 |
| DE | 42 12 430 A1 | 10/1993 |
| DE | 19534618 A1 | 3/1997 |
| DE | 10 2005 006 705 A1 | 8/2006 |
| DE | 10-2010-010417 A1 | 9/2011 |
| EP | 1 797 823 A1 | 6/2007 |
| EP | 1 972 284 A2 | 9/2008 |
| EP | 2 012 697 A2 | 1/2009 |
| EP | 2 355 699 A2 | 8/2011 |
| EP | 2 366 357 A1 | 9/2011 |
| EP | 2 381 873 A2 | 11/2011 |
| EP | 2 391 277 | 12/2011 |
| EP | 1 942 810 B1 | 8/2012 |
| EP | 2 571 443 A2 | 3/2013 |
| EP | 2 595 548 | 5/2013 |
| EP | 2 842 511 A1 | 3/2015 |
| JP | 09-192137 A | 7/1997 |
| JP | 2004-357816 A | 12/2004 |
| JP | 2005-021576 A | 1/2005 |
| JP | 4320214 B2 | 8/2009 |
| JP | 2009-538699 A | 11/2009 |
| WO | WO-2005/004734 A1 | 1/2005 |
| WO | WO-2006/071120 A1 | 7/2006 |
| WO | WO-2007/130382 A2 | 11/2007 |
| WO | WO-2007/130382 A3 | 11/2007 |
| WO | WO-2007/142977 A2 | 12/2007 |
| WO | WO-2007/142977 A3 | 12/2007 |
| WO | WO-2007/143162 A2 | 12/2007 |
| WO | WO-2007/143162 A3 | 12/2007 |
| WO | WO-2007/143170 A2 | 12/2007 |
| WO | WO-2007/143170 A3 | 12/2007 |
| WO | WO-2008/039237 A1 | 4/2008 |
| WO | WO-2008/085919 A2 | 7/2008 |
| WO | WO-2008/085919 A3 | 7/2008 |
| WO | WO-2008/131126 A1 | 10/2008 |
| WO | WO-2009/008865 A1 | 1/2009 |
| WO | WO-2009/019288 A2 | 2/2009 |
| WO | WO-2009/019288 A3 | 2/2009 |
| WO | WO-2009/070743 A1 | 6/2009 |
| WO | WO-2010/056716 A2 | 5/2010 |
| WO | WO-2010/056716 A3 | 5/2010 |
| WO | WO-2010/077561 A1 | 7/2010 |
| WO | WO-2010/083480 A2 | 7/2010 |
| WO | WO-2010/083480 A3 | 7/2010 |
| WO | WO-2010/089635 A1 | 8/2010 |
| WO | WO-2011/044468 A2 | 4/2011 |
| WO | WO-2011/044468 A3 | 4/2011 |
| WO | WO-2011/044471 A2 | 4/2011 |
| WO | WO-2011/044471 A3 | 4/2011 |
| WO | WO-2011/091483 A1 | 8/2011 |
| WO | WO-2011/146691 A2 | 11/2011 |
| WO | WO-2011/146691 A3 | 11/2011 |
| WO | WO 2011/146698 A2 | 11/2011 |
| WO | WO 2011/146698 A3 | 11/2011 |
| WO | WO-2011/146709 A2 | 11/2011 |
| WO | WO-2011/146709 A3 | 11/2011 |
| WO | WO-2012/010910 A1 | 1/2012 |
| WO | WO-2012/031114 A2 | 3/2012 |
| WO | WO-2012/031114 A3 | 3/2012 |
| WO | WO-2012/033925 A1 | 3/2012 |
| WO | WO-2012/048102 A2 | 4/2012 |
| WO | WO-2012/048102 A3 | 4/2012 |
| WO | WO-2013/096470 A1 | 6/2013 |
| WO | WO-2014/133751 A1 | 9/2014 |
| WO | WO-2014/159023 A1 | 10/2014 |
| WO | WO-2014/163872-AI | 10/2014 |
| WO | WO-2015/112645 A1 | 7/2015 |
| WO | WO-2016/168380 A1 | 10/2016 |

OTHER PUBLICATIONS

Extended European Search Report dated Nov. 26, 2018, for EP Application No. 16 780 688.4, filed on Sep. 26, 2017, 9 pages.

Extended European Search Report dated Aug. 22, 2019, for EP Application No. 17 736 483.3, filed on Jan. 6, 2017, 8 pages.

Final Office Action dated Feb. 26, 2019, for U.S. Appl. No. 15/195,898, filed on Jun. 28, 2016, 9 pages.

International Search Report dated Apr. 3, 2017, for PCT Application No. PCT/US2017/012628, filed on Jan. 6, 2017, 2 pages.

Non-Final Office Action dated Sep. 17, 2019, for U.S. Appl. No. 15/728,297, filed on Oct. 9, 2017, 8 pages.

Notice of Allowance dated Sep. 11, 2019, for U.S. Appl. No. 15/195,898, filed on Jun. 28, 2016, 9 pages.

Notice of Allowance dated Nov. 26, 2019, for U.S. Appl. No. 15/195,898, filed on Jun. 28, 2016, 6 pages.

Written Opinion of the International Searching Authority dated Apr. 3, 2017, for PCT Application No. PCT/US2017/012628, filed on Jan. 6, 2017, 7 pages.

Dominguez (2007). "Colecistectomia con un trocar asistida por imanes de neodimio. Reporte de un caso." *Asociacion Mexicana de Cirugia Endo.* vol. 8. No. 4, pp. 172-176 (with English Abstract).

(56) References Cited

OTHER PUBLICATIONS

Extended European Search Report dated Jul. 20, 2016, for EP Application No. 14 778 895.4, filed on Feb. 25, 2014, 7 pages.
Extended European Search Report dated Dec. 20, 2016, for EP Application No. 09 839 564.3, filed on Oct. 1, 2009, 11 pages.
Extended European Search Report dated Sep. 27, 2017, for EP Application No. 15 741 055.6, filed on Jan. 21, 2015, 9 pages.
Final Office Action dated Sep. 16, 2016, for U.S. Appl. No. 14/704,828, filed on May 5, 2015, 10 pages.
Final Office Action dated Jan. 25, 2016, for U.S. Appl. No. 14/337,082, filed on Jul. 21, 2014, 9 pages.
Final Office Action dated Dec. 28, 2016, for U.S. Appl. No. 14/200,302, filed on Mar. 7, 2014, 15 pages.
Final Office Action dated Sep. 6, 2017, for U.S. Appl. No. 14/200,302, filed on Mar. 7, 2014, 9 pages.
Final Office Action dated Mar. 7, 2018, for U.S. Appl. No. 15/098,262, filed on Apr. 13, 2016, 10 pages.
International Search Report dated Jul. 30, 2014, for PCT Application No. PCT/US2014/021537, filed on Mar. 7, 2014, 2 pages.
International Search Report for International Application No. PCT/IB2009/054307 dated Feb. 8, 2010, 4 pages.
International Search Report dated May 4, 2015, for PCT Application No. PCT/US2015/012319, filed on Jan. 21, 2015, 2 pages.
International Search Report dated Jul. 18, 2014, for PCT Application No. PCT/US2014/018307, filed on Feb. 25, 2014, 4 pages.
International Search Report dated Jul. 15, 2016, for PCT Application No. PCT/US2016/027385, filed on Apr. 13, 2016, 2 pages.
International Search Report dated Aug. 22, 2016, for PCT Application No. PCT/US2016/027390, filed on Apr. 13, 2016, 4 pages.
Non-Final Office Action dated May 25, 2016, for U.S. Appl. No. 14/200,302, filed on Mar. 7, 2014, 12 pages.
Non-Final Office Action dated May 21, 2013 for U.S. Appl. No. 13/132,185, filed on Aug. 17, 2011, 18 pages.
Non-Final Office Action dated Jul. 21, 2016, for U.S. Appl. No. 14/337,082, filed on Jul. 21, 2014, 9 pages.
Non-Final Office Action dated Jul. 13, 2015, for U.S. Appl. No. 14/337,082, filed on Jul. 21, 2014, 10 pages.
Non-Final Office Action dated Jan. 25, 2016, for U.S. Appl. No. 14/704,828, filed on May 5, 2015, 9 pages.
Non-Final Office Action dated Jul. 14, 2015, for U.S. Appl. No. 14/704,828, filed on May 5, 2015, 10 pages.
Non-Final Office Action dated Oct. 24, 2013, for U.S. Appl. No. 14/019,370, filed on Sep. 5, 2013, 7 pages.
Non-Final Office Action dated Oct. 22, 2015, for U.S. Appl. No. 14/019,404, filed on Sep. 5, 2013, 6 pages.
Non-Final Office Action dated May 22, 2017, for U.S. Appl. No. 14/200,302, filed on Mar. 7, 2014, 14 pages.
Non-Final Office Action dated May 3, 2017, for U.S. Appl. No. 14/704,828, filed on May 5, 2015, 8 pages.
Non-Final Office Action dated Jul. 24, 2017, for U.S. Appl. No. 15/098,262, filed on Apr. 13, 2016, 9 pages.
Non-Final Office Action dated Jun. 29, 2018, for U.S. Appl. No. 15/195,898, filed on Jun. 26, 2016, 9 pages.
Notice of Allowance dated Feb. 14, 2014, for U.S. Appl. No. 14/019,370, filed on Sep. 5, 2013, 7 pages.
Notice of Allowance dated Mar. 14, 2014, for U.S. Appl. No. 13/132,185, filed on Aug. 17, 2011, 7 pages.
Notice of Allowance dated Mar. 14, 2016, for U.S. Appl. No. 14/019,404, filed on Sep. 5, 2013, 7 pages.
Notice of Allowance dated May 3, 2017, for U.S. Appl. No. 14/337,082, filed on Jul. 21, 2014, 7 pages.
Notice of Allowance dated Aug. 25, 2017, for U.S. Appl. No. 14/337,082, filed on Jul. 21, 2014, 7 pages.
Notice of Allowance dated Nov. 22, 2017, for U.S. Appl. No. 14/200,302, filed on Mar. 7, 2014, 5 pages.
Notice of Allowance dated Jan. 19, 2018, for U.S. Appl. No. 14/704,828, filed on May 5, 2015, 7 pages.
Notice of Allowance dated Aug. 24, 2018, for U.S. Appl. No. 15/098,262, filed on Apr. 13, 2016, 9 pages.
Wikipedia (2015). "Stainless Steel," retrieved from https://en.wikipedia.org/wiki/Stainless_steel, 13 pages.
Written Opinion of the International Searching Authority dated Jul. 30, 2014, for PCT Application No. PCT/US2014/021537, filed on Mar. 7, 2014, 5 pages.
Written Opinion of the International Searching Authority for International Application No. PCT/IB2009/054307 dated Feb. 8, 2010.
Written Opinion of the International Searching Authority dated Jul. 18, 2014, for PCT Application No. PCT/US2014/018307, filed on Feb. 25, 2014, 5 pages.
Written Opinion of the International Searching Authority dated May 4, 2015, for PCT Application No. PCT/US2015/012319, filed on Jan. 21, 2015, 5 pages.
Written Opinion of the International Searching Authority dated Jul. 15, 2016, for PCT Application No. PCT/US2016/027385, filed on Apr. 13, 2016, 11 pages.
Written Opinion of the International Searching Authority dated Aug. 22, 2016, for PCT Application No. PCT/US2016/027390, filed on Apr. 13, 2016, 9 pages.
Best, S.L. et al. (2010). "Development of magnetic anchoring and guidance systems for minimally invasive surgery," Indian J. of Urology 26:418-422.
Best, S.L. et al. (2010). "Solo Surgeon Less Nephrectomy Facilitated by New Generation Magnetically Anchored and Guided (MAGS) Camera," World Congress of Endourology, PS38-14, Chicago IL, Sep. 2010.
Best, S.L. et al. (2010). "MAGS Instrumentation for Less/Notes: Lack of Histologic Damage After Prolonged Magnetic Coupling Across the Abdominal Wall," World Congress of Endourology, PS2-4, Chicago IL, Sep. 2010.
Best, S.L. et al. (2008). "Maximizing Coupling Strength of Magnetically Anchored Notes Instruments: How Thick Can We Go?" Surgical Endoscopy, vol. 22: S241.
Cadeddu, J.A. et al. (2002). "Transabdominal magnetic anchoring system for trocar-less laparoscopic surgery," J. of Urology, vol. 167, No. 4, Supplement, Abstract No. 16, 1 total page.
Cadeddu, J. et al. (2009). "Novel Magnetically Guided Intraabdominal Camera to Facilitate Laparoendoscopic Single Site Surgery: Initial Human Experience," Surgical Endoscopy 23:1894-1899.
Dominguez, G. et al. (2009). "Retraction and triangulation with neodymium magnetic forceps for single-port laparoscopic cholecystectomy," Surg. Endosc. 23:1660-1666.
Duchene, D.A. et al. (2004). "Magnetic positioning system for trocarless laparoscopic instruments," J. of Endourology 18:693.
Fernandez, R. et al. (2012). "Determining a Performance Envelope for Capture of Kidney Stones Functionalized with Superparamagnetic Particles," Journal of Endourology, 26(9):1227-30.
Fernandez, R. et al. (2003). "Development of a Transabdominal Anchoring System for Trocar-Less Laparoscopic Surgery," Advances in Bioengineering—ASME International Mechanical Engineering Congress & Exposition, Washington DC, Nov. 2003, BED vol. 55, pp. 157-158.
Leong, F. et al. (2016). "Magnetic surgical instruments for robotic abdominal surgery," IEEE Reviews in Biomedical Engineering 9:66-78.
Mashaud, L. et al. (2011). "Tissue Compression Analysis for Magnetically Anchored Cautery Dissector During Single Site Laparoscopic Cholecystectomy," Journal of Gastrointestinal Surgery 15:902-907.
Mashaud, L. et al. (2010). "Tissue Compression Analysis for Magnetically Anchored Cautery Dissector During Single Site Laparoscopic Cholecystectomy," Gastroenterology, 138:5 (Supplement 1):S-882.
Mashaud, L. et al. (2010). "Magnetic Cautery Dissector Suitability for Traditional or Single Site Laparoscopic Cholecystectomy in Human Cadaver Models," 12th World Congress of Endoscopic Surgery, P246, National Harbor, MD, Apr. 2010.
Non-Final Office Action dated Mar. 6, 2020, for U.S. Appl. No. 15/926,578, filed on Mar. 20, 2018, 9 pages.
Park, S. et al. (2007). "Trocar-less instrumentation for laparoscopy magnetic positioning of intra-abdominal camera and retractor," Surgical Technique 245:379-384.

(56) References Cited

OTHER PUBLICATIONS

Raman, J. (2009). "Complete Transvaginal Notes Nephrectomy Using Magnetically Anchored Instrumentation," Journal of Endourology 23:367-371.

Rivas, H. et al. (2005). "A Magnetic Positioning System to Drive Trocarless Laparoscopic Instruments," First International Minimally Invasive Robotic Association (MIRA) Conference on Robotic Surgery, Innsbruck, Austria, Dec. 2005.

Scott, D.J. et al. (2007). "Completely transvaginal Notes cholecystectomy using magnetically anchored instruments," Surg. Endosc. 21:2308-2316.

Scott, D. et al. (2008). "Optimizing Magnetically Anchored Camera, Light Source, Graspers, and Cautery Dissector for Transvaginal Notes Cholecystectomy," Surgical Endoscopy 22:S244.

Scott, D. et al. (2008). "Randomized Comparison of Laparoscopic, Flexible Endoscopic, and Wired and Wireless Magnetic Notes Cameras on Ex-Vivo and In-Vivo Surgical Performance," Gastrointestinal Endoscopy, vol. 67: AB115.

Scott, D. et al. (2008). "Transvaginal Single Access "Pure" Notes Sleeve Gastrectomy Using a Deployable Magnetically Anchored Video Camera," Gastrointestinal Endoscopy, vol. 67: AB116.

Scott, D. et al. (2007). "Transgastric, Transcolonic, and Transvaginal Cholecystectomy Using Magnetically Anchored Instruments," Surgical Endoscopy, vol. 21: S474.

Scott, D. et al. (2007). "Completely Transvaginal Cholecystectomy Using Magnetically Anchored Instruments," Surgical Endoscopy, vol. 21: S335.

Scott, D. et al. (2007). "Short-Term Survival Outcomes Following Transvaginal Notes Cholecystectomy Using Magnetically Anchored Instruments," Gastrointestinal Endoscopy, vol. 65: AB109.

Swain, C. et al. (2008). "Linear Stapler Formation of Ileo-Rectal, Entero-Enteral and Gastrojejunal Anastomoses During Dual and Single Access "Pure" Notes Procedures: Methods, Magnets and Stapler Modifications," Gastrointestinal Endoscopy, vol. 67: AB119.

Swain, P. et al. (2008). "Wireless Endosurgery for Notes," Gastrointestinal Endoscopy, vol. 67: AB104.

Tan, Y. (2011). "Modeling of Magnetic Tools for Use with Superparamagnetic Particles for Magnetic Stone Extraction," 26th Engineering & Urology Society Annual Meeting, p. 29, Washington DC, May 14, 2011.

Tan, Y. (2012). "In Vitro Comparison of Prototype Magnetic Tool with Conventional Nitinol Basket for Ureteroscopic Retrieval of Stone Fragments Rendered Paramagnetic with Iron-Oxide Microparticles," The Journal of Urology, vol. 187, Issue 4, pp. e857-858.

Tang, S. (2008). "Live Video Manipulator for Endoscopy and Notes," Gastrointestinal Endoscopy 68:559-564.

Tillander, H. (1951). "Magnetic guidance of a catheter with articulated steel tip," Acta Radiologica pp. 62-64.

Zeltser, I.S. et al. (2007). "Single trocar laparoscopic nephrectomy using magnetic anchoring and guidance system in the porcine model," J. of Urology 178:1-4.

U.S. Appl. No. 61/113,495, filed Nov. 25, 2008, by Fernandez et al. (Copy not attached).

Final Office Action dated Nov. 25, 2020, for U.S. Appl. No. 15/728,297, filed Oct. 9, 2017, 11 pages.

\* cited by examiner

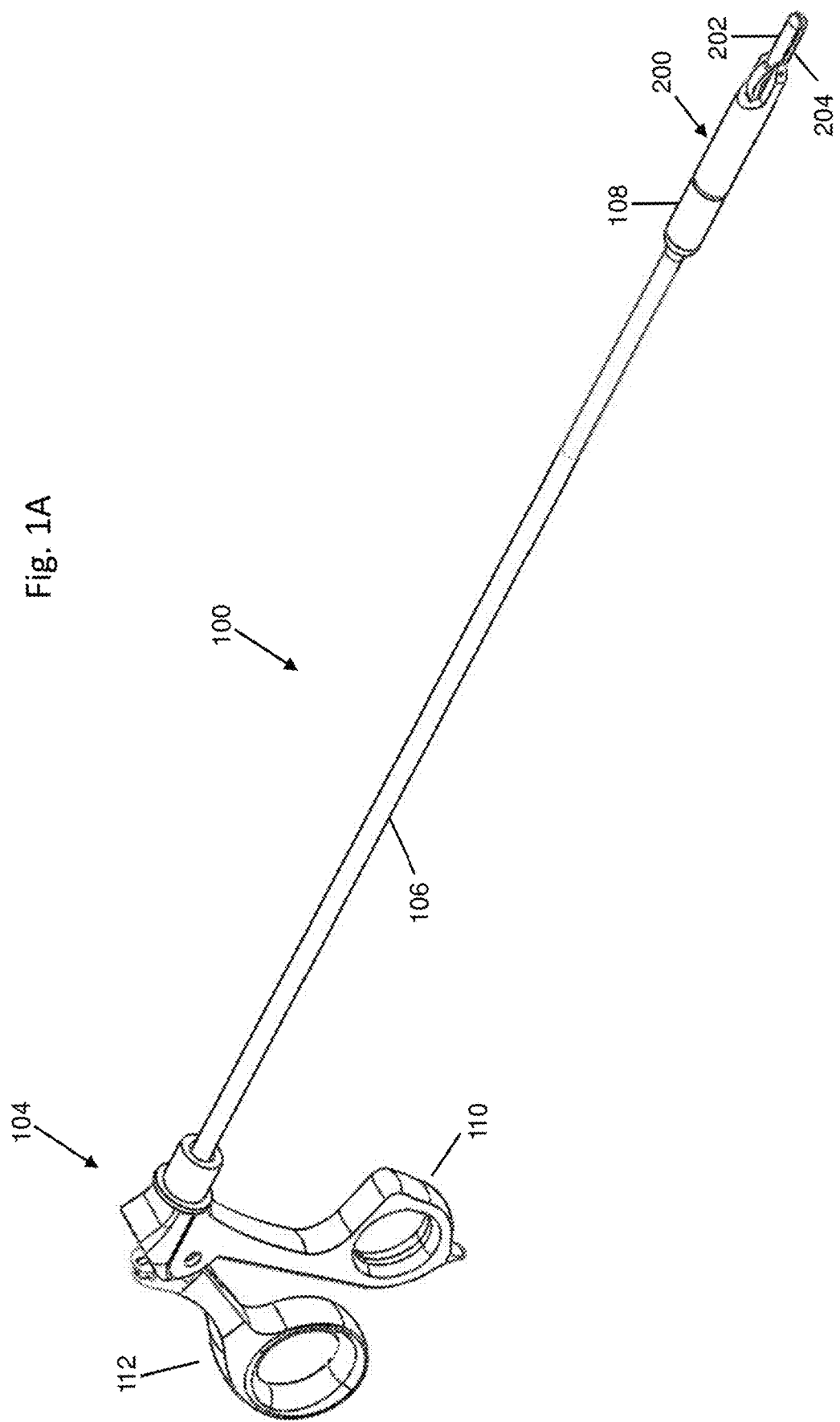

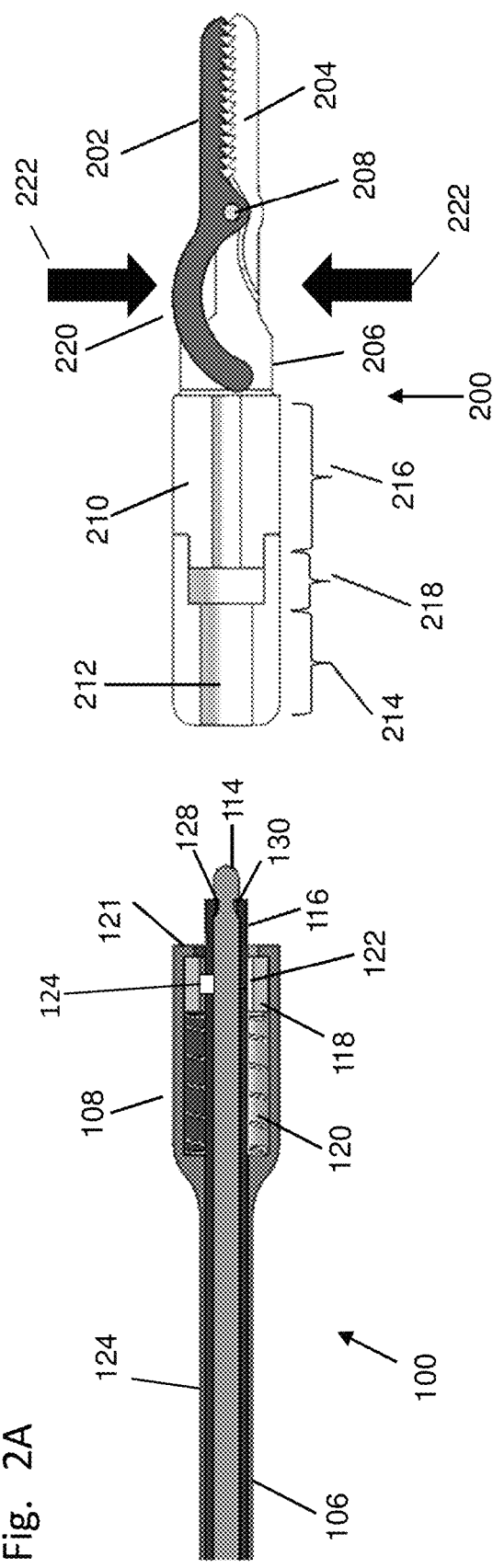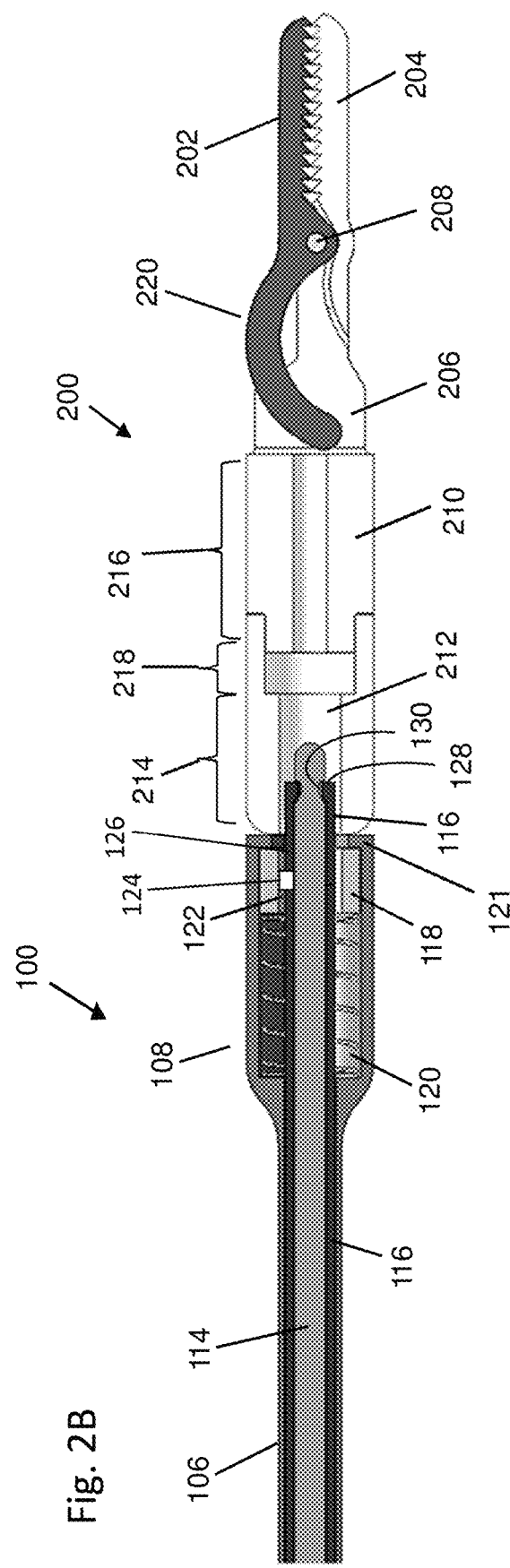
Fig. 2A
Fig. 2B

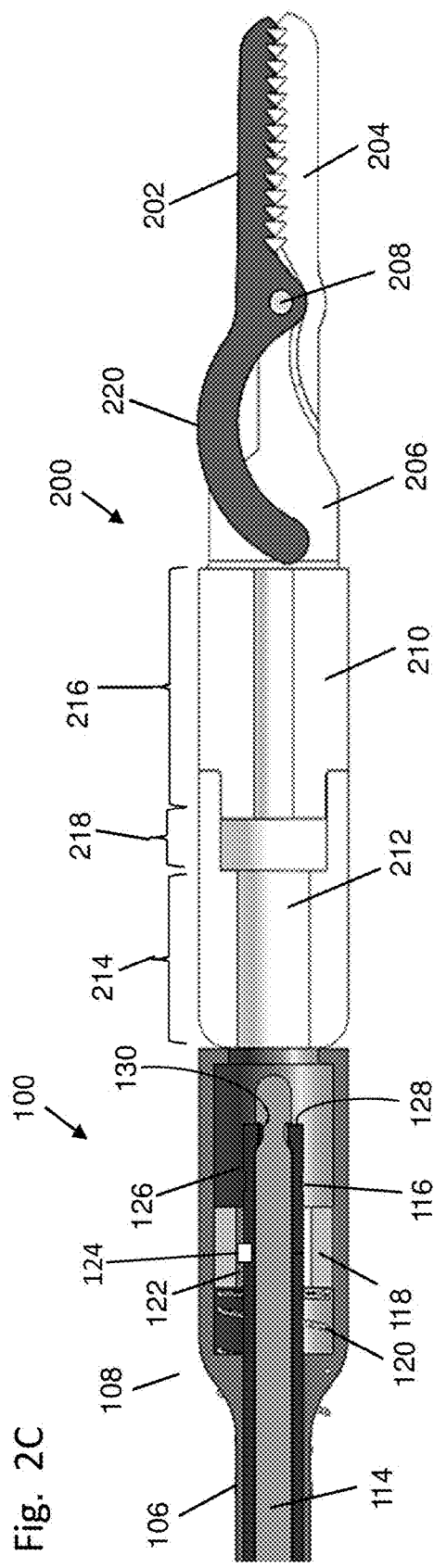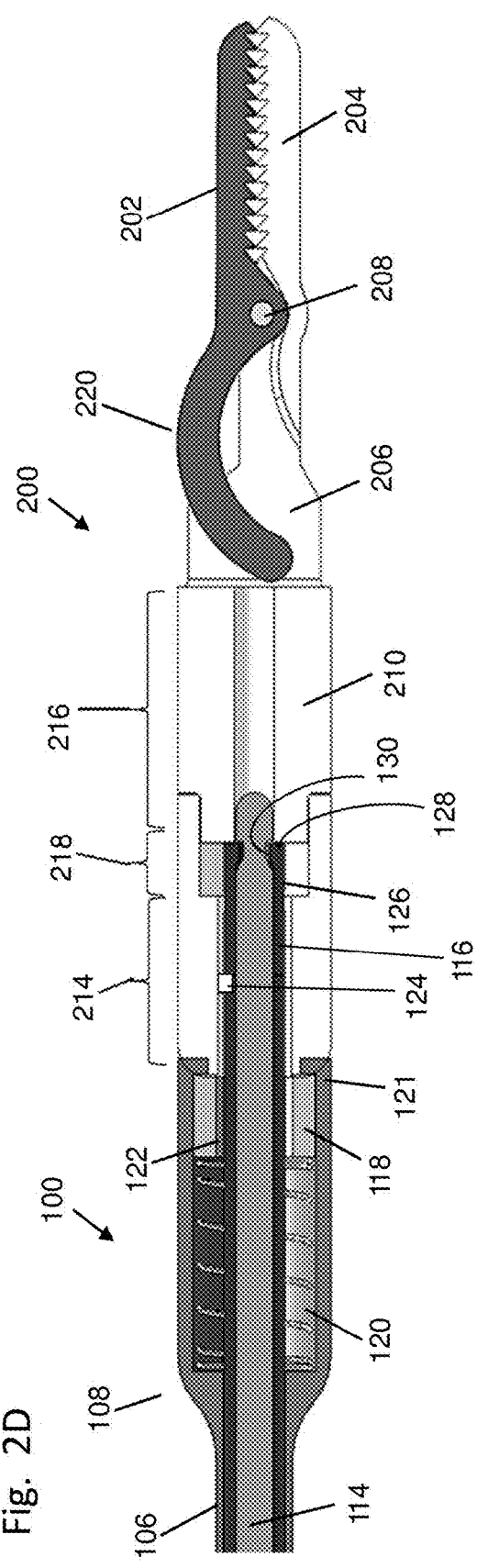

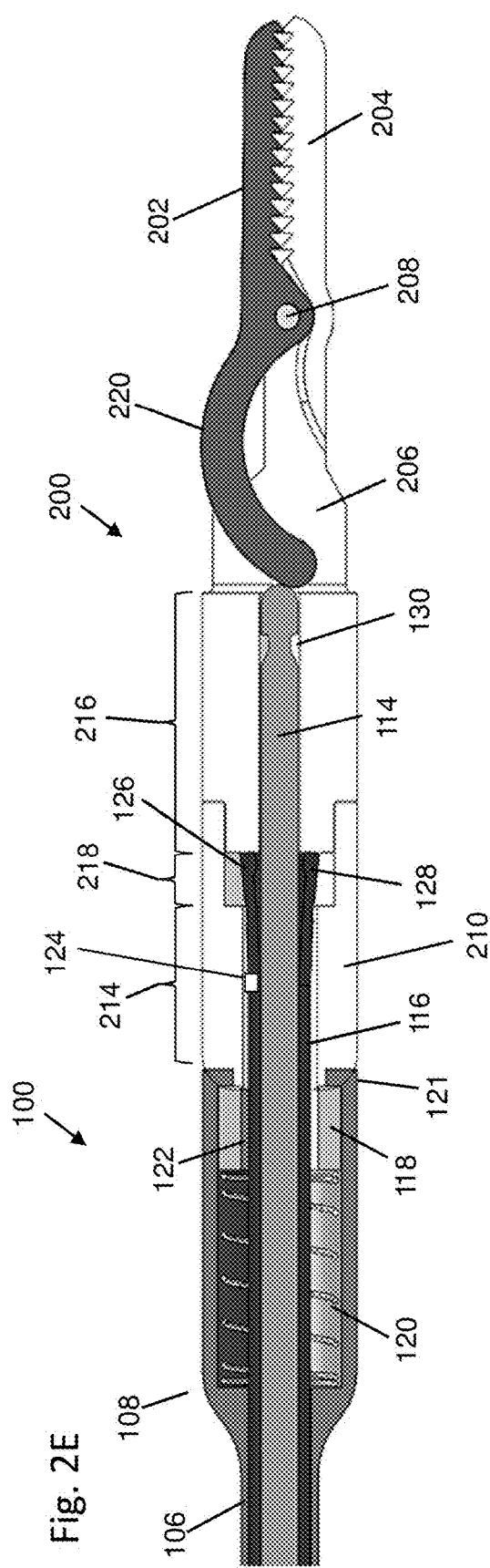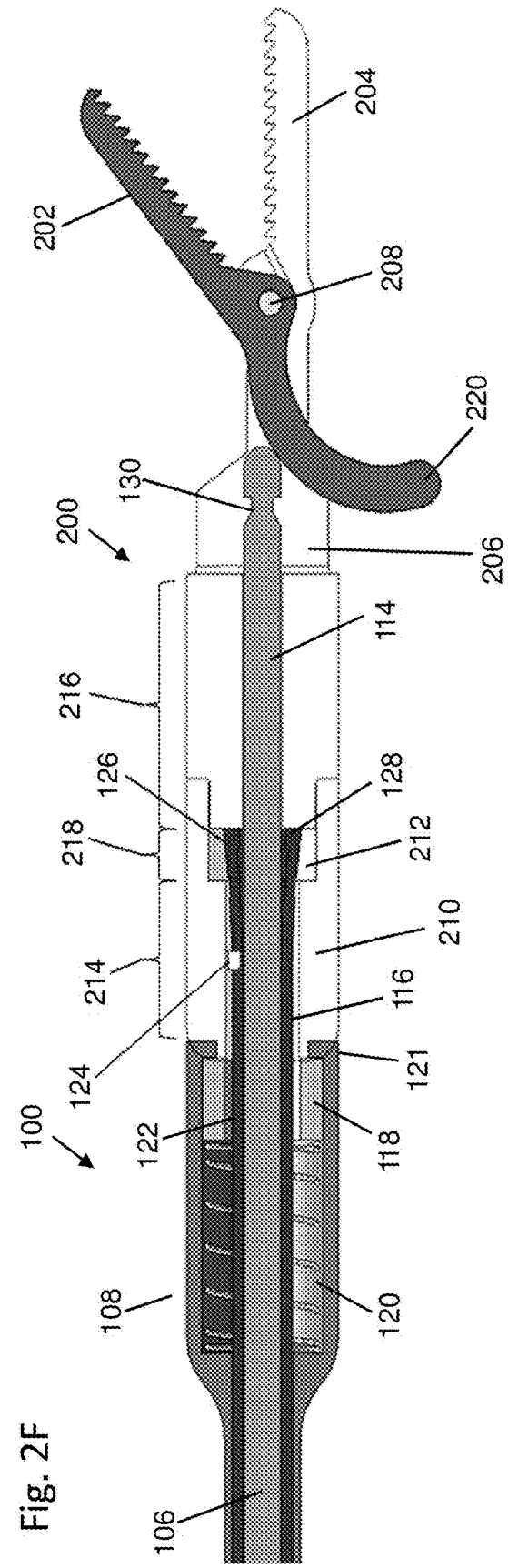

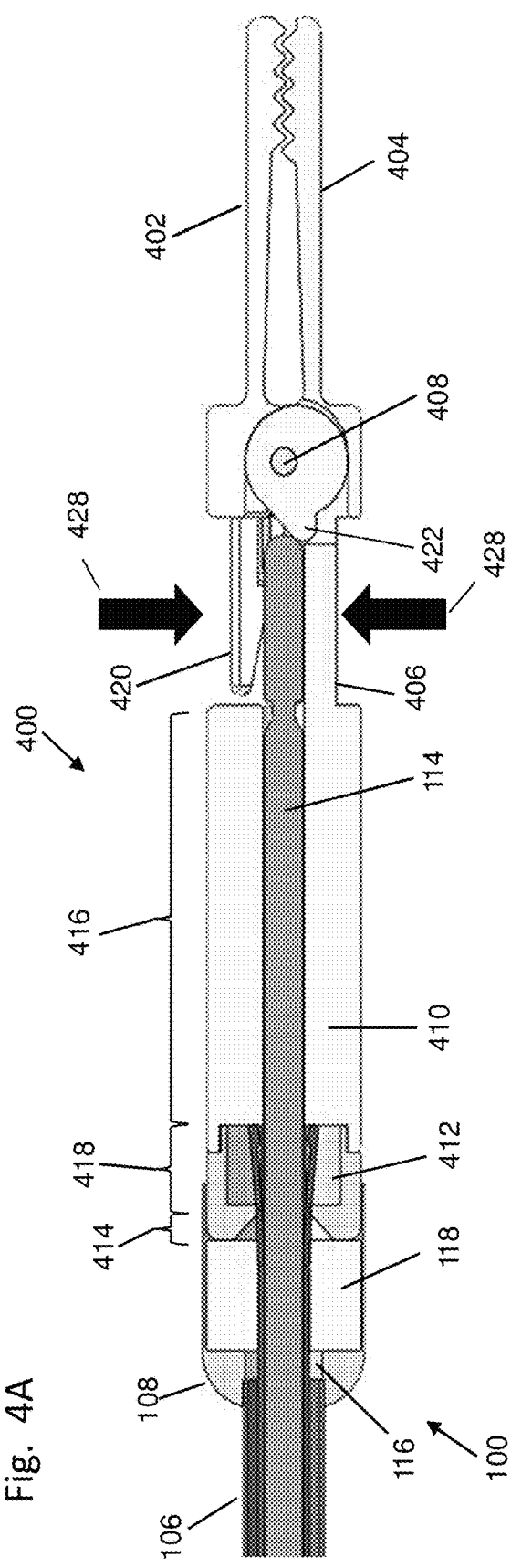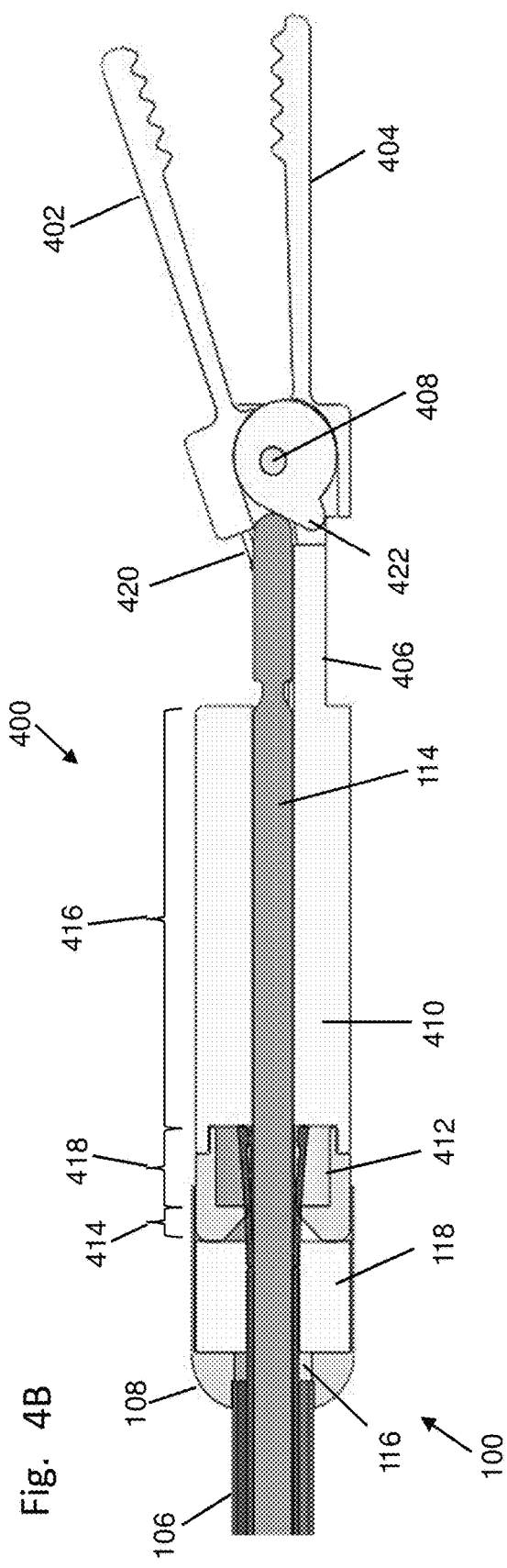

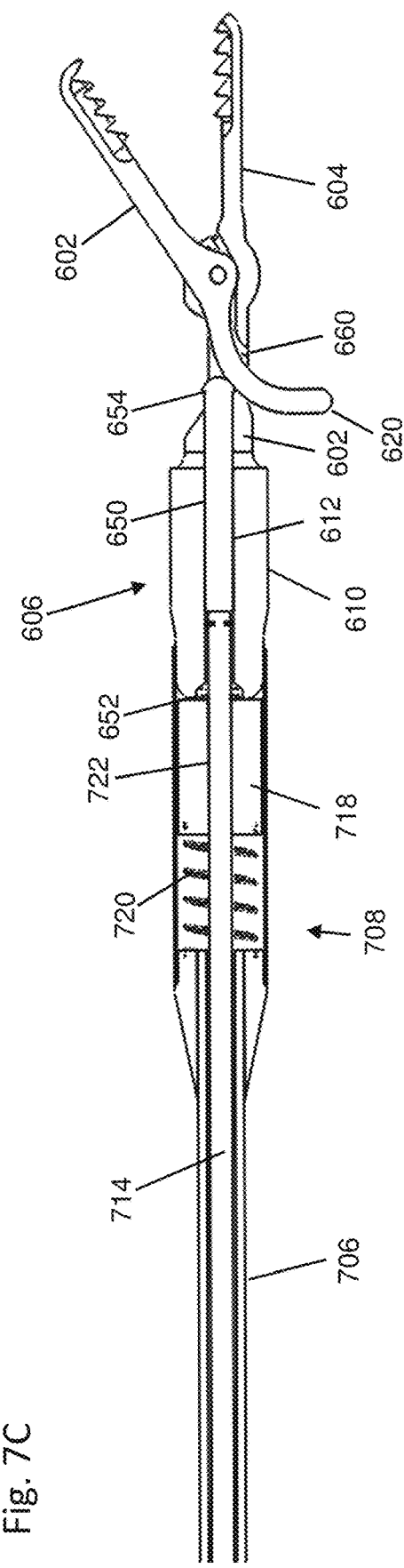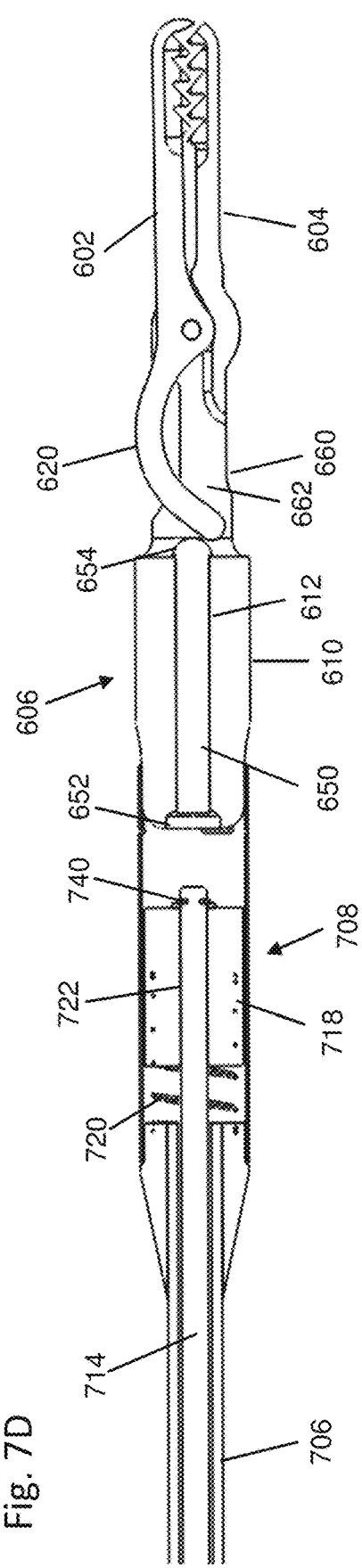

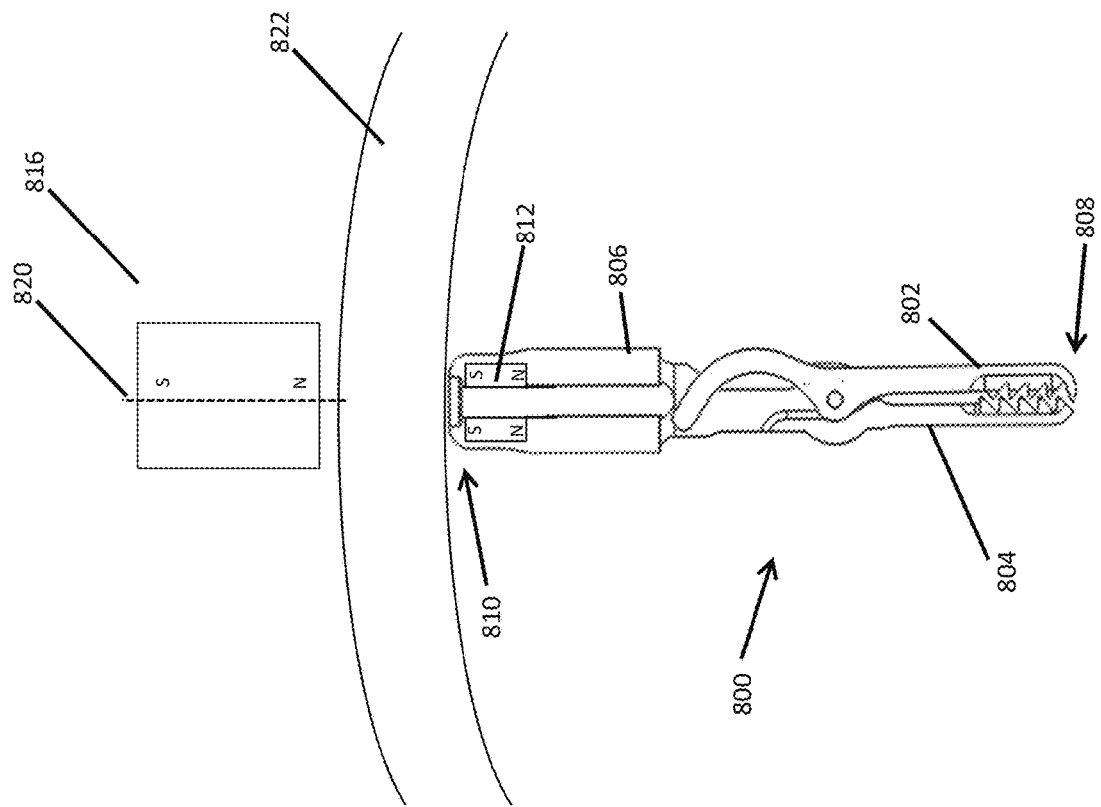
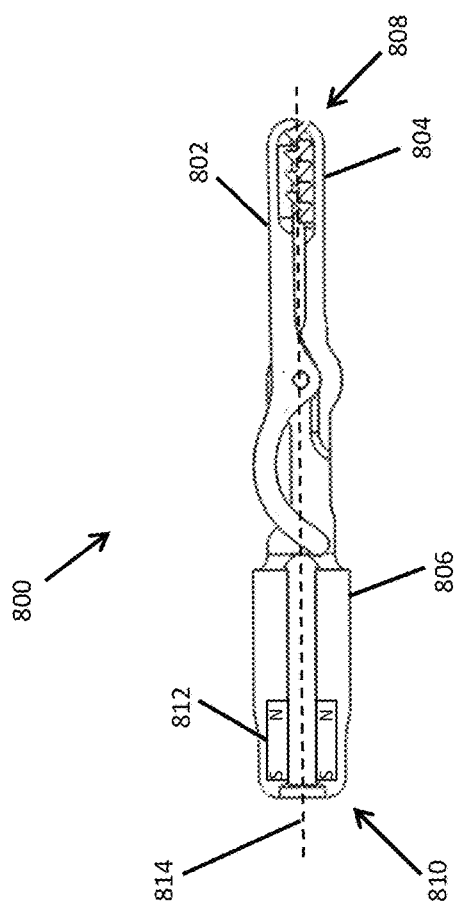
Fig. 8A
Fig. 8B

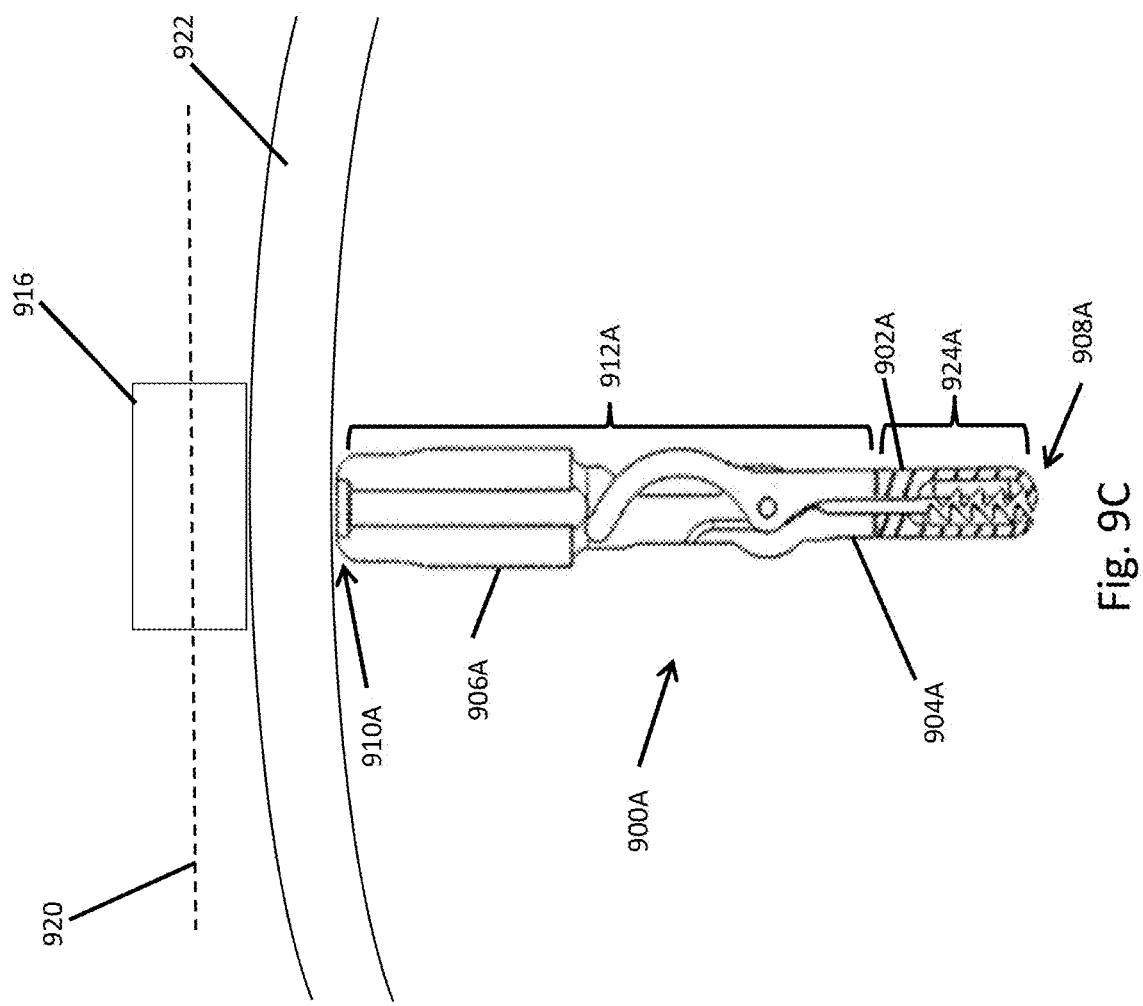

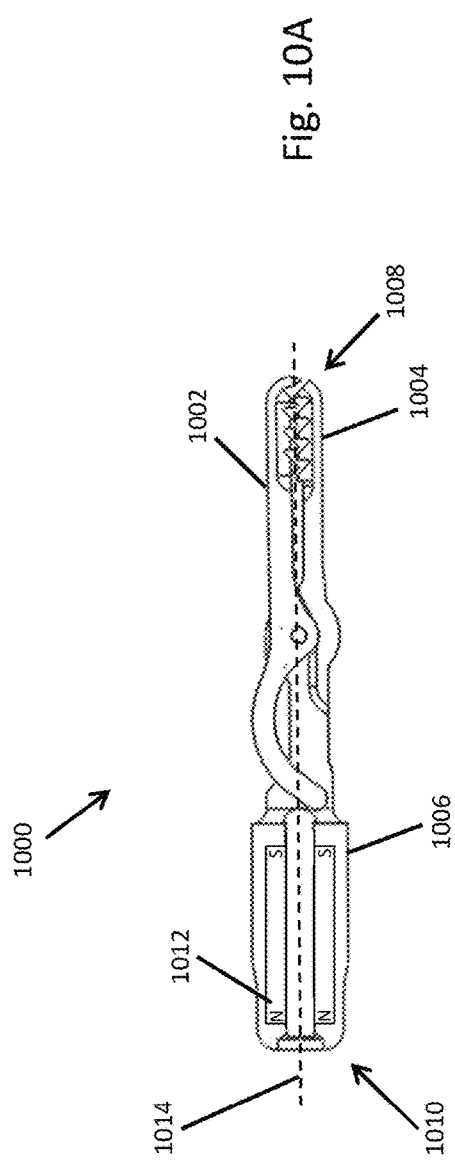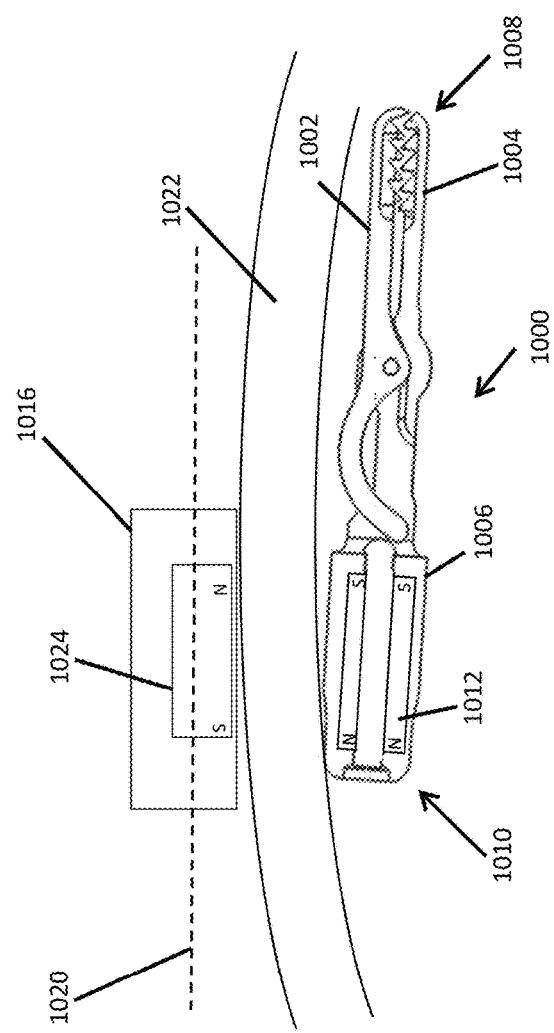

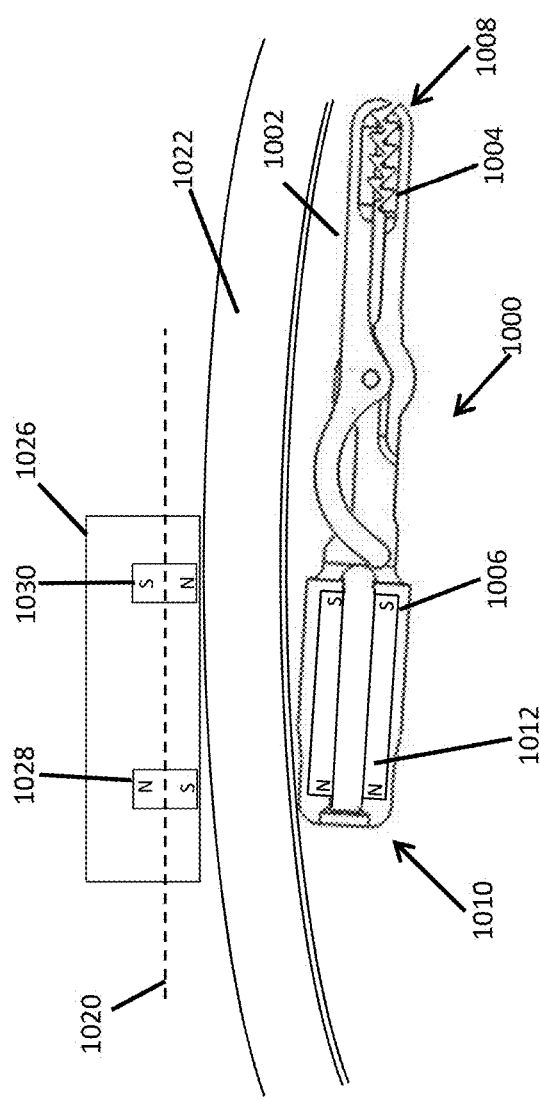
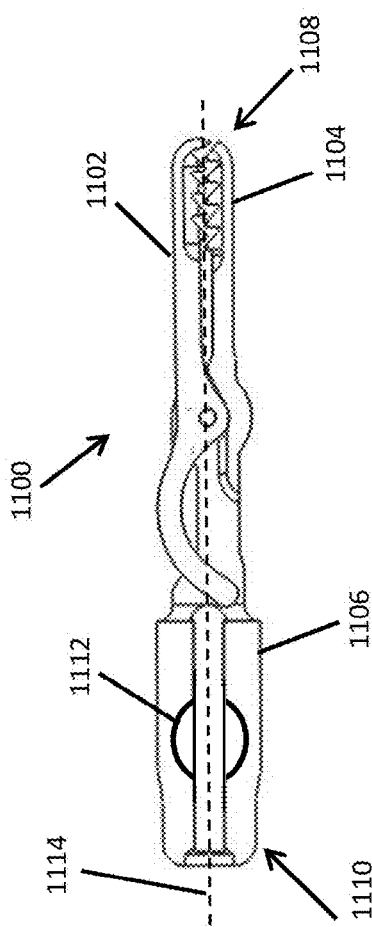
Fig. 10C
Fig. 11A

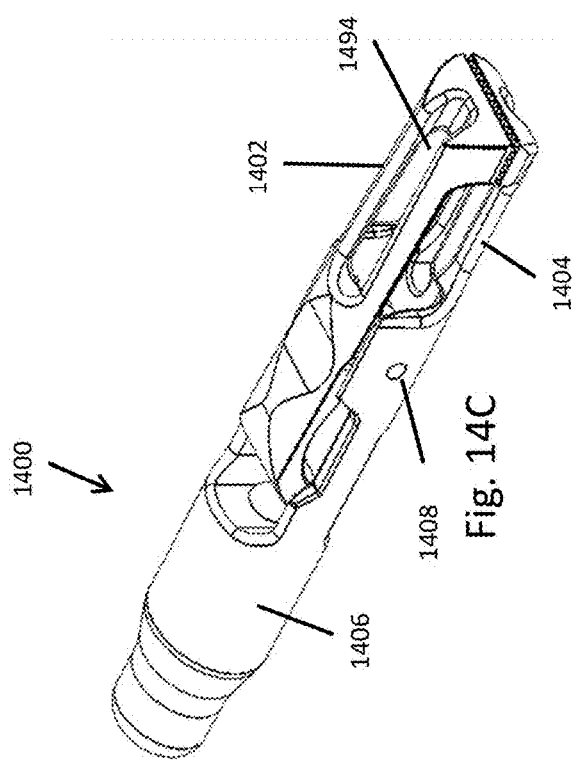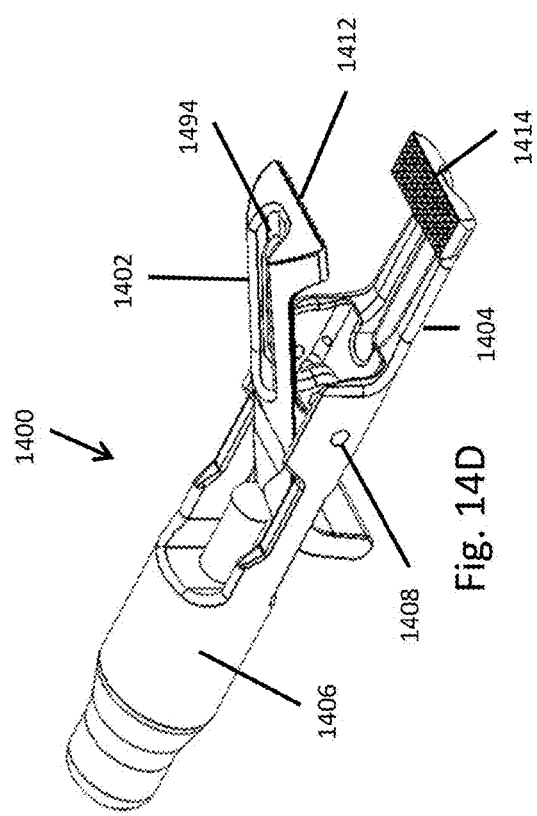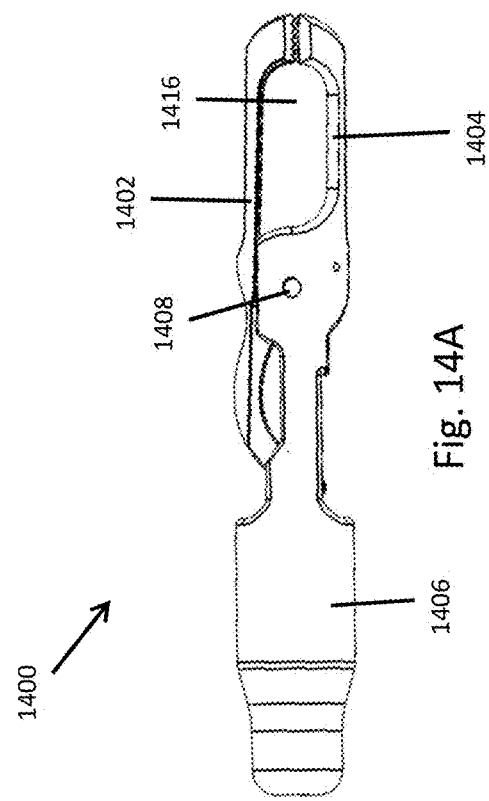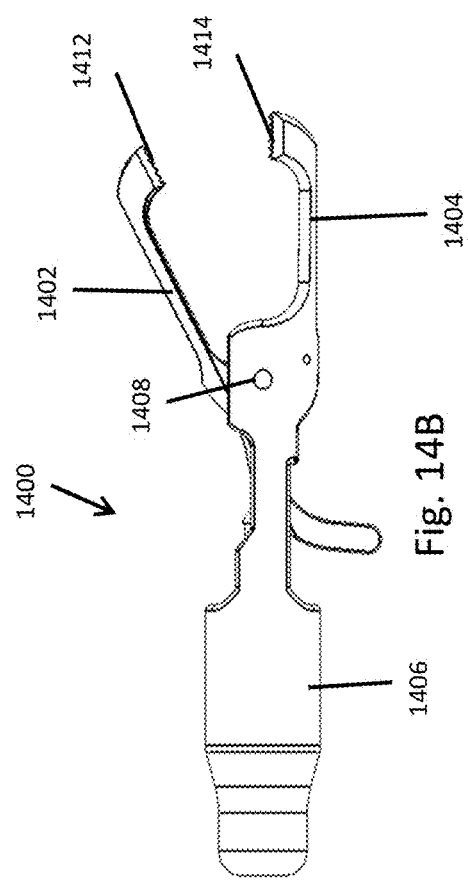

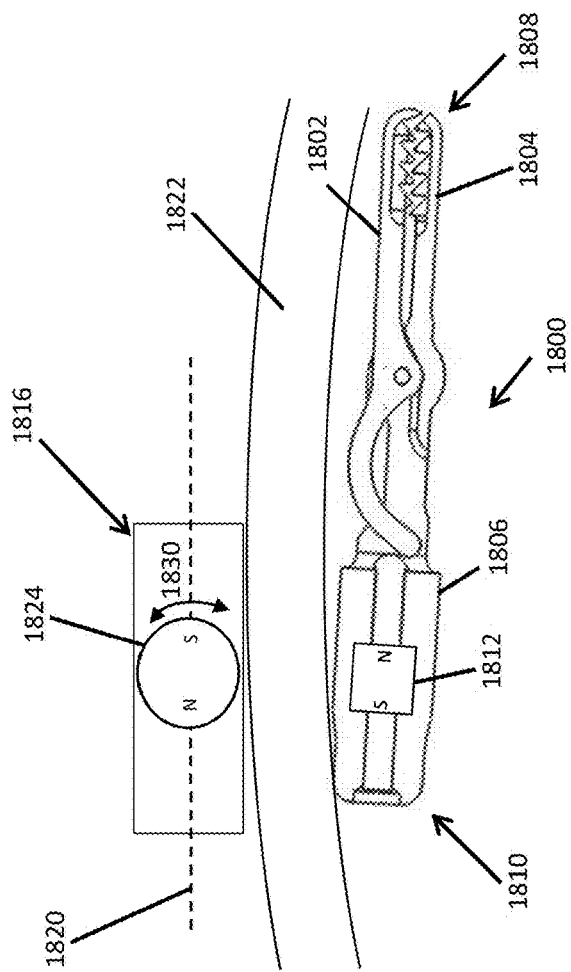
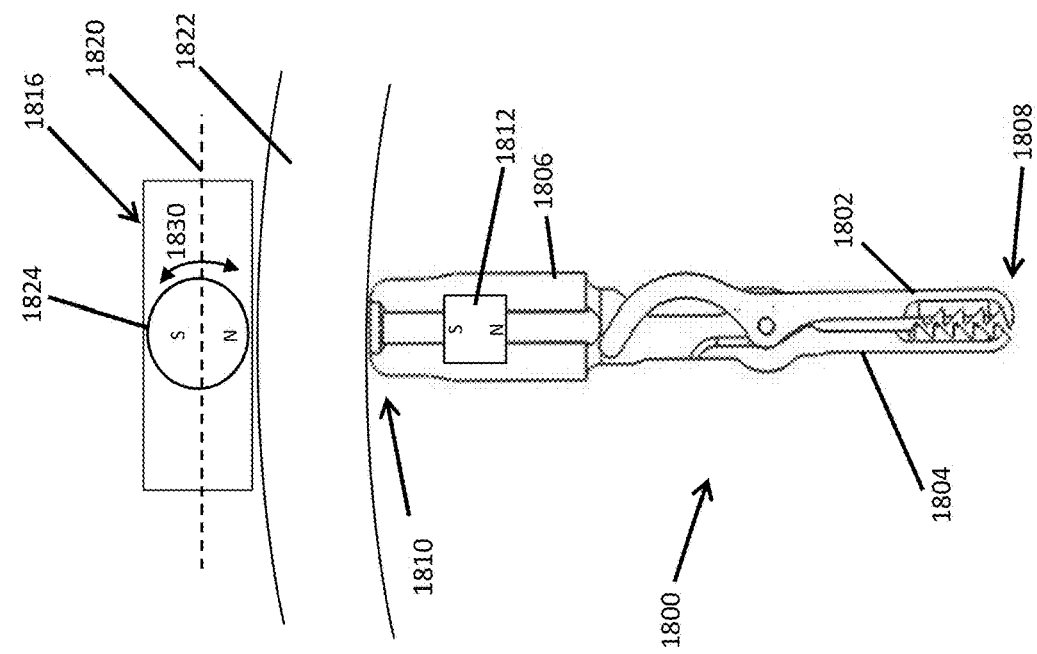
Fig. 18B
Fig. 18A

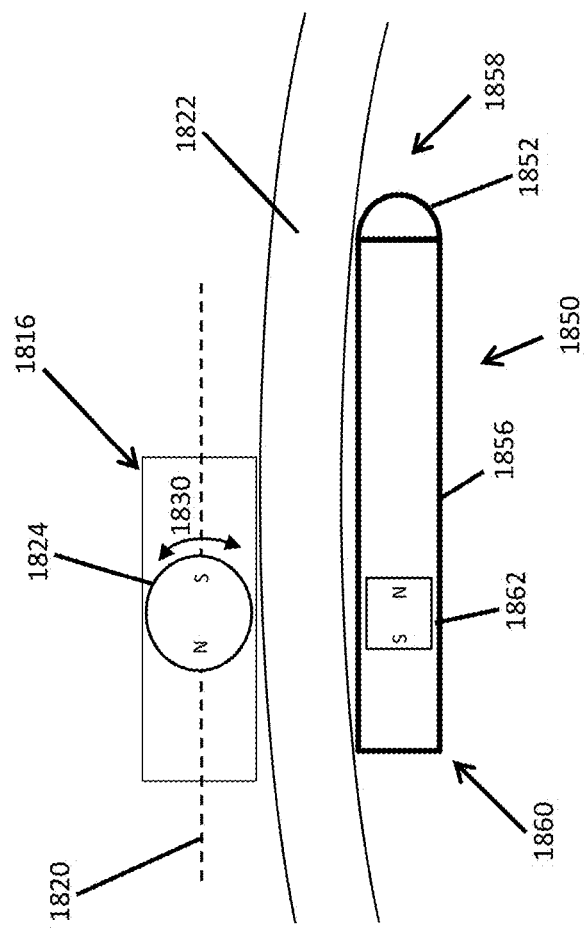
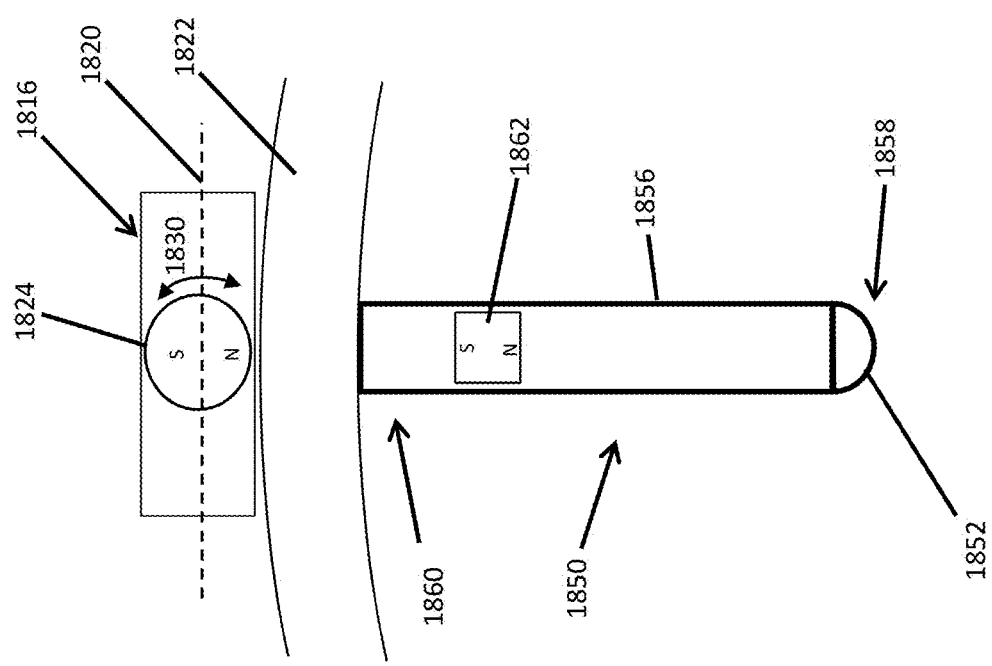
Fig. 18D
Fig. 18C

GRASPER WITH MAGNETICALLY-CONTROLLED POSITIONING

CROSS-REFERENCE TO RELATED APPLICATIONS

This application is a continuation filed under 35 U.S.C. § 120 of International Application No. PCT/US2016/027390, filed Apr. 13, 2016, and titled "GRASPER WITH MAGNETICALLY-CONTROLLED POSITIONING," which designated the United States and which claims priority to U.S. Provisional Application Ser. No. 62/146,922, filed on Apr. 13, 2015, and titled "GRASPER WITH MAGNETICALLY-CONTROLLED POSITIONING," and to U.S. Provisional Application Ser. No. 62/276,752, filed on Jan. 8, 2016, and titled "ONE-OPERATOR SURGICAL SYSTEM," the content of each of which is hereby incorporated by reference in its entirety.

FIELD

The present invention is directed toward systems, devices, and methods for providing remote manipulation or traction to tissue using one or more graspers.

BACKGROUND

Many surgical procedures are shifting toward the use of minimally-invasive approaches that are configured to minimize the number and size of incisions that are made in a patient. Minimally-invasive procedures such as endoscopic and laparoscopic procedures may be associated with lower pain, quicker post-surgical recovery, shortened hospitalization, and reduced complications when compared to open surgical procedures. During minimally-invasive procedures it may be desirable to reposition or otherwise manipulate tissue, however the introduction of additional devices to engage tissue may crowd the access sites provided by incisions, which may require the formation of larger or additional access sites. Accordingly, it may be desirable to provide one or more devices that may rotate, retract, pull, reposition, or otherwise manipulate tissue without the need to have a portion of the device present in an access site to the body.

BRIEF SUMMARY

Described here are systems, devices, and methods for providing remote traction for tissue. In some variations, the systems described here may grasp tissue. The systems may comprise a grasper comprising a proximal end, a distal end, and a longitudinal axis. The grasper may comprise a first magnetic element at the proximal end. The systems may further comprise a control element configured to move at least a portion of the grasper. The control element may comprise a second magnetic element and a longitudinal axis. The first and second magnetic elements may be configured to attract the proximal end of the grasper to the control element such that the longitudinal axis of the grasper is transverse to the longitudinal axis of the control element.

In some variations, the distal end of the grasper may comprise a non-magnetic or a diamagnetic material. In some of these variations, the distal end of the grasper may comprise plastic. In some variations, the distal end of the grasper may comprise a non-conductive material. In some instances, the first magnetic element may be a ferromagnetic material. In some of these instances, the ferromagnetic material may be a stainless steel. In some variations, the first magnetic element may comprise a permanent magnet.

In some variations, the grasper may comprise a closed configuration and an open configuration. In the closed configuration, the first jaw and second jaw may form a space configured to hold tissue. In other variations, the grasper may comprise a main body, a first jaw rotatably coupled to the main body, and a second jaw fixed relative to the main body.

In some variations, the second magnetic element may be configured to rotate relative to the control element. In other variations, the second magnetic element may comprise a diamagnetic material.

In some variations, the systems for grasping tissue described here may comprise a grasper comprising a longitudinal axis. The grasper may further comprise a first magnetic element positioned along its longitudinal axis. The systems may further comprise a control element configured to move at least a portion of the grasper. The control element may comprise a second magnetic element and a longitudinal axis. The first and second magnetic elements may be configured to attract the grasper to the control element such that the longitudinal axis of the grasper and the longitudinal axis of the control element are substantially parallel.

In some variations, the first magnetic element may comprise a ferromagnetic material. In other variations, the first magnetic element may comprise a permanent magnet. In some variations, the grasper may further comprise a third magnetic element. In some variations, the first magnetic element may be located at a proximal end of the grasper and the third magnetic element may be located at a distal end of the grasper.

In some variations, the grasper may further comprise a main body, a first jaw rotatably coupled to the main body, and a second jaw fixed relative to the main body. In some of these variations, at least one of the first jaw and second jaw may comprise a non-conductive material. In some instances, the first magnetic element may be positioned at a proximal end of the main body of the grasper. In some variations, the grasper may comprise a closed configuration and an open configuration. In the closed configuration, the first jaw and second jaw may form a space configured to hold tissue.

In some variations, the second magnetic element may be configured to rotate relative to the control element. In other variations, the second magnetic element may comprise a diamagnetic material.

In some variations, the systems for grasping tissue described here may comprise a grasper comprising a main body, a longitudinal axis, and a first magnetic element. The first magnetic element may be positioned in the main body. The systems may further comprise a control element configured to move at least a portion of the grasper. The control element may comprise a second magnetic element and a longitudinal axis. The first and second magnetic elements may be configured to attract the main body of the grasper to the control element such that the longitudinal axis of the grasper and the longitudinal axis of the control element are substantially parallel.

In some variations, the first magnetic element may be the material of the main body of the grasper. In other variations, the first magnetic element may comprise a permanent magnet. In still other variations, the grasper may further comprise a first jaw rotatably coupled to the main body and a second jaw fixed relative to the main body.

In some variations, the second magnetic element may be configured to rotate relative to the control element. In other variations, the second magnetic element may comprise a diamagnetic material.

In yet other variations, the systems for grasping tissue described here may comprise a grasper comprising a longitudinal axis, a first magnetic element, and a second magnetic element. The systems may further comprise a control element configured to move at least a portion of the grasper. The control element may comprise a third magnetic element, a fourth magnetic element, and a longitudinal axis. The third and fourth magnetic elements may be configured to attract the first and second magnetic elements such that the longitudinal axis of the grasper and the longitudinal axis of the control element are substantially parallel.

In some variations, the first and second magnetic elements may comprise permanent magnets. In some instances, the third and fourth magnetic elements may comprise permanent magnets. In other instances, the third magnetic element may comprise a permanent magnet and the fourth magnetic element may comprise a ferromagnetic or a ferrimagnetic material. In some variations, the third and fourth magnetic elements may comprise electro-permanent magnets. In other variations, the third and fourth magnetic elements may comprise electromagnets.

In some variations, the grasper may further comprise a main body, a first jaw rotatably coupled to the main body, and a second jaw fixed relative to the main body. In some of these variations, at least one of the first jaw and second jaw may comprise a non-conductive material. In other variations, the third and fourth magnetic elements may be configured to rotate relative to the control element. In yet other variations, the third and fourth magnetic elements may comprise a diamagnetic material.

In some variations, the methods of performing a surgical procedure described here may comprise grasping tissue in a grasper and magnetically attracting the grasper to a control element across an abdominal wall. The grasped tissue may be repositioned by manipulating a magnetic element of the control element.

In some variations, the methods of performing a surgical procedure described here may comprise manipulating a first portion of tissue within a body cavity of a patient with a first grasper, and manipulating a second portion of tissue within the body cavity with a second grasper. Manipulating the first portion of tissue with the first grasper may comprise advancing the first grasper into the body cavity through a first port using a delivery device, connecting the first grasper to the first portion of tissue within the body cavity, disconnecting the delivery device from the first grasper, and applying a first magnetic field to the first grasper. Manipulating the second portion of tissue with the second grasper may comprise advancing the second grasper into the body cavity through the first port or through a second port using the delivery device, connecting the second grasper to the second portion of tissue within the body cavity, disconnecting the delivery device from the second grasper, and applying a second magnetic field to the second grasper.

In some variations, the first magnetic field may be generated by a first control element. The first control element may be located outside of the body cavity. In some of these variations, the second magnetic field may be generated by a second control element. The second control element may be located outside of the body cavity. In some of these variations, the first and second control elements may be connected by a linkage.

In some variations, at least one of the first and second grasper may comprise a main body, a first jaw, and a second jaw, and may comprise a closed configuration and an open configuration. In some instances, in the closed configuration, the first jaw and second jaw may form a space configured to hold tissue. In some variations, the second grasper may be advanced into the body cavity through the first port. In some variations, the second grasper may be advanced into the body cavity through the second port. In some variations, the first grasper and second grasper may be advanced into the body cavity prior to applying either the first magnetic field or second magnetic field.

In some variations, the method may further comprise manipulating a third portion of tissue within the body cavity of the patient with the first grasper. In some of these variations, manipulating the third portion of tissue with the first grasper may comprise disconnecting the first grasper from the first portion of tissue, connecting the first grasper to the third portion of tissue within the body cavity, and applying the first magnetic field to the first grasper connected to the third portion of tissue. In some instances, a fourth portion of tissue may be manipulated within the body cavity of the patient with the second grasper. In some of these instances, manipulating the fourth portion of tissue with the second grasper may comprise disconnecting the second grasper from the second portion of tissue, connecting the second grasper to the fourth portion of tissue within the body cavity, and applying the second magnetic field to the second grasper connected to the fourth portion of tissue.

In other variations, the systems described here may visualize tissue. The systems may comprise a visualization device comprising a proximal end, a distal end, and a longitudinal axis. The visualization device may comprise a first magnetic element at the proximal end. The systems may comprise a control element configured to move at least a portion of the visualization device. The control element may comprise a second magnetic element and a longitudinal axis. The first and second magnetic elements may be configured to attract the proximal end of the visualization device to the control element such that the longitudinal axis of the visualization device is transverse to the longitudinal axis of the control element.

In some variations, the distal end of the visualization device may comprise a third magnetic element. In other variations, the distal end of the visualization device may comprise a non-magnetic or a diamagnetic material. In some instances, the distal end of the visualization device may comprise plastic. In some variations, the first magnetic element may be a ferromagnetic material. In other variations, the distal end of the visualization device may comprise a non-conductive material. In some instances, the ferromagnetic material may be stainless steel. In some variations, the first magnetic element may comprise a permanent magnet. In other variations, the second magnetic element may be configured to rotate relative to the control element. In some variations, the visualization device may be a camera. In some variations, the visualization device may be a light source. In other variations, the visualization device may be a camera and a light source.

In yet other variations, the systems described here may visualize tissue. The systems may comprise a visualization device comprising a longitudinal axis. The visualization device may comprise a first magnetic element positioned along its longitudinal axis. The systems may comprise a control element configured to move at least a portion of the visualization device. The control element may comprise a second magnetic element and a longitudinal axis. The first and second magnetic elements may be configured to attract the visualization device to the control element such that the longitudinal axis of the visualization device and the longitudinal axis of the control element are substantially parallel.

In some variations, the first magnetic element may comprise a ferromagnetic material. In other variations, the first magnetic element may comprise a permanent magnet. In some variations, the visualization device may further comprise a third magnetic element. The first magnetic element may be located in a proximal end of the visualization device and the third magnetic element may be located in a distal end of the visualization device. In other variations, a distal end of the visualization device may comprise a non-conductive material. In yet other variations, the second magnetic element may be configured to rotate relative to the control element. In some variations, the second magnetic element may comprise a diamagnetic material.

In some variations, the methods of performing a surgical procedure described here may comprise imaging tissue with a camera in a body cavity and magnetically attracting the camera to a control element across an abdominal wall. The camera may be repositioned within the body cavity by manipulating a magnetic element of the control element.

In some variations, manipulating the magnetic element of the control element may comprise rotating the magnetic element relative to the control element. In other variations, the camera may be configured to be asymmetrically attracted to a magnetic field.

BRIEF DESCRIPTION OF THE DRAWINGS

FIGS. 1A-1C depict perspective views of an illustrative variation of the systems described here.

FIGS. 2A-2F depict cross-sectional side views of a distal portion of an illustrative variation of the delivery devices described here and an illustrative variation of the graspers described here.

FIGS. 3A-3B and 4A-4B depict cross-sectional side views of illustrative variations of the graspers described here.

FIGS. 7A-7D depict cross-sectional side views of a distal portion of an illustrative variation of the delivery devices described here and the grasper of FIGS. 6A and 6B.

FIG. 8A depicts a cross-sectional side view of an illustrative variation of a grasper described here. FIG. 8B depicts a cross-sectional side view of the grasper of FIG. 8A in use with a control element.

FIG. 9C depicts a cross-sectional side view of the grasper of FIG. 9A in use with a control element.

FIG. 10A depicts a cross-sectional side view of an illustrative variation of a grasper described here. FIGS. 10B and 10C depict cross-sectional side views of the grasper of FIG. 10A in use with a control element.

FIG. 11A depicts a cross-sectional side view of another illustrative variation of a grasper described here.

FIGS. 14A-14B and 14C-14D depict side and perspective views, respectively, of an illustrative variation of a grasper as described here.

FIGS. 18A-18B depict cross-sectional side views of an illustrative variation of a grasper in use with a control element. FIGS. 18C-18D depict cross-sectional side views of an illustrative variation of a camera in use with a control element.

DETAILED DESCRIPTION

Figure 1B:
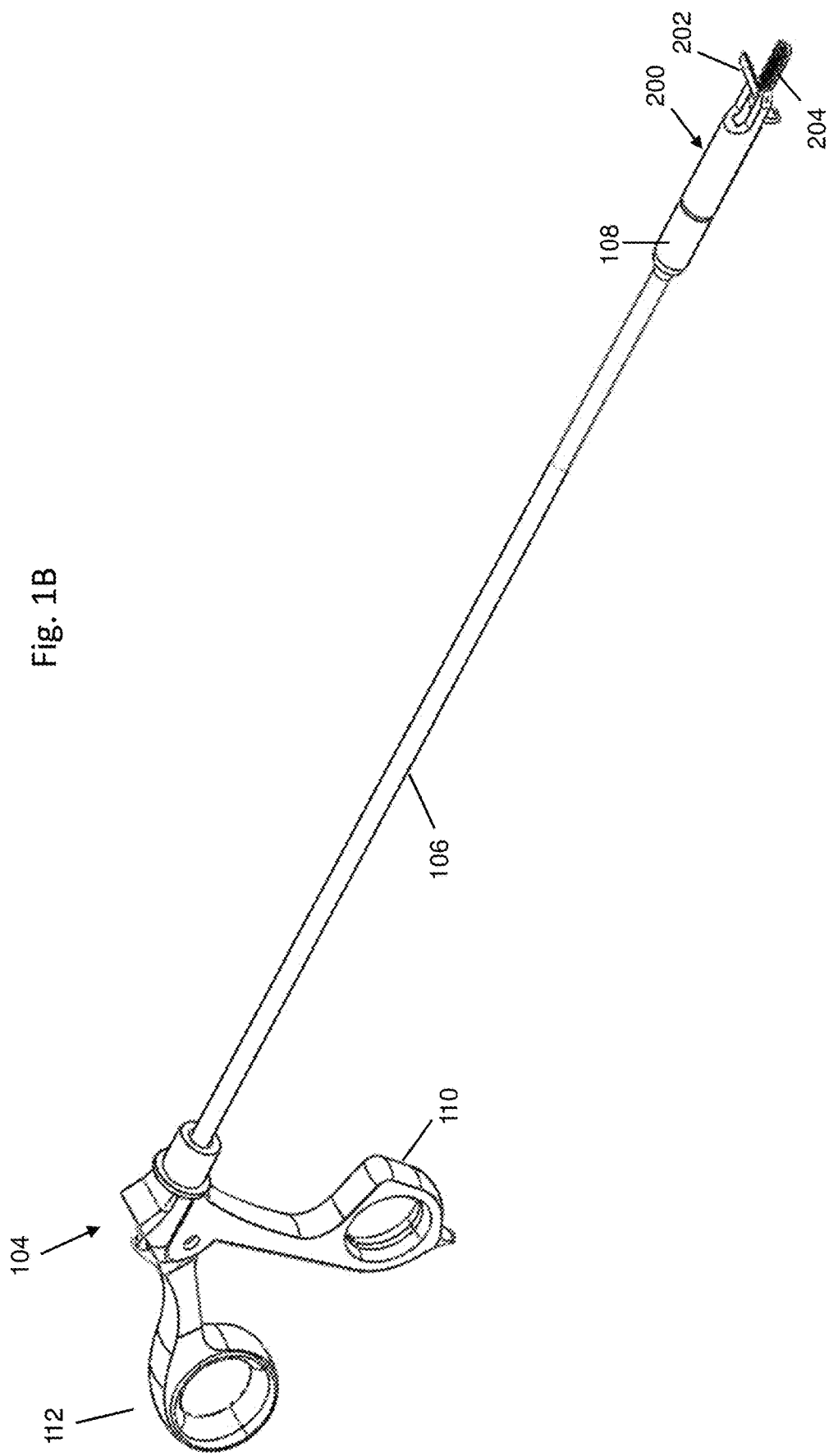

Described here are devices, systems, and methods for providing remote suspension/traction and/or manipulation of tissue during minimally-invasive procedures. Generally, the systems described here include a grasper that may be configured to be releasably connected to tissue. The grasper may be further configured to be attracted to one or more magnetic elements positioned externally of the body to move, reposition, and/or hold the grasper (which may in turn provide traction for the tissue held by the grasper). In some variations, the systems described here may additionally or alternatively comprise a visualization device (e.g., camera, light source) configured to be attracted to one or more magnetic elements positioned externally of the body to move, reposition, and/or hold the visualization device in a desired location and orientation for visualization during a minimally-invasive procedure.

The systems described here may also comprise a delivery device. The delivery devices described here are generally configured to releasably carry the grasper, and may be further configured to actuate the grasper to selectively connect the grasper to tissue or release the grasper from tissue. The delivery devices are typically further configured to release the grasper from the delivery device (e.g., after the grasper has been connected to tissue). In some instances, the delivery device may be configured to re-couple to the grasper to reposition or remove the grasper. In other instances the system may comprise a separate retrieval device configured to reposition or remove the grasper. In some instances, the delivery device or retrieval device may be used with the grasper to remove tissue from the body. For example, the grasper may be connected to a tissue such as a gall bladder, the tissue may be severed from the body (e.g., using one or more surgical tools), and the grasper may be retrieved using the delivery device or another retrieval device to remove the grasper and tissue from the body. It should be appreciated that while delivery devices are described herein primarily with reference to use with a grasper, the delivery devices described herein may also be used to reversibly couple to another tool to deliver, position and reposition, and/or remove another tool. For example, in some instances the delivery devices may be used to deliver, position and reposition, and/or remove a visualization device, such as a camera and/or light source.

In some variations, the system may comprise a control element (which may include one or more magnetic elements), which may be configured to be positioned outside the body and to provide a magnetic force to the grasper when the grasper is positioned in the body (e.g., to move, reposition, and/or hold the grasper). The control elements described herein may additionally or alternatively provide a magnetic force to a visualization device (e.g., camera, light source) when a visualization device is positioned within the body (e.g., to move, reposition, and/or hold the visualization device). While illustrative examples of the graspers and delivery devices are described together below, it should be appreciated that any of the graspers described here may be used with any of the delivery devices described here, and that any suitable visualization device (e.g., camera, light source) may be used with any of the delivery devices described herein. It should be appreciated that the graspers described here may be actuated and delivered using any suitable delivery device, and that that the delivery devices described here may be used to actuate and deliver any suitable grasper or grasping device. Moreover, while illustrative examples of graspers, visualization devices, and control elements are described together below, it should be appreciated that the control elements may be used with any of the graspers, delivery devices, and suitable visualization devices described here.

Generally, the methods described here comprise releasably connecting a grasper (such as one of the graspers described here) to a tissue, and providing a magnetic force to the grasper to move and/or hold the grasper and provide traction of the tissue engaged by the grasper. The magnetic force may be provided by a control element configured to attract and/or repel the grasper.

In some variations, the grasper may be releasably connected to a tissue inside of the body, and the control element may be positioned externally of the body to affect (e.g., attract, repel, rotate) the grasper. To connect the grasper to the tissue, the grasper may be releasably coupled with a delivery device, wherein the delivery device is configured to actuate the grasper. The delivery device may actuate the grasper to releasably connect the grasper to tissue, and may eject or otherwise decouple from the grasper after the grasper is connected to tissue. When the grasper is decoupled from the delivery device, the grasper may be attracted by a magnetic force external to the body and may move or otherwise hold tissue without the need to have a shaft or other portion of a device positioned in a port or oilier access site. This may reduce the number of access sites required to provide remote suspension of tissue, which may allow for faster and more reliable surgical procedures. In some instances, the delivery device (or another device, such as a grasping device) may be used to disconnect the grasper from tissue. The grasper may then be repositioned and reattached to tissue (either the same tissue or a different tissue), or may be removed from the body. Additionally or alternatively, the methods may comprise controlling the position and/or orientation a visualization device (e.g., camera, light source) located within the body with a magnetic field generated outside the body by a control element as described herein.

I. Systems and Devices

Figure 1C:
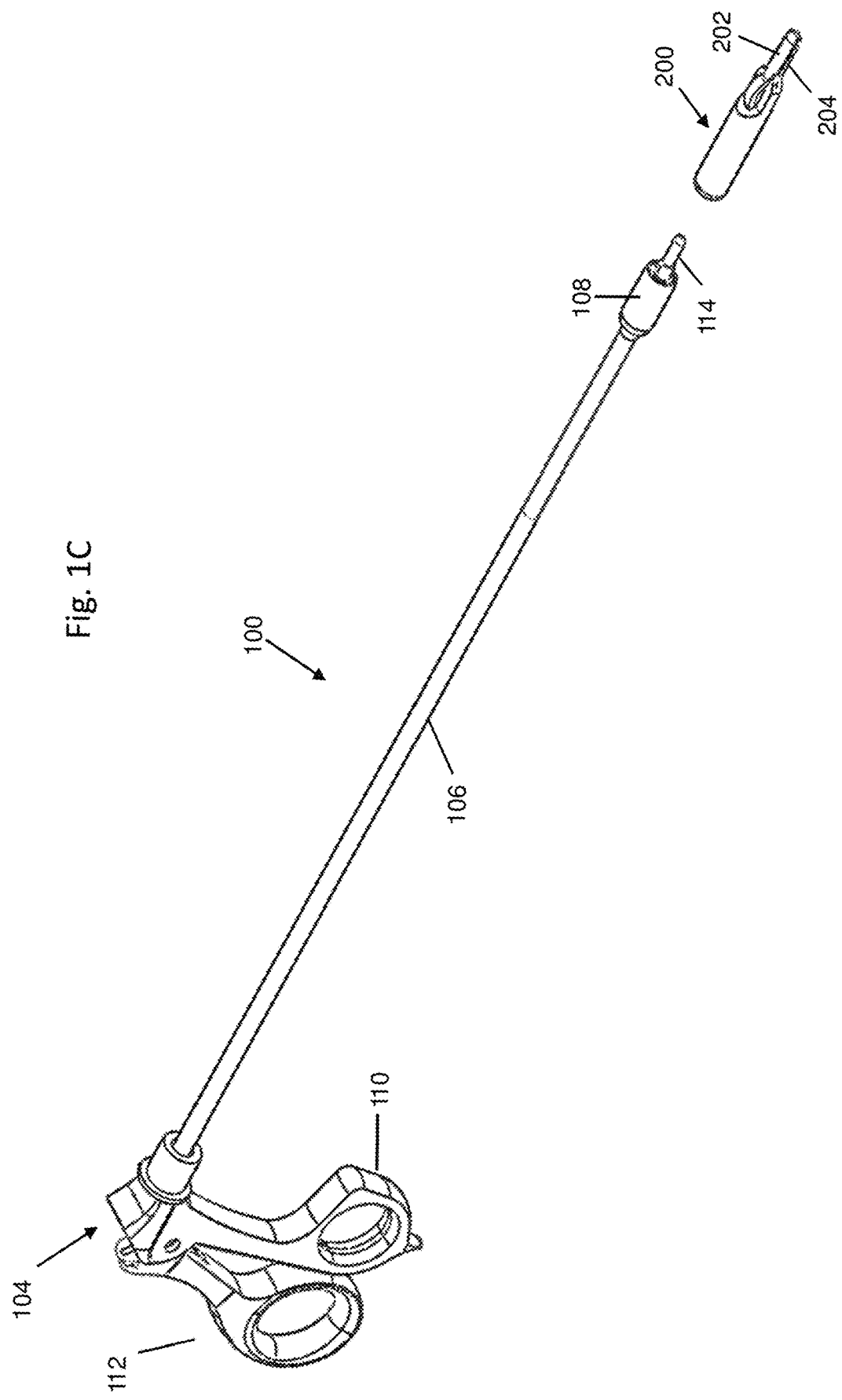

FIGS. 1A-1C depict one variation of the systems described here. Specifically, FIG. 1A shows a perspective view of a system comprising a delivery device (100) and a grasper (200). The grasper (200) may be releasably coupled to the delivery device (100) (as shown in FIGS. 1A and 1B), and may be decoupled from the delivery device (100) (as shown in FIG. 1C). When the grasper (200) is coupled to the delivery device (100), the delivery device (100) may actuate the grasper to connect the grasper to tissue and/or release the grasper therefrom.

As shown in FIG. 1A, the delivery device (100) may comprise a handle (104), a shaft (106) extending from the handle (104), and a distal engagement portion (108) at a distal end of the shaft (106). In some variations, the delivery device (100) and grasper (200) may be configured for minimally invasive introduction into a body. For instance, in some variations the grasper (200) and delivery device (100) may be configured for advancement through a 10 mm port. In these variations, the outer diameter of the grasper (200) may be less than or equal to about 10 mm. Additionally, the delivery device (100) may be configured such that the shaft (106) and the distal engagement portion (108) may each have a diameter of less than or equal to about 10 mm.

In some of these variations, the distal engagement portion (108) may have an outer diameter of less than or equal to about 10 mm, while the shaft (106) has an outer diameter of less than or equal to about 5 mm. In these variations, it may be possible to advance the distal engagement portion (108) through a 10 mm port, and to further advance a second device having a diameter of about 5 mm or less through the port while the shaft (106) is positioned in the port.

It should be appreciated that shaft (106) may have any suitable diameter (e.g., between about 1 mm and about 15 mm, between about 5 mm and about 10 mm, or the like). The shaft (106) and distal engagement portion (108) may be formed from any suitable materials, such as one or more medical-grade, high-strength plastics or metals, such as stainless steel, cobalt chromium, PEEK, one or more nylons, polyimide, polycarbonate, ABS, or the like.

It should be appreciated that the systems disclosed herein may comprise a delivery device (100) releasably coupled to a different device than a grasper (200), in order to perform one or more functions within a body cavity. For instance, the delivery device (100) may be coupled to a visualization device, such as a camera and/or light source, for visualizing a surgical procedure from a desired position and orientation within a body cavity.

A. Tissue Grasping

1. Actuation Control Mechanism

Generally, the handle (104) comprises an actuation control mechanism that may be manipulated by a user to controllably actuate the grasper (200). In some variations, the delivery device (100) may comprise a separate decoupling control, which a user may use to decouple the grasper (200) from the delivery device (100). In other variations, the delivery device (100) may be configured such that a user may use the actuation control mechanism to decouple the grasper (200) from the delivery device (100) in addition to actuating the grasper (200). For example, in the variation of the delivery device (100) depicted in FIGS. 1A-1C, the handle (104) of delivery device (100) may comprise a grip portion (110) and an actuation control mechanism comprising a trigger (112). While shown in FIGS. 1A-1C as being a trigger (112), it should be appreciated that the actuation control mechanism may comprise any suitable control element (e.g., a slider, a knob, or the like) capable of actuating the grasper (200) as described in more detail below. The trigger (112) may be configured to both actuate the grasper (200) and decouple the grasper (200) from the delivery device (100).

Specifically, in some variations the trigger (112) may be moveable between three positions. While three distinct positions will be discussed below, it should be appreciated that the trigger (112) may also assume one or more intermediate positions between these positions. Of the three positions, the trigger (112) may be moveable between a first position (as shown in FIG. 1A) and a second position (as shown in FIG. 1B) to actuate the grasper (200). Specifically, the grasper (200) may comprise a first jaw (202) and a second jaw (204), and at least one of the first jaw (202) and the second jaw (204) may be configured to rotate relative to the grasper (200). The grasper (200) may be actuated between an open configuration and a closed configuration.

In the open configuration, the first jaw (202) and second jaw (204) may be held in rotationally separated positions to define a space between the first jaw (202) and the second jaw (204), as shown in FIG. 1B. In the closed configuration, the first jaw (202) and second jaw (204) may be rotationally biased toward each other, as shown in FIG. 1A. While the first jaw (202) is shown in FIG. 1A as contacting the second jaw (204) when the grasper (200) is in the closed configuration, it should be appreciated that when the grasper (200) is connected to tissue, tissue positioned between the first jaw (202) and second jaw (204) may prevent the first jaw (202) from contacting the second jaw (204) when the grasper (200) is in the closed configuration.

The grasper (200) may be actuated between the closed and open configurations to releasably connect the grasper (200) to tissue. For example, when the trigger (112) is in the first position (as shown in FIG. 1A), the grasper (200) may be placed in the closed configuration. As the trigger (112) is moved to the second position (as shown in FIG. 1B), the grasper (200) may be moved to the open configuration. In variations where the first jaw (202) is configured to rotate relative to the grasper (200), moving the trigger (112) from the first position to the second position may rotate the first jaw (202) away from the second jaw (204), while moving the trigger (112) from the second position back to the first position may rotate the first jaw (202) toward the second jaw (204). Accordingly, by moving the trigger (112) between the first and second positions, a user may selectively open and close the jaws (202, 204) of the grasper (200) using the delivery device (100). To connect the grasper (200) to tissue, a user may place the trigger (112) in the second position (or an intermediate position between the first and second positions) to open (or partially open) the jaws (202, 204), and may manipulate the delivery device (100) to position tissue between the first jaw (202) and the second jaw (204). With the tissue positioned between the jaws (202, 204), the trigger (112) may be returned to the first position to close the jaws (202, 204) to clamp the jaws (202, 204) against the tissue, thereby releasably connecting the grasper (200) to the tissue.

As mentioned above, the trigger (112) in some variations may be configured to decouple the grasper (200) from the delivery device (100). For example, the trigger (112) may be moved from the first position (as shown in FIG. 1A) to a third position (as shown in FIG. 1C), and the delivery device (100) may be configured to decouple from the grasper (200) when the trigger (112) is moved to the third position (as will be described in more detail below). When the same actuation control mechanism is used to actuate the grasper (200) and decouple the grasper (200) from the delivery device (100), it may be desirable to decouple the grasper (200) from the delivery device (100) when the grasper (200) is in a closed configuration and engaged with tissue. Accordingly, in some variations, the first position of the trigger (112) (which may correspond to a closed configuration of the grasper (200)) may be an intermediate position between the second position and third position. In these variations, when the trigger (112) is placed in the second position to place the grasper (200) in an open configuration, the trigger (112) will move through the first position (which may move the grasper (200) to a closed configuration) before it reaches the third position. Thus the grasper (200) may be moved to the closed configuration before it is decoupled from the delivery device (100).

The delivery devices described here may be configured to actuate, couple to, and decouple from, the graspers described here in any suitable manner. Furthermore, the delivery devices described here may be configured to couple to and decouple from a suitable visualization device (e.g., camera, light source). When decoupling and coupling are described herein with respect to the delivery devices and grasper, it should be appreciated that the same mechanisms and methods may be used for decoupling and coupling the delivery devices and suitable visualization devices. For example, FIGS. 2A-2F illustrate one suitable mechanism by which a delivery device may be configured to actuate and couple/decouple a grasper. For example, FIG. 2A depicts a cross-sectional side view of variations of the grasper (200) and a distal portion of the delivery device (100) each described above with respect to FIGS. 1A-1C. As shown there, the grasper (200) may comprise a first jaw (202), a second jaw (204), and a main body (206). Generally, the first jaw (202) is rotatably connected to the main body (206) at a pivot point (208), such that the first jaw (202) may rotate relative to the main body (206). In some variations (such as that shown in FIGS. 2A-2F), the second jaw (204) may be fixed relative to the main body (206), while in other variations the second jaw (204) may also be rotatably connected to the main body (206). When the second jaw (204) is fixed relative to the main body (206), the second jaw (204) may be formed separately from the main body (206) and subsequently attached thereto, or may be formed integrally with the main body (206). When a jaw as described here is configured to rotate relative to a pivot point, the jaw may be configured to rotate in any suitable manner. In some variations, a jaw (202) may be connected to the main body (206) via a rotation pin (208), such that the jaw (202) may rotate around the rotation pin (208) (or the jaw (202) and rotation pin (208) may rotate relative to the main body (206)). In other variations, the jaw may be connected to the main body via a living hinge.

The first jaw (202) and second jaw (204) may be rotationally biased toward each other (e.g., towards a closed configuration). In variations where the first jaw (202) is rotatably connected to the main body (206), the first jaw (202) may be rotationally biased toward the second jaw (204). For example, in some variations the grasper (200) may comprise a spring such as a torsional spring or a cantilever spring (not shown), which may spring-bias the first jaw (202) toward the second jaw (204). In variations where the second jaw (204) is rotatably connected to the main body (206), the second jaw (204) may also be biased towards the first jaw (202) (e.g., via one or more springs). The bias of the jaws (202, 204) toward the closed configuration may act to hold tissue positioned between the first jaw (202) and the second jaw (204).

As shown in FIG. 2A, the main body (206) of the grasper (200) may comprise a barrel portion (210) with a lumen (212) extending therethrough. A portion of the delivery device (100) may be advanced through the lumen (212) to rotate first jaw (202) (and in some instances, the second jaw (204) in variations where the second jaw (204) is rotatably connected to the main body (206)) relative to the main body (206), as will be described in more detail below. In some variations, the lumen (212) may have a constant diameter. In other variations, different portions of the lumen (212) may have different diameters.

For example, in the variation of the grasper (200) shown in FIGS. 2A-2F, the lumen (212) of the barrel portion (210) may comprise a proximal segment (214), a distal segment (216), and an intermediate segment (218) positioned between the proximal segment (214) and the distal segment (216). As shown in FIG. 2A, the proximal segment (214) may have a larger diameter than the distal segment (216), and the intermediate segment (218) may have a larger diameter than both the proximal segment (214) and the distal segment (216). The proximal (214), distal (216), and intermediate (218) segments may aid in maintaining a coupling with the delivery device (100), as will be described in more detail below.

The barrel portion (210) of the grasper (200) may be sized and configured to be engaged by the distal engagement portion (108) of the delivery device (100) to releasably couple the grasper (200) to the delivery device (100). In some variations, the outer diameter of the barrel portion (210) may have a constant diameter, or may have different portions of the barrel portion (210) having different diameters, such as described in more detail below. Turning to the delivery device (100), in the variation of the delivery device shown in FIGS. 2A-2F, the delivery device (100) may comprise an actuation rod (114) slidably disposed in the shaft (106). The actuation rod (114) may be advanced through the lumen (212) of the barrel portion (210) of the grasper (200) to actuate the grasper (200), as will be described in more detail below. Also shown in FIG. 2A is a locking sheath (116), a coupling magnet (118), and a spring (120). Each of these components will be discussed further below.

While shown in FIGS. 2A-2F as having a coupling magnet (118), the delivery device (100) need not comprise a coupling magnet. In variations of the delivery device (100) that do comprise a coupling magnet (118), the coupling magnet (118) may be slidably housed in a housing of the distal engagement portion (108), and may be configured to releasably couple the delivery device (100) to the grasper (200). The coupling magnet (118) may be movable between an advanced position (as depicted in FIG. 2A) and a retracted position (as depicted in FIG. 2C). In variations where the delivery device (100) comprises a spring (120), the spring (120) may be positioned in the distal engagement portion (108) to bias the coupling magnet (118) toward the advanced position.

The delivery device (100) may be configured to couple to the grasper (200) when the coupling magnet (118) is in the advanced position. For example, when the distal engagement portion (108) is brought near the grasper (200), the coupling magnet (118) may attract the grasper (200). Generally, at least a portion of the graspers described here are formed from one or more materials that may be attracted to a magnetic field. The materials may include one or more permanent magnets, or one or more ferromagnetic or ferrimagnetic materials, such as, for example, stainless steel, iron, cobalt, nickel, neodymium iron boron, samarium cobalt, alnico, ceramic ferrite, alloys thereof and/or combinations thereof. The particular configuration of the materials within the grasper—for example, the type, amount, polarity, and location of the materials—may alter how the grasper responds to and/or interacts with a control element, and is discussed in more detail below.

Accordingly, one or more portions of the grasper (200) may be formed from or otherwise include a material that may be attracted to a magnetic field produced by the coupling magnet (118). The attractive force provided by the coupling magnet (118) may hold the grasper (200) against or at least partially within the distal engagement portion (108), such as shown in FIG. 2B. The grasper (200) may be positioned such that a proximal end of the barrel portion (210) of the grasper (200) is held against or at least partially within the distal engagement portion (108) of the delivery device (100).

To decouple the grasper (200) from the distal engagement portion (108), the coupling magnet (118) may be withdrawn to the retracted position, as shown in FIG. 2C. Because the attractive force applied by a magnet decreases as a function of the distance from the magnet, moving the coupling magnet (118) to the retracted position (e.g., by an actuation control mechanism) may increase the distance between the grasper (200) and the coupling magnet (118) (e.g., the distal engagement portion (108) may comprise a stop (121) which may prevent the grasper (200) from being retracted with the coupling magnet (118)), which may reduce the attractive force applied to the grasper (200). Eventually, the attractive force may be sufficiently diminished such that the grasper (200) may decouple from the delivery device (100).

Nevertheless, the coupling magnet (118) may be retracted in any suitable manner. In some variations, the delivery device (100) may comprise a control sheath (not shown) which may be attached to the coupling magnet (118). The control sheath may be selectively withdrawn or advanced from the grasper (200) (e.g., via a control mechanism in the handle (104)) to withdraw and advance, respectively, the coupling magnet (118). In other variations, a portion of the actuation rod (114) may be configured to retract the coupling magnet (118). For example, the actuation rod (114) may be configured to catch on or otherwise engage the coupling magnet (118) during retraction of the actuation rod (114). In these variations, the actuation rod (114) may be withdrawn until the actuation rod (114) engages the coupling magnet (118). Once the actuation rod (114) engages the coupling magnet (118), further withdrawal of the actuation rod (114) may also withdraw the coupling magnet (118).

For example, as shown in FIGS. 2A-2F, the actuation rod (114) may be slidably disposed within a lumen (122) of the coupling magnet (118). In some variations, at least a segment of the actuation rod (114) may be sized and configured such that the portion of the actuation rod (114) cannot fully pass through the lumen (122). For example, in some variations a segment of the actuation rod (114) may have a diameter greater than a diameter of the lumen (122). Additionally or alternatively, the segment may comprise one or more projections extending from an outer surface of the actuation rod (114) and which cannot fully pass through the lumen (122). When the segment of the actuation rod (114) is positioned distal to the coupling magnet (118), the actuation rod (114) may be freely advanced relative to the coupling magnet (118). Conversely, withdrawal of the actuation rod (114) may pull the segment of the actuation rod (114) into contact with the coupling magnet (118). Since the segment cannot fully pass through the lumen (122) of the coupling magnet (118), further withdrawal of the actuation rod (114) may cause the segment of the actuation rod (114) to pull on and withdraw the coupling magnet (118). When the actuation rod (114) is subsequently advanced, the spring (120) may advance the coupling magnet (118) with the actuation rod (114) until the coupling magnet (118) reaches the advanced position.

In variations where the delivery device (100) comprises a locking sheath (116) slidably disposed in the lumen (122) of the coupling magnet (118), the locking sheath (116) may be configured to withdraw the coupling magnet (118). For example, a segment of the locking sheath (116) may be sized and configured such that the segment cannot fully pass through the lumen (122) of the coupling magnet (118), such as described above with respect to the actuation rod (114). In the variation shown in FIGS. 2A-2F, the locking sheath (116) may comprise a protrusion (124) positioned distally of the coupling magnet (118) and sized such that the protrusion (124) cannot fully pass through the lumen (122). In these variations, proximal withdrawal of the locking sheath (116) through the lumen (122) may place the protrusion (124) into contact with the coupling magnet (118), such as shown in FIGS. 2A and 2B. As depicted in FIG. 2C, further withdrawal of the locking sheath (116) may also withdraw the coupling magnet (118) (e.g., by virtue of the contact between the protrusion (124) and the coupling magnet (118)).

As mentioned above, the delivery devices described here may comprise a locking sheath (although it should be appreciated that in some variations the delivery device may not comprise a locking sheath). In variations where the delivery device does comprise a locking sheath (116), such as the variation of the delivery device (100) depicted in FIGS. 2A-2F, the locking sheath (116) may be slidably disposed in the shaft (106). The actuation rod (114) may in turn be positioned at least partially within the locking sheath (116). The locking sheath (116) may comprise an expandable distal portion (126) which may be configured to expand inside of the lumen (212) of the barrel portion (210) of the grasper (200) to temporarily engage an interior portion of the lumen (212), which may help maintain the coupling between the grasper (200) and the delivery device (100).

In these variations, the delivery device (100) may be configured such that advancement of the actuation rod (114) relative to the locking sheath (116) may expand the expandable distal portion (126) of the locking sheath (116). For example, the expandable distal portion (126) of the locking sheath (116) may comprise at least one internal projection (128) that projects inwardly and is sized and shaped to fit within at least one corresponding indentation (130) in the outer surface of the actuation rod (114). It should be appreciated that at least one internal projection (128) may be a single projection (e.g., an annular snap-fit or a projection that extends radially around some or all of the inner circumference of the locking sheath (116)) or multiple discrete projections. Similarly, the actuation rod (114) may comprise a single indentation (e.g., an indentation that extends radially around some or all of the outer surface of actuation rod (114)) or multiple indentations.

The actuation rod (114) may be positioned within the locking sheath (116) such that the internal projections (128) of the locking sheath (116) are positioned in corresponding indentations (130) of the actuation rod (114), such as shown in FIGS. 2A-2D. This may create a friction fit or mechanical interlock between the actuation rod (114) and the locking, sheath (116), which may cause the locking sheath (116) to be advanced and withdrawn with the actuation rod (114).

The engagement between the actuation rod (114) and the locking sheath (116) may be further configured such that under certain circumstances the actuation rod (114) may be advanced relative to the locking sheath (116) to expand the expandable distal portion (126) of the locking sheath (116). For example, as shown in FIGS. 2A-2F, the internal projections (128) of the locking sheath (116) and the corresponding indentations (130) of the actuation rod (114) may each have a ramped proximal portion. When the internal projections (128) are positioned within corresponding indentations (130), the ramped proximal portion of each internal projection (128) may be positioned in contact with the ramped proximal portion of a corresponding indentation (130). This contact may provide the friction fit or mechanical interlock that may allow the actuation rod (114) to distally advance the locking sheath (116) as mentioned above.

When an external force is applied to the locking sheath (116) to resist distal advancement of the locking sheath (116), advancement of the actuation rod (114) may overcome the friction force or mechanical connection between the ramped proximal portions of the internal projections (128) and the corresponding indentations (130), at which point the contacting ramped surfaces may slide relative to each other as the actuation rod (114) begins to advance distally relative to the locking sheath (116). As the actuation rod (114) is advanced distally relative to the locking sheath (116), the internal projections (128) may slide out of their corresponding indentations (130) (such as shown in FIG. 2E), which may thereby expand the expandable distal portion (126) of the locking sheath (116).

This expansion of the expandable distal portion (126) of the locking sheath (116) may help to maintain the temporary coupling between the delivery device (100) and the grasper (202), as illustrated in FIGS. 2D-2F. Specifically, the kicking sheath (116) and actuation rod (114) may be positioned such that the internal projections (128) of the locking sheath (116) are positioned in respective indentations (130) on the actuation rod (114), which may allow advancement and retraction of the actuation rod (114) to advance and retract the locking sheath (116), as discussed above. The grasper (200) may be coupled to the distal engagement portion (108) of the delivery device (100), as shown in FIG. 2C, and the actuation rod (114) may be advanced to begin advancing the actuation rod (114) and locking sheath (116) into the lumen (212) of the barrel portion (210) of the grasper (200). The actuation rod (114) may be sized such that it is smaller than each of the proximal segment (214), the distal segment (216), and the intermediate segment (218) of the lumen (212) of the barrel portion (210) of the grasper (200). This may allow the actuation rod (114) to be advanced through the entire lumen (212) of the barrel portion (210). The locking sheath (116), however, may be sized and configured such that it may pass through the proximal segment (214) and the intermediate segment (218) of the lumen (212), but is prevented from entering the distal segment (216). Accordingly, the actuation rod (114) may be advanced to advance the actuation rod (114) and the locking sheath (116) through the lumen (212) of the barrel portion (210) of the grasper (200) until the locking sheath (116) reaches the distal segment (216) of the lumen (212), as shown in FIG. 2D. At this point, the locking sheath (116) may be prevented from entering the distal segment (216), and may thus be prevented from further advancement.

The actuation rod (114) may be further advanced relative to the grasper (200) to advance the actuation rod (114) through the distal segment (216) of the lumen (212). Because the locking sheath (116) is prevented from advancing further, the actuation rod (114) may be advanced relative to the locking sheath (116). This may cause the internal projections (128) of the locking sheath (116) to slide out of their respective indentations (130) and expand the expandable distal portion (126) of the locking sheath (116), as depicted in FIG. 2E. Specifically, the expandable distal portion (126) may be positioned in the intermediate segment (118) of the lumen (112) when it is expanded.

When expanded, the expandable distal portion (126) may be configured to resist being removed from the lumen (212) of the barrel portion (210) of the grasper (200). Specifically, the expandable distal portion (126) of the locking sheath (116) may be sized and configured such that, when expanded, the expandable distal portion (126) may be prevented from passing through the proximal segment (214) of the lumen (212) (e.g., the outer diameter of the expanded distal portion (126) may be larger than the diameter of the proximal segment (214) of the lumen (212)). When the expandable distal portion (126) of the locking sheath (116) is expanded in the intermediate segment (218) (as shown in FIG. 2E), the locking sheath (116) may resist both advancement of the locking sheath (116) into the distal segment (216) (as discussed above) and withdrawal of the locking sheath (116) though the proximal segment (214) of the lumen (212). Accordingly, the expanded locking sheath (116) may lock the grasper (200) in place relative to the delivery device (100).

When the actuation rod (114) is further advanced to actuate the jaws (202, 204) of the grasper (200) (as shown in FIG. 2F, and discussed in more detail below), the actuation rod (114) may apply one or more forces to the grasper (200) which may have a tendency to push the grasper (200) away from the coupling magnet (118) (which in some instances could possibly inadvertently decouple the grasper (200) from the delivery device (100)), but the engagement between the expanded locking sheath (116) and the grasper (200) may overcome these forces to maintain the position of the grasper (200) relative to the delivery device (100).

To disengage the locking sheath (116) from the grasper (200), the actuation rod (114) may be retracted until the indentations (130) of the actuation rod (114) reach the internal projections (128) of the locking sheath (116). The expandable distal portion (126) of the locking sheath (116) may be biased toward an unexpanded state such that the internal projections (128) reposition themselves into their respective indentations (130), as shown in FIG. 2D. The actuation rod (114) may then be withdrawn to withdraw the locking sheath (116) (e.g., by virtue of the connection between the indentations (130) and the internal projections (128)).

The grasper (200) may be configured to be actuated in any suitable manner. In some variations, the grasper (200) may be configured such that it may be actuated by a force applied internally of the grasper (200) (e.g., via an actuation rod (114) of the delivery device (100) advanced through the lumen (212) of the barrel portion (210) of the grasper (200), as discussed in more detail below), and may be further configured such that it may be actuated by a force applied externally of a grasper (200) (e.g., via a grasping device). For example, in the variation of the grasper (200) shown in FIGS. 2A-2F, the grasper (200) may comprise a proximal arm (220) connected to the first jaw (202), wherein rotation of the proximal arm (220) rotates the first jaw (202) relative to the main body (206) and second jaw (204) of the grasper (200). The proximal arm (220) may act as a lever and/or a cam to rotate the first jaw (202).

For example, in some instances the proximal arm (220) may act as a cam to rotate the first jaw (202). In these instances, the actuation rod (114) of the delivery device (100) may rotate the first jaw (202). Specifically, a portion of the proximal arm (220) may be aligned relative to the lumen (212) such that advancement of the actuation rod (114) through the lumen (212) pushes the actuation rod (114) into contact with the proximal arm (220), as illustrated in FIG. 2E. Once in contact with the proximal arm (220), advancement of the actuation rod (114) may push against the proximal arm (220). The proximal arm (220) may act as a cam to convert the linear motion of the actuation rod (114) into rotation of the proximal arm (220), which may in turn rotate the first jaw (202) away from the second jaw (204) as shown in FIG. 2F. When the first jaw (202) is spring-biased toward the second jaw (204), the rotation of the proximal arm (220) may overcome this spring bias, which may allow the actuation rod (114) to hold the first jaw (202) in its open position. Additionally, the first jaw (202) may rotate back toward the second jaw (204) when the actuation rod (114) is retracted.

Additionally, in the variation of the grasper (200) shown in FIGS. 2A-2F, at least a portion of the proximal arm (220) may be exposed relative to the main body (206), which may allow a grasping device to grasp the proximal arm (220) to rotate the first jaw (202) relative to the second jaw (204). For example, opposing forces (represented by arrows (222) in FIG. 2A) may be applied (e.g., via a grasping device) to the exposed portion of the proximal arm (220) and the main body (206) to cause the proximal arm (220) to rotate around the pivot point (208) (which may in turn rotate the first jaw (202) away from the second jaw (204)).

Figure 3A:
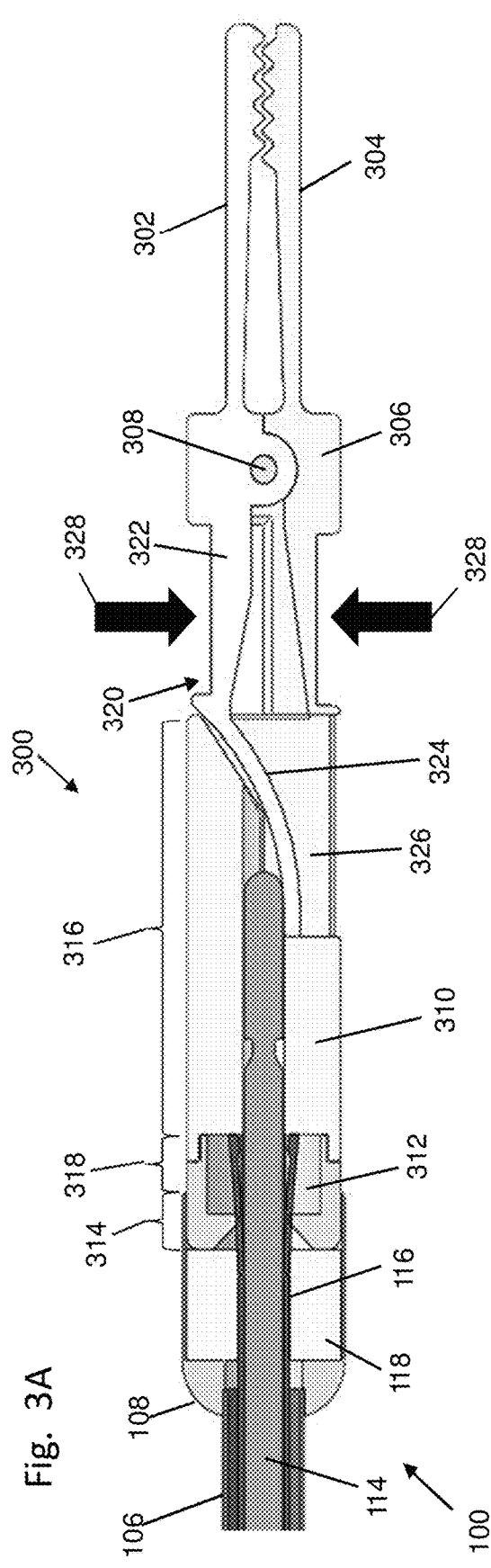
Figure 3B:
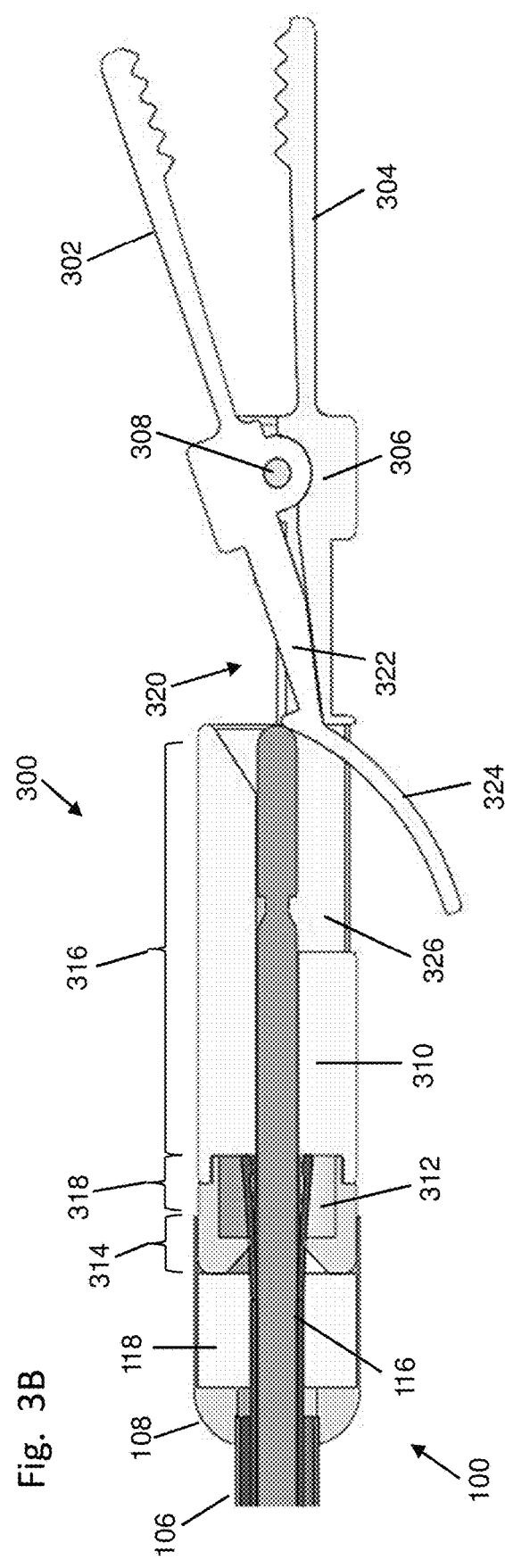

While the proximal arm (220) is shown in FIGS. 2A-2F as being curved, it should be appreciated that in some variations the graspers described here may also comprise one or more straight segments. For example, FIGS. 3A and 3B depict cross-sectional side views of one such variation of a grasper (300) which may be used with the systems described here. As shown there, the grasper (300) may comprise a first jaw (302), a second jaw (304), and a main body (306). The first jaw (302) may be rotatably coupled to the main body (306) at a pivot point (308), and the main body (306) of the grasper (300) may comprise a barrel portion (310) having a lumen (312) extending therethrough. In some variations, the lumen (312) may comprise a proximal segment (314), a distal segment (316), and an intermediate segment (318), which may be configured as described above with respect to the variation of the grasper (200) depicted in FIGS. 2A-2F.

As shown in FIGS. 3A and 3B, the grasper (300) may comprise a proximal arm (320) connected to or otherwise extending from the first jaw (302) such that rotation of the proximal arm (320) around the pivot point (308) also rotates the first jaw (302) around the pivot point. In this variation, the proximal arm (320) may comprise a straight segment (322) and a curved segment (324), and the proximal arm (320) may act as a cam and/or lever to rotate the first jaw (302). Specifically, the straight segment (322) may be positioned between the curved segment (324) and the first jaw (302), and may provide a flat surface which may facilitate engagement of the proximal arm (320) by a grasping device. For example, as shown in FIGS. 3A and 3B, at least a portion of the straight segment (322) may be exposed from the main body (306). Some or all of the curved segment (324) may also be exposed, although in some variations, the curved segment (324) may be at least partially positioned within a channel (326) in the barrel portion (310) of the grasper (300).

Opposing forces (represented in FIG. 3A by arrows (328)) may be applied (e.g., via a grasping device) to an exposed portion of the straight segment (322) (and/or an exposed portion of the curved segment (324), when at least a portion of the curved segment (324) is exposed) and the main body (306), which may cause the proximal arm (320) to act as a lever to rotate around the pivot point (308). This in turn may rotate the first jaw (302) away from the second jaw (304), as illustrated in FIG. 3B. When the first jaw (302) is configured to be rotatably biased toward the second jaw (304) (e.g., via one or more springs, as described in more detail above), and the forces (328) holding the first jaw (302) rotated away from the second jaw (304) are removed from the proximal arm (320) and the main body (306), the first jaw (302) may rotate back toward the second jaw (304), as illustrated in FIG. 3A. When tissue is positioned between the first jaw (302) and the second jaw (304), this may connect the grasper (300) to the tissue as discussed in more detail above.

Additionally, a delivery device (such as the delivery device (100) described above with respect to FIGS. 1A-1C and 2A-2F) may be configured to actuate the jaws of the grasper (300) through the barrel portion (310), as illustrated in FIGS. 3A and 3B. The distal engagement portion (108) of the delivery device (100) may engage the barrel portion (310) of the grasper (300) (as discussed in more detail above), and the actuation rod (114) may be advanced through the lumen (312) of the barrel portion (310) until the actuation rod (114) contacts the curved segment (324) of the proximal arm (320), such as shown in FIG. 3A. In some instances, advancing the actuation rod (114) to this point may cause a locking sheath (116) of the delivery device (100) to couple to the lumen (312) of the barrel portion (310) of the grasper (300), such as described in more detail above.

Further advancement of the actuation rod (114) may push the actuation rod (114) against the curved segment (324) of the proximal arm (320), and the proximal arm (320) may act as a cam to convert the linear movement of the actuation rod (114) into rotational movement of the proximal arm (320). As the actuation rod (114) rotates the proximal arm (320), the first jaw (302) may rotate away from the second jaw (304), as depicted in FIG. 3B. When the actuation rod (114) is withdrawn, the first jaw (302) may be biased to rotate toward the second jaw (304) to return the first jaw (302) toward the second jaw (304). Accordingly, the actuation rod (114) may be advanced and withdrawn to cause the first jaw (302) to rotate away from and toward, respectively, the second jaw (304).

Additionally, positioning the straight segment (322) between the curved segment (324) and the pivot point (308) may create a longer moment arm, which may reduce the force that must be applied to the curved segment (324) by the actuation rod (104) in order to rotate the first jaw (302). While the proximal arm (320) shown in FIGS. 3A and 3B is configured such that a concave portion of the curved segment (324) faces the lumen (312) such that the actuation rod (114) contacts the concave portion of the curved segment (324) during advancement of the actuation rod (114), the curved segment may instead be configured such that a convex portion of a curved segment faces the lumen such that the actuation rod (114) contacts the convex portion of the curved segment during advancement of the actuation rod (114).

While the variations of the graspers depicted in FIGS. 2A-2F and 3A-3B each comprise a proximal arm that is configured to be used as both a cam and a lever to actuate the grasper, in some variations the grasper may comprise a first mechanism which may act as a cam to actuate the grasper and a second mechanism which may act as a lever to actuate the grasper. For example, FIGS. 4A and 4B depict one such variation of a grasper (400) suitable for use with the systems described here. As shown there, the grasper (400) may comprise a first jaw (402), a second jaw (404), and a main body (406). The first jaw (402) may be rotatably coupled to the main body (406) at a pivot point (408), and the main body (406) of the grasper (400) may comprise a barrel portion (410) having a lumen (412) extending therethrough. In some variations, the lumen (412) may comprise a proximal segment (414), a distal segment (416), and an intermediate portion (418), which may be configured as described above with respect to the variation of the grasper (200) depicted in FIGS. 2A-2F.

Also shown in FIGS. 4A and 4B are a proximal arm (420) and an eccentric cam member (422). Each of the proximal arm (420) and the eccentric cam member (422) may be attached to the first jaw (402), such that rotation of either the proximal arm (420) or the eccentric cam member (422) relative to the pivot point (408) may rotate the first jaw (402). For example, opposing forces (represented by arrows (428)) may be applied to the main body (406) and the proximal arm (420), which may rotate the proximal arm (420) relative to the main body (406) and act as a lever to rotate the first jaw (402) away from the second jaw (404), such as shown in FIG. 4B. In some variations, the first jaw (402) may be rotatably biased toward the second jaw (404) (e.g., via one or more springs, as described in more detail above), such that when the forces (428) are removed from the proximal arm (420) and/or main body (406), the first jaw (402) may rotate back toward the second jaw (404), as illustrated in FIG. 4A.

Similarly, the eccentric cam member (422) may be rotated via a portion of a delivery device that may be advanced through the lumen (412) of the barrel portion (410) of the grasper (400). In some instances, the delivery device (100) described above may actuate the grasper (400). The distal engagement portion (108) of the delivery device (100) may engage the barrel portion (410) of the grasper (400) (as discussed in more detail above), and the actuation rod (114) may be advanced through the lumen (412) of the barrel portion (410) until the actuation rod (114) contacts the eccentric cam member (422) (which may be aligned with the lumen (412)), such as shown in FIG. 4A. In some instances, advancing the actuation rod (114) to this point may cause a locking sheath (116) of the delivery device (100) to couple to the lumen (412) of the barrel portion (410) of the grasper (400), such as described in more detail above.

Further advancement of the actuation rod (114) may push against the eccentric cam member (422), which may convert the linear movement of the actuation rod (114) into rotational movement of the eccentric cam member (422). As the actuation rod (114) rotates the eccentric cam member (422), the first jaw (402) may rotate away from the second jaw (404), as depicted in FIG. 4B. When the actuation rod (114) is withdrawn, the first jaw (402) may be biased to rotate back toward the second jaw (404). Accordingly, the actuation rod (114) may be advanced and withdrawn to cause the first jaw (402) to rotate away from and toward, respectively, the second jaw (404).

Returning to FIGS. 2K-2F, the actuation rod (114) may be advanced and withdrawn in any suitable manner. For example, when the delivery device (100) comprises an actuation control mechanism, such as a slider, knob, trigger, or the like, the actuation control mechanism may be operatively connected to the actuation rod (114) such that the actuation control mechanism may advance and withdraw the actuation rod (114). For example, in the variation of the delivery device (100) shown in FIGS. 1A-1C, the trigger (112) may be configured to advance and retract the actuation rod (114). In some of these variations, the trigger (112) may be configured such that rotation of the trigger (112) toward the grip portion (110) withdraws the actuation rod (114) relative to the shaft (106), while rotation of the trigger (112) away from the grip portion (110) advances the actuation rod (105) relative to the shaft.

In these variations, when the trigger (110) is in the first position (as shown in FIG. 1A), the actuation rod (114) may be positioned as shown in FIGS. 2A and 2B with the coupling magnet (118) in an advanced position, which may allow the distal engagement portion (108) to connect to a grasper (such as grasper (200), as illustrated in FIGS. 1A and 2B). The trigger (112) may be rotated toward the grip portion (110) to position the trigger (112) in the third position (as shown in FIG. 1C), and this rotation may retract the actuation rod (114) relative to the shaft (106). Retraction of the actuation rod (114) may also withdraw the coupling magnet (118) to a retracted position, such as illustrated in FIG. 2C, which may decouple a grasper from the delivery device (100) as described above. The trigger (112) may be rotated away from the grip portion (110) and back to the first position to advance the actuation rod (114) back to the position shown in FIGS. 2A and 2B.

Further rotation of the trigger (112) away from the grip portion (110) may move the trigger (112) from the first position to the second position (as shown in FIG. 1B) and may advance the actuation rod (114) through a lumen of a barrel portion of a grasper (e.g., the lumen (212) of the barrel portion (210) of the grasper (200) described above) to rotate one or more jaws of the grasper (as shown in FIG. 2F). Returning the trigger (112) to the first position (e.g., by rotating the trigger (112) toward the grip portion (110)) may withdraw the actuation rod (114) relative to the shaft (106) and the grasper, which may allow the grasper to return to a closed configuration. It should be appreciated that in some variations, rotation of the trigger (112) toward the grip portion (110) may be configured to advance the actuation rod (114) relative to the shaft (106), while rotation of the trigger (112) away from the grip portion (110) may retract the actuation rod (114) relative to the shaft (106).

Figure 6A:
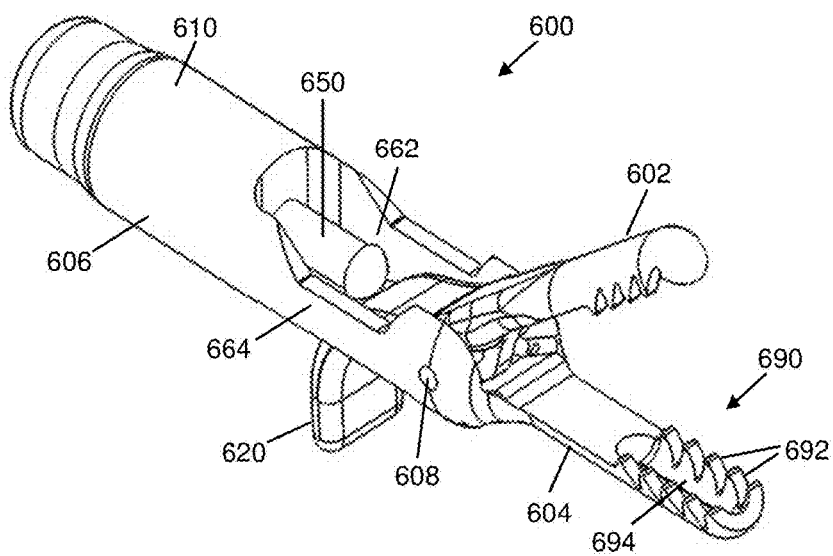
FIGS. 6A and 6B show perspective and side views, respectively, of an illustrative variation of a grasper as described here.
Figure 6B:
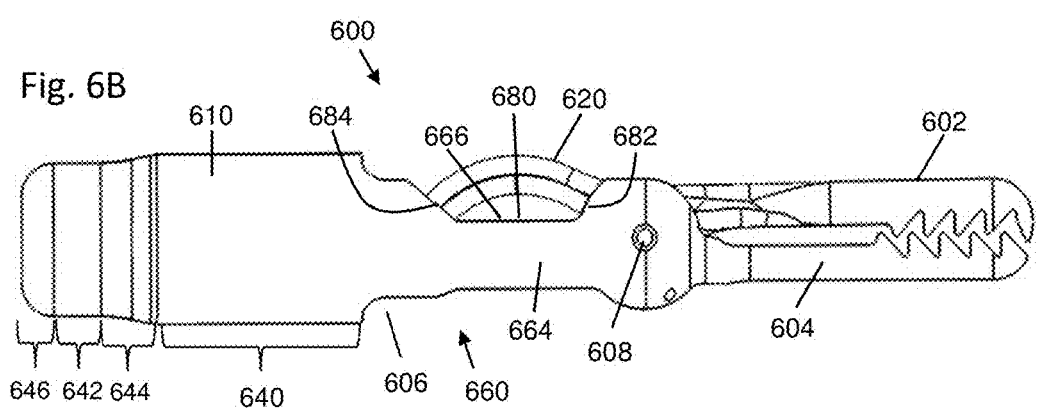
Figure 6C:
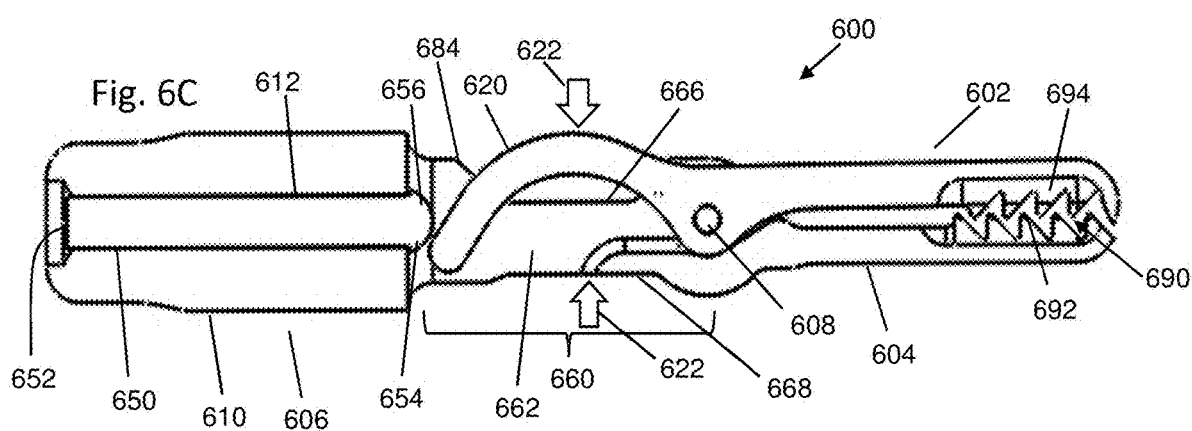
FIG. 6C shows a cross-sectional side view of the grasper of FIGS. 6A and 6B.

FIGS. 6A-6C depict another variation of a grasper (600) as described here. Specifically, FIGS. 6A and 6B show perspective and side views, respectively, of the grasper (600). As shown there, the grasper (600) may comprise a first jaw (602), a second jaw (604), and a main body (606). Generally, the first jaw (602) may be rotatably connected to the main body (606) at a pivot point (608), such that the first jaw (602) may rotate relative to the main body (606). While the second jaw (604) is shown in FIGS. 6A-6C as being fixed relative to the main body (606), it should be appreciated that in some variations the second jaw (604) may be rotatably connected to the main body (606), such as discussed in more detail above. The first jaw (602) (and/or the second jaw (604) in variations where the second jaw (604) is rotatably connected to the main body (606)) may be rotated relative to the main body (606) to actuate the grasper (600) between an open configuration and a closed configuration.

Specifically, in the open configuration, the first jaw (602) and the second jaw (604) may be held in rotationally separated positions to define a space between the first jaw (602) and the second jaw (604), as shown in FIG. 6A. In the closed configuration, the first jaw (602) and second jaw (604) may be rotationally biased toward each other, as shown in FIG. 6B. While the first jaw (602) is shown as contacting the second jaw (604) in FIG. 6B, it should be appreciated that when the grasper (600) is connected to tissue, tissue positioned between the first jaw (602) and the second jaw (604) may prevent the first jaw (602) from contacting the second jaw (604) when the grasper is in the closed configuration. The first jaw (602) and second jaw (604) may be rotationally biased toward a closed configuration in any suitable manner (e.g., via a torsional spring (not shown)), such as described in more detail above.

The main body (606) of the grasper (600) may comprise a barrel portion (610) with a lumen (612) extending therethrough. A portion of a delivery device may be advanced at least partially into the lumen (612) to actuate the grasper (600) between closed and an open configurations, as will be discussed in more detail below. The outer diameter of the barrel portion (610) may be uniform, or may vary along the length of the barrel portion (610). For example, in the variation of the grasper (600) shown in FIGS. 6A-6C, the barrel portion (610) may have a first segment (640) having a first outer diameter and a second segment (642) having a second outer diameter. In some variations, the first outer diameter may be greater than the second outer diameter, which may allow the first segment (640) to act as a stop when engaged by a delivery device, such as discussed in more detail herein. For example, in some variations the first segment may have a first outer diameter of about 10 mm, and the second segment may have an outer diameter between about 7 mm and about 9 mm.

In some variations (such as the variation of grasper (600) illustrated in FIGS. 6A-6C), the barrel portion (610) may further comprise a tapered portion (644) positioned between the first segment (640) and the second segment (642), such that the outer diameter of the tapered segment (644) tapers between the first outer diameter and the second outer diameter. It should be appreciated, however, that the barrel portion (610) need not have such a tapered portion (644), and the first segment (640) may immediately transition to the second segment (642). In variations that do include a tapered segment (644), the tapered segment (644) may provide a gradual diameter transition between the first (640) and second (642) segments, which may in turn reduce the presence of edges that may catch on or otherwise disturb tissue during use of the grasper (600).

Additionally or alternatively, the barrel portion (610) may have a tapered segment (646) at a proximal end of the barrel portion (610), which may also be at a proximal end of the first segment (640). In these variations, the diameter of the tapered segment (646) may taper from the first outer diameter of the first segment (640) to a third outer diameter smaller than that of the first outer diameter. In variations that include a tapered segment (646) at a proximal end of the barrel portion (610), the tapered diameter may facilitate alignment of the barrel portion (610) with a portion of the delivery device. Specifically, when a proximal end of the barrel portion (610) is inserted into a portion of a delivery device (as described in more detail below), the tapered segment (646) may help guide the barrel portion (610) into the delivery device, which may be beneficial in instances where the delivery device (or another retrieval device) is connected to the grasper to retrieve the grasper.

The first jaw (602) may be configured to rotate in any suitable manner such as described above. For example, in the variation of the grasper (600) shown in FIGS. 6A-6C, the grasper (600) may comprise a proximal arm (620) connected to the first jaw (602) such that rotation of the proximal arm (620) relative to the pivot point (608) rotates the first jaw (602) relative to the pivot point (608) (which may also rotate the first jaw (602) relative to the main body (606) and/or the second jaw (604)). While the proximal arm (620) shown in FIGS. 6A-6C may comprise a curved arm (620) that may be configured to act as both a cam and a lever (similar to the proximal arm (220) of the grasper (200) discussed above with respect to FIGS. 1A-1C and 2A-2F), it should be appreciated that the grasper may include any of the proximal arms and/or eccentric cam members discussed above with respect to FIGS. 3A-3B and 4A-4B. The proximal arm (620) (and/or an eccentric cam member) may assist in actuation of the grasper (600), as described hereinthroughout.

Generally, at least a portion of the proximal arm (620) may be exposed relative to the main body (606), which may allow a grasping device to grasp the proximal arm (620) to rotate the first jaw (602) relative to the second jaw (604), as will be discussed in more detail below. Specifically, the main body (606) may comprise a barrel extension (660) between the barrel portion (610) and the pivot point (608). As shown in a cross-sectional side view in FIG. 6C, the barrel extension (660) may comprise a channel (662) extending at least partially through the barrel extension (660). In the variation shown in FIGS. 6A-6C, the channel (662) may extend entirely through the barrel extension (660). The barrel extension (660) may have a wall (664) on one or both sides of the channel (662). In the variation shown in FIGS. 6A-6C, the barrel extension (660) may have a wall (664) on each side of the channel (662). The proximal arm (620) may be positioned at least partially within the channel (662), and may be configured to rotate through the channel (662) as the grasper (600) is actuated between open and closed configurations.

Generally, each wall (664) of the barrel extension (660) may have a top edge (666) and a bottom edge (668). The top edge (666) and bottom edge (668) may have any suitable profile, and together may define a height of the wall (664). For example, in the variation shown in FIGS. 6A-6C, the bottom edge (668) may be linear and substantially parallel to a longitudinal axis, while the top edge (666) may include a linear portion (680) positioned between two ramped segments (labeled (682) and (684)). In these variations, the height of the walls (664) may decrease along each of the ramped segments (682) and (684) toward the linear portion (680). This may facilitate grasping of the grasper (600) with a grasping device, as will be described in more detail below. In other variations, the top edge (666) and/or the bottom edge (668) may have a curved profile.

In some variations, the graspers described here may comprise a shuttle pin at least partially positioned in a lumen of the barrel portion of the grasper. Generally, the shuttle pin may reduce the distance an actuation rod may need to be inserted into the barrel portion in order to actuate the grasper. For example, in the variation of the grasper (600) shown in FIG. 6C, the grasper (600) may further comprise a shuttle pin (650). The shuttle pin (650) may be positioned at least partially within the lumen (612) of the barrel portion (610) of the grasper (600) and may be configured to slide relative to the lumen (612). The shuttle pin (650) may have a proximal end (652) and a distal end (654), and may assist in actuation of the grasper (600). Specifically, advancement of a portion of a delivery device (e.g., an actuation rod) into the lumen (612) of the barrel portion (610) may cause the delivery device to contact the proximal end (652) of the shuttle pin (650) and advance the shuttle pin (650) relative to the lumen (612). As the shuttle pin (650) is advanced relative to the lumen (612) of the barrel portion (610), the distal end (654) of the shuttle pin (650) may press against the proximal arm (620) (or an eccentric cam member, in variations where the grasper includes an eccentric cam member), which may cause the proximal arm (620) to act as a cam member, such as discussed in more detail above.

Without the shuttle pin (650), an actuation rod may otherwise need to be inserted into the barrel portion (610) until it contacts the proximal arm (620) directly, such as discussed above. When the delivery device is withdrawn relative to the shuttle pin (650), the return bias of the first jaw (202) toward a closed configuration may push the shuttle pin (650) proximally relative to the lumen (612) of the barrel portion (610). While the variations of the graspers discussed above with respect to FIGS. 2A-2F, 3A, 3B, 4A, and 4B are not depicted as having a shuttle pin, it should be appreciated that any of these graspers may comprise a shuttle pin, which may be configured in any suitable manner as discussed with respect to shuttle pin (650) of the grasper (600) shown in FIGS. 6A-6C.

In variations where the graspers described here comprise a shuttle pin, the grasper may be configured to help prevent the shuttle pin from disengaging from the grasper. In some variations, at least a portion of a shuttle pin may be configured to have an outer profile that is larger than at least a portion of the lumen of the barrel portion of a main body. For example, in the variation of the shuttle pin (650) shown in FIG. 6C, the distal end (654) may comprise a cap (656) that may have an outer diameter sized to be larger than the lumen (612) of the barrel portion (610) of the main body (606). The shuttle pin (650) may be positioned in the lumen (612) such that the cap (656) is positioned distally of the lumen (612). Because the cap (656) is sized larger than the lumen (612), it may be prevented from entering the lumen (612) as the shuttle pin (650) is slid proximally relative to the barrel portion (610). Accordingly, the shuttle pin (650) may slide proximally until the cap (656) contacts the barrel portion (610), at which point the cap (656) may act as a stop to prevent further proximal movement of the shuttle pin (650). This may prevent the shuttle pin (650) from sliding out of the proximal end of the barrel portion (610) and disengaging the grasper (600).

Additionally, the grasper (600) may be configured to limit the amount of distal advancement of the shuttle pin (650). Generally, a portion of a proximal arm or an eccentric cam member (e.g., the proximal arm (620) of grasper (600)) may be aligned with the lumen of the barrel portion, which may resist or stop forward advancement of the shuttle pin (650) due to gravitational forces. When a delivery device or other device is used to advance the shuttle pin (650) to rotate the proximal arm and/or eccentric cam member, the delivery device and/or grasper may be configured to limit advancement of the shuttle pin (e.g., by blocking advancement of the shuttle pin (650) when the grasper is opened, as discussed in more detail below).

In some of these variations, when a delivery device is used to advance the shuttle pin (650), it may be configured to advance the shuttle pin a predetermined distance (e.g., about 1 cm, about 1.25 cm, about 2 cm, or the like) to actuate the grasper (600). In these variations, the shuttle pin (650) may be sized to be longer than this predetermined distance (e.g., greater than about 2.5 cm, greater than about 3 cm, or the like), such that at least a portion of the shuttle pin (650) may remain in the lumen when fully advanced by the delivery device. In some of these variations, the shuttle pin may be sized with a length such that at least a predetermined length (e.g., about 1.25 cm) of the shuttle pin remains in the lumen (612) when the shuttle pin (650) has been advanced the predetermined distance (e.g., for an advancement distance of about 1.25 cm, the shuttle pin may have a length of about 2.5 cm).

Additionally or alternatively, the grasper (600) may be configured to limit the amount that the delivery device may advance the shuttle pin (650). For example, in some variations, a portion of the grasper (600) may be positioned in the path of the shuttle pin (650) and resists further advancement of the shuttle pin (650) by the delivery device. For example, the pivot point (608) may be positioned along the movement path of the shuttle pin (650). In these variations, the distal end (654) of the shuttle pin (650) may be stopped from further advancement by a portion of the first jaw (602) and/or the proximal arm (620) (and/or the eccentric cam member, in variations where the grasper contains an eccentric cam member) near the pivot point (608).

The grasper (600) shown in FIGS. 6A-6C may be actuated in any suitable manner. In some variations, the grasper (600) may be configured such that it may be actuated by a force applied internally of the grasper (600) (e.g., via an actuation rod of a delivery device advanced through the lumen (612) of the barrel portion (610) of the grasper (600), as discussed in more detail below), and may be further configured such that it may be actuated by a force applied externally of a grasper (600) (e.g., via a grasping device).

FIGS. 7A-7D depict cross-sectional side views of a distal portion of a delivery device (700) and a manner of actuating the grasper (600) using the delivery device (700). The delivery device (700) and grasper (600) may be configured for minimally invasive introduction into the body, such as described above. Specifically, the delivery device (700) may comprise a handle (not shown), a shaft (706) extending from the handle, and a distal engagement portion (708) at a distal end of the shaft (706). The handle may comprise an actuation control mechanism that may be manipulated by a user to controllably actuate the grasper, and may be configured as described above with respect to the handle (104) of the delivery device (100) described above with respect to FIGS. 1A-1C. In some of these variations, the actuation control mechanism may comprise a trigger.

In some of these variations, the actuation control mechanism may be configured to both actuate the grasper (600) and the delivery device (700). In variations where the actuation control mechanism comprises a trigger, the trigger may be moveable between three positions (although it should be appreciated that the trigger may assume one or more intermediate positions between these positions). Of the three positions, the trigger may be moveable between a first position (such as the position of the trigger (112) of the delivery device (100) shown in FIG. 1A) and a second position (such as the position of the trigger (112) of the delivery device (100) as shown in FIG. 1B) to close and open, respectively, the grasper (600). The trigger may be moveable to a third position (such as the position of the trigger (112) of the delivery device (100) as shown in FIG. 1C) to eject or otherwise release the grasper (600) from the delivery device (700). In some of these variations, to move the trigger from the second position (in which the grasper (600) is placed in an open configuration) to the third position (to eject the grasper (600) from the delivery device (700)), the trigger may need to be moved through the first position, thereby moving the grasper (600) to a closed configuration prior to ejecting the grasper (600).

Figure 7A:
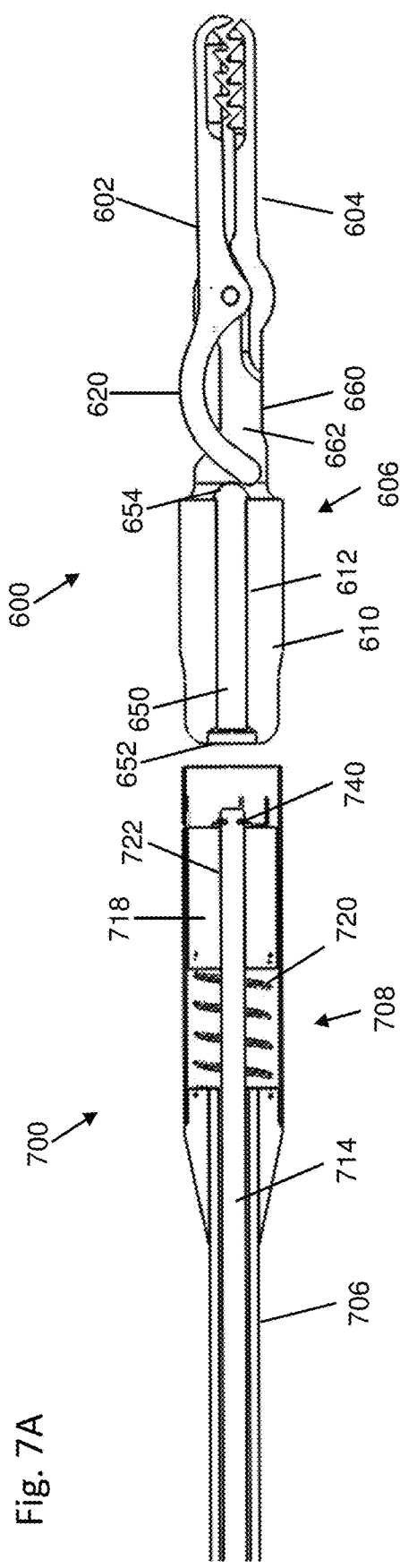
Figure 7B:
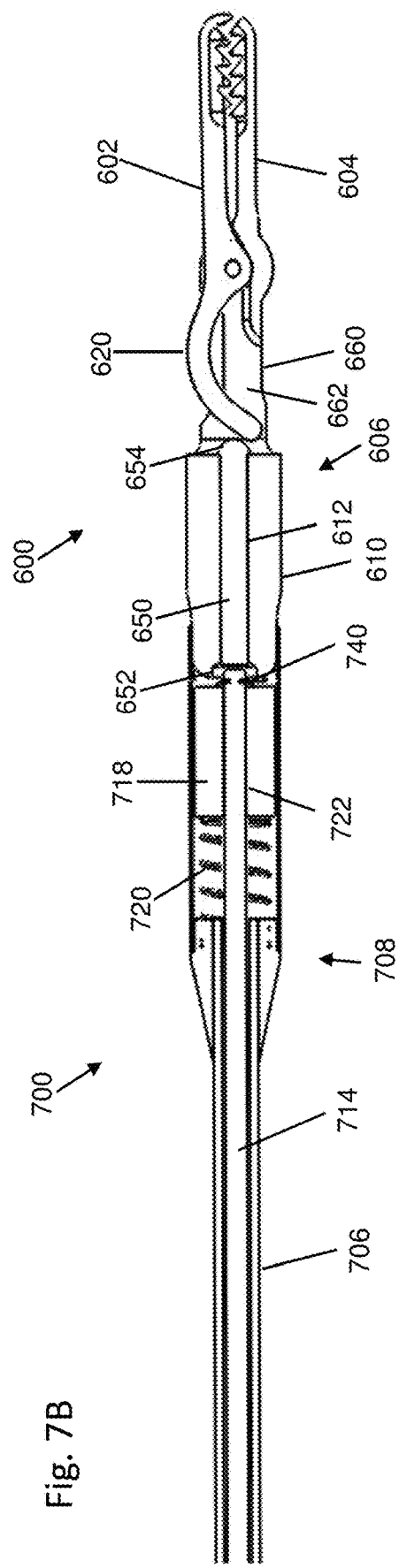

Returning to FIGS. 7A-7D, in some variations the distal engagement portion (708) of the delivery device (700) may comprise a coupling magnet (718) and a spring (720). In these variations, the coupling magnet (718) may be slidably housed in the distal engagement portion (708) (e.g., in a housing of the distal engagement portion (708)). The coupling magnet (718) may be moveable between an advanced position (as depicted in FIGS. 7A-7C) and a retracted position (as depicted in FIG. 7D). The spring (720) may be positioned within the distal engagement portion (708) such that the spring (720) biases the coupling magnet (718) toward the advanced position. The delivery device (700) may be configured to couple to the grasper (600) when the coupling magnet (718) is in the advanced position.

As described in more detail herein, at least a portion of the grasper (600) may comprise one or more materials configured to be attracted by a magnetic field. When the grasper (600) is positioned near the distal engagement portion (708) (such as shown in FIG. 7A), the coupling magnet (718) may attract the grasper (600) and temporarily couple the grasper (600) to the delivery device (700). Similarly, a visualization device (e.g., camera, light source) configured to be coupled to the delivery device (700) may comprise one or more materials configured to be attracted by a magnetic field. When the visualization device is positioned near the distal engagement portion (708), the coupling magnet (718) may attract the visualization device and temporarily couple the visualization device to the delivery device (700).

Specifically, when the grasper (600) is temporarily coupled to the delivery device (700), at least a portion of the barrel portion (610) may be positioned within the distal engagement portion (708), as shown in FIG. 7B. The attractive force between the coupling magnet (718) and the grasper (600) may hold the grasper (600) in place. In variations where the grasper (600) has a barrel portion (610) having a first segment (640) having a first outer diameter and a second segment (642) having a second outer diameter (e.g., FIG. 6B), the second outer diameter may be sized to fit within the distal engagement portion (708) while the first outer diameter may be sized such that it is too large to fit within the distal engagement portion (708). In these variations, the first segment (640) (or a tapered segment (644) between the first segment (640) and the second segment (642)) may act as a stop to limit the amount of the barrel portion (610) that may enter the distal engagement portion (708).

Figure 21:
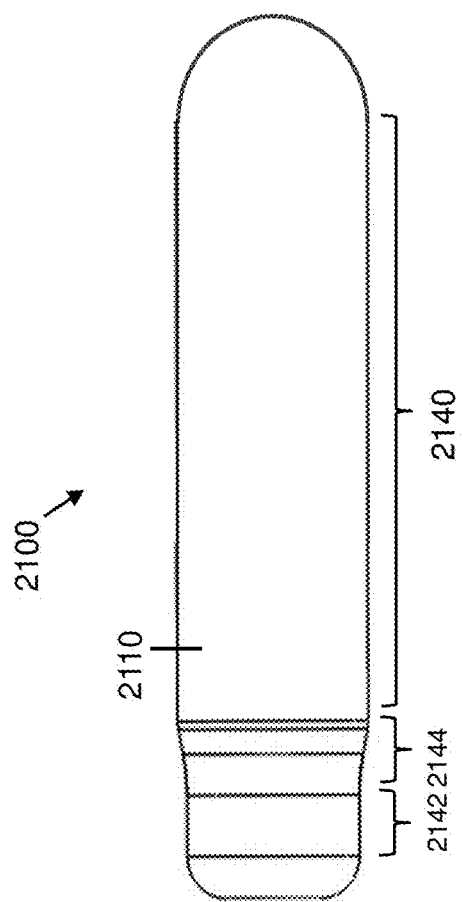
FIG. 21 depicts a side view of an illustrative variation of a camera.

Similarly, as shown in FIG. 21, a visualization device such as a camera (2100) may be configured to be temporarily coupled to the delivery device (700). The camera (2100) may have a capsule-like outer shape as shown, or may have any other suitable shape. The camera (2100) may comprise a lens. The lens may be located in any suitable location, such as but not limited to the distal end of the camera (2100), or along a barrel portion (2110) of the camera. As described in more detail herein, the camera (2100) may comprise one or more magnetic elements, which may be located, for example, at an end of the camera or along a barrel portion. When the camera (2100) is coupled to the delivery device (700), at least a portion of the barrel portion (2110) may be positioned within the distal engagement portion (708), similar to as shown in FIG. 7B. The attractive force between the coupling magnet (718) and the camera (2100) may hold the camera (2100) in place. In variations where the camera (2100) has a barrel portion (2110) having a first segment (2140) having a first outer diameter and a second segment (2142) having a second outer diameter, the second outer diameter may be sized to fit within the distal engagement portion (708) while the first outer diameter may be sized such that it is too large to fit within the distal engagement portion (708). In these variations, the first segment (2140) (or a tapered segment (2144) between the first segment (2140) and the second segment (2142)) may act as a stop to limit the amount of the barrel portion (2110) that may enter the distal engagement portion (708).

It should be appreciated that in some variations the proximal end of the grasper may comprise a magnetic element used with a control element to maneuver the grasper, for example, as described below with respect to FIGS. 8A-12C, 18A-18B, and 19A-19B. In these variations, the magnetic element in the proximal end of the grasper may also be used to attract the distal engagement portion of the delivery device and couple the grasper and the delivery device. In some variations of a visualization device such as a camera and/or light source configured to reversibly couple to the delivery device, a proximal end of a visualization device may comprise a magnetic element. In these variations, the magnetic element in the proximal end of the visualization device may also be used to attract the distal engagement portion of the delivery device and couple the visualization device and the delivery device. This magnetic element is also described in more detail with respect to use of a control element to maneuver the visualization device, for example, as described below with respect to FIGS. 5E, 12D, and 180-18D. Additionally, the delivery device may comprise a coupling magnet, but need not. When the delivery device does not comprise a coupling magnet, a distal engagement portion of the delivery device may comprise a coupling element comprising a ferromagnetic or ferrunagnetic material that is slidably housed in the distal engagement portion. The coupling element may be configured to move between an advanced position and a retracted position, where the delivery device is configured to couple to the grasper (or visualization device) via attractive force between the magnetic element in the grasper and the coupling element when the coupling element is in the advanced position.

In order to decouple the grasper (600) from the distal engagement portion (708), the coupling magnet (718) may be withdrawn to the retracted position, such as shown in FIG. 7D. As the coupling magnet (718) is retracted, the attractive force between the coupling magnet (718) and the grasper (600) may move the grasper (600) proximally relative to the distal engagement portion (708). The first segment (640) (or the tapered segment (644)) may limit the movement of the grasper (600) into the distal engagement portion (708), such that the distance between the coupling magnet (718) and the grasper (600) increases. This may decrease the attractive force between the coupling magnet (718) and the grasper (600), which may allow the grasper (600) to be pulled from, released from, or otherwise fall from the distal engagement portion (708).

The coupling magnet (718) may be retracted in any suitable manner, such as described in more detail above. For example, in the variation of the delivery device (700) shown in FIGS. 7A-7D, the delivery device (700) may comprise an actuation rod (714) slidably disposed in the shaft (706). The actuation rod (714) may be configured to retract the coupling magnet (718). For example, the actuation rod (714) may be slidably disposed within a lumen (722) of the coupling magnet (718). In some variations, at least a segment of the actuation rod (714) may be sized and configured such that the portion of the actuation rod (714) cannot fully pass through the lumen (722). For example, the variations in FIGS. 7A-7D show a segment (740) of the actuation rod that may have a diameter greater than a diameter of the lumen (722).

Additionally or alternatively, the segment (740) may comprise one or more projections extending from an outer surface of the actuation rod (714) and which cannot fully pass through the lumen (722). When the segment (740) of the actuation rod (714) is positioned distal to the coupling magnet (718), the actuation rod (714) may be freely advanced relative to the coupling magnet (718). Conversely, withdrawal of the actuation rod (714) may pull the segment (740) of the actuation rod (714) into contact with the coupling magnet (718). Since the segment (740) cannot fully pass through the lumen (722) of the coupling magnet (718), further withdrawal of the actuation rod (714) may cause the segment of the actuation rod (714) to pull on and withdraw the coupling magnet (718). When the actuation rod (714) is subsequently advanced, the spring (720) may advance the coupling magnet (718) with the actuation rod (714) until the coupling magnet (718) reaches the advanced position.

The actuation rod (714) may be advanced or retracted relative to the shaft (706) to actuate and/or eject the grasper (600). In variations where the handle comprises a trigger (such as discussed above), the trigger may be operatively connected to the actuation rod (714), such that movement of the trigger slides the actuation rod (714). Movement of the actuation rod (714) may rotate the first jaw (602) of the grasper (600). Specifically, when the grasper (600) is coupled to the delivery device (700) (as shown in FIG. 7B), the actuation rod (714) may be aligned with the lumen (612) of the barrel portion (610) such that the actuation rod (714) enters the lumen (612). As the actuation rod (714) is advanced into the lumen (612), the actuation rod (714) may press against the proximal end (652) of the shuttle pin (650) and advance the shuttle pin (650) along the lumen (612). As the shuttle pin (650) is advanced along the lumen (612), the distal end (654) of the shuttle pin (650) may move into the channel (662) of the barrel extension (660). The distal end of the shuttle pin (650) may in turn push against the proximal arm (620) (e.g., against a portion of the proximal arm (620) that is positioned in the channel (662) and aligned with the lumen (612)). The proximal arm (620) may act as a cam to convert the linear motion of the shuttle pin (650) into rotation of the proximal arm (620), which may in turn rotate the first jaw (602) away from the second jaw (604). When the first jaw (602) is spring-biased toward the second jaw (604), the rotation of the proximal arm (620) may overcome this spring bias, which may allow the actuation rod (714) to hold the first jaw (602) in its open position, as shown in FIG. 7C.

Additionally, the first jaw (602) may rotate back toward the second jaw (604) when the actuation rod (714) is retracted. Specifically, as the actuation rod (714) is withdrawn, the return bias of the first jaw (602) may cause the proximal arm (620) to push against the shuttle pin (650), which may slide the shuttle pin (650) proximally within the lumen (612). This may return the grasper (600) to a closed configuration, such as shown in FIG. 7B. When the grasper (600) is closed around tissue, the actuation rod (714) may be further retracted to release the grasper (600) from the delivery device (700), as discussed above. When a trigger is moveable between three positions to actuate and release the grasper (600) as discussed above, placing the trigger in the first position may position the actuation rod (714) in a position as illustrated in FIG. 7B, in which the grasper (600) may be coupled to the delivery device (700) in a closed configuration. Moving the trigger to the second position may advance the actuation rod to the position illustrated in FIG. 7C, in which the grasper (600) may be releasably coupled to the delivery device (700) in an open configuration. Moving the trigger to the third position may retract the actuation rod (714) to the position illustrated in FIG. 7D, in which the grasper (600) may be decoupled from the delivery device (700).

Additionally, in the variation of the grasper (600) shown in FIGS. 6A-6C, at least a portion of the proximal arm (620) may be exposed relative to the main body (606) (e.g., at least a portion of the proximal arm (620) may extend out of the channel (662) of the barrel extension (660)), which may allow a grasping device to grasp the proximal arm (620) to rotate the first jaw (602) relative to the second jaw (604). For example, opposing forces (represented by arrows (622) in FIG. 6C) may be applied (e.g., via a grasping device) to the exposed portion of the proximal arm (620) and the main body (606) (e.g., the barrel extension (660)) to cause the proximal arm (620) to rotate around the pivot point (608) (which may, in turn rotate the first jaw (602) away from the second jaw (604)). In these variations, the height of the walls (664) of the barrel extension (660) may limit the amount that the proximal arm (620) may be rotated (e.g., a grasping device may rotate the proximal arm (620) until the grasping device contacts the top and bottom edges of the wall).

Additionally or alternatively, when the top and/or bottom edges of a wall of the barrel portion are curved or ramped, the curved or ramped edges may help guide a grasping device toward another section of the barrel extension (660) during grasping. Specifically, if the grasping device applies a compressive force at a ramped or curved portion of an edge, the grasping device may slide along the ramped/curved portion toward a shorter portion of the wall. For example, in the variation of the grasper (600) shown in FIGS. 6A-6C, if a grasping device applies a compressive force at either the ramped segments (682) or (684) of the top edge (666), the grasping device may slide toward the linear portion (680).

2. Grasper

As mentioned above, the graspers described herein may comprise a first jaw and a second jaw, and at least one of the first jaw and the second jaw may be configured to rotate relative to the grasper to actuate the grasper between an open configuration and a closed configuration. The jaws may be configured in the closed configuration to secure tissue. In some variations, the graspers may be configured to secure tissue by engaging the tissue between a grasping surface of each of the two jaws (e.g., gripping, squeezing, compressing, etc. the tissue between the two jaws). That is, the jaws may be configured to hold tissue between two surfaces that would be in contact in the closed configuration but for the tissue between the surfaces. In these variations, the jaws of the graspers may comprise one or more features which may promote engagement with tissue. In some variations, one or more surfaces of a jaw may be roughened, which may help to reduce slipping between the jaws and tissues.

Additionally or alternatively, the graspers may comprise teeth or other projections which may facilitate engagement of the jaw with tissue. For example, in the variation of the grasper (600) shown in FIGS. 6A-6C, the first jaw (602) and the second jaw (604) may each include a grasping surface (690) having a plurality of teeth (692). In a closed configuration, the grasper (600) may be configured to engage tissue between the teeth (692) of the grasping surfaces (690). In variations in which the grasper (600) is biased toward the closed configuration, the combination of the size, shape, and features (e.g., teeth) of the grasper (600), as well as the biasing force (e.g., due to a torsional or cantilever spring), may be chosen to produce a desired grasping force on the tissue. It may in some instances be desirable for the grasping force to allow the delivery device to be decoupled from the grasper (600) and to allow the tissue to be held securely during a procedure, while not causing tissue damage.

In other variations, instead of or in addition to squeezing the tissue between contact surfaces, the graspers may be configured to surround tissue in a space formed between the two closed jaws. That is, the jaws may be configured such that in a closed configuration, there is a space between the jaws (even when no tissue is located between the jaws). This space may be used to hold at least a portion of tissue. As such, less force may be applied to tissues during grasping. This may be desirable for use with particular types of tissues (e.g., a portion of tissue having a tubular or elongate shape) and in particular procedures, such as but not limited to reconstructive laparoscopy (e.g., colon, bariatric). In some variations, the graspers may be configured to hold tissue only within the space between the jaws, and not to compress tissue between two contact surfaces. In other variations, the graspers may be configured such that a first portion of tissue may be held within the space between the jaws, and a second portion of tissue may be compressed between the contact surfaces of the jaws.

Figure 13A:
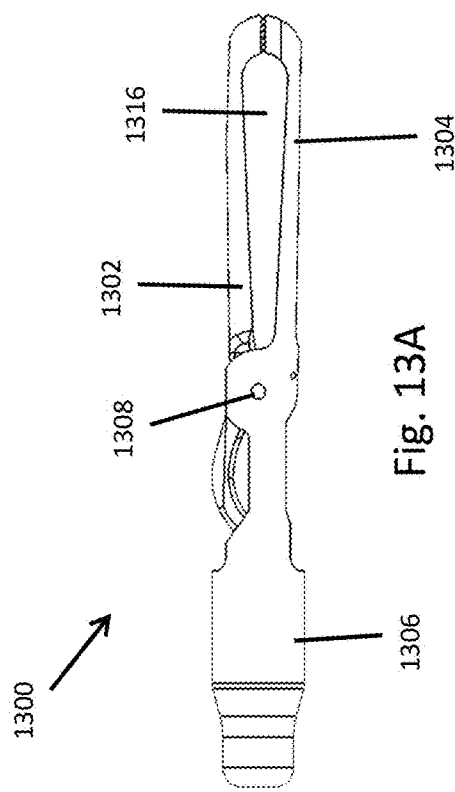
FIGS. 13A and 13B-13D depict side and perspective views, respectively, of an illustrative variation of a grasper as described here.
Figure 13C:
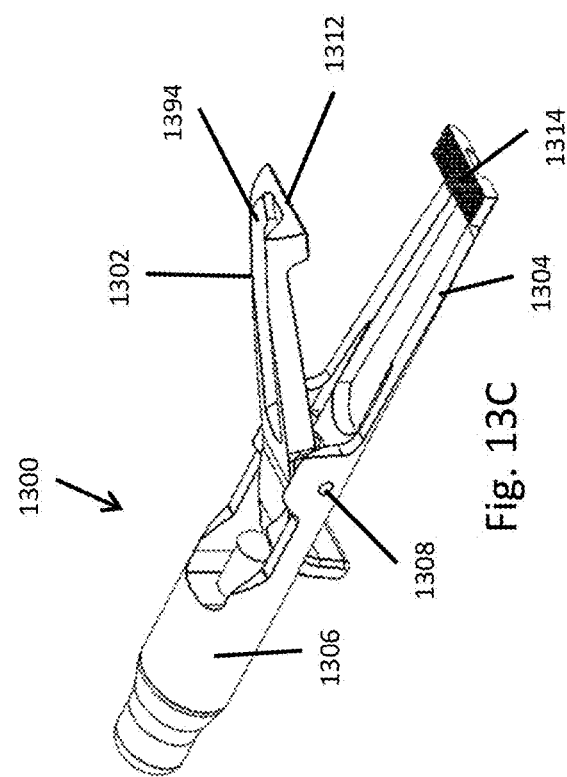
Figure 13B:
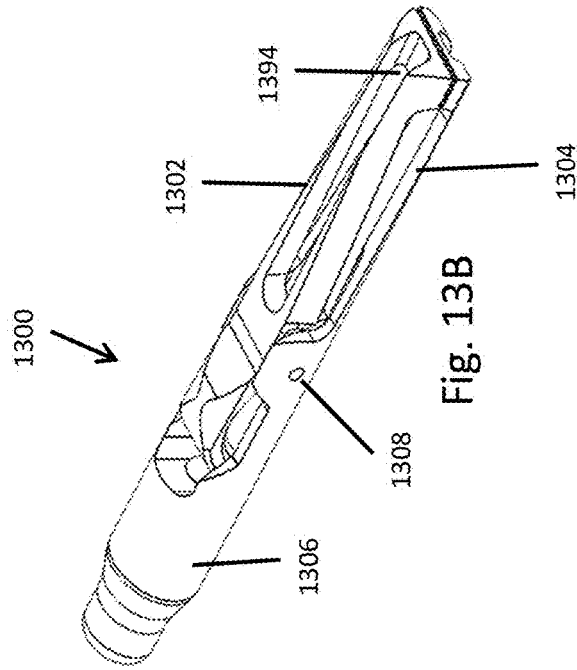

FIGS. 13A-16 show exemplary graspers configured to surround tissue in a space between two closed jaws. FIGS. 13A-13C, for example, depict side (FIG. 13A) and perspective (FIGS. 13B-13D) views of a grasper (1300) in closed (FIGS. 13A-13B) and open (FIGS. 13C-13D) configurations. Grasper (1300) comprises a first jaw (1302), a second jaw (1304), and a main body (1306). First jaw (1302) may comprise a distal contact surface (1312) (labeled in FIG. 13C), which may face a distal contact surface (1314) of the second jaw (1304). Generally, the first jaw (1302) may be rotatably connected to the main body (1306) at a pivot point (1308), such that the first jaw (1302) may be able to rotate relative to the main body (1306). While the second jaw (1304) is shown in FIGS. 13A-13C as being fixed relative to the main body (1306), it should be appreciated that in some variations the second jaw (1304) may be rotatably connected to the main body (1306).

The first jaw (1302) (and/or the second jaw (1304) in variations in which the second jaw (1304) is rotatably connected to the main body (1306)) may be rotated relative to the main body (1306) to actuate the grasper (1300) between an open configuration and a closed configuration. In the closed configuration, the first jaw (1302) and second jaw (1304) may be rotated toward each other such that the contact surfaces (1312, 1314) are touching. This may allow the first and second jaws (1302) to define an enclosed space (1316) between the two jaws (1302, 1304). The space (1316) between the two jaws may be configured to contain tissue. In the open configuration, the first jaw (1302) and the second jaw (1304) may be held in rotationally separated positions to define a space between the distal contact surfaces (1312, 1314), which may allow tissue to enter the space between the first and second jaws (1302, 1304). The first and second jaws (1302, 1304) may be rotationally biased toward a closed configuration in any suitable manner (e.g., via a torsional spring, not shown).

In some variations, the portion of the grasper (1300) proximal to the pivot point (1308) may have the same configuration as grasper (600), and the grasper (1300) may be delivered and actuated between the open and closed configurations using a delivery device as described above with respect to FIGS. 6A-7D. In some variations, the grasper (1300) may comprise features configured to promote secure engagement between the two distal contact surfaces (1312, 1314) in the closed configuration, and/or to promote engagement with tissue. For example, the contact surfaces may comprise teeth, grooves, ridges, or the like to promote secure engagement, which may help to keep any tissue enclosed in the space between the jaws from slipping between the contact surfaces, or may help to hold onto any tissue gripped, squeezed, etc. between the contact surfaces.

In variations in which the graspers are configured to surround tissue in a space between the two closed jaws, the space may have any suitable shape. In some variations, the jaws may form an elongate space extending from near the pivot point to the contact surface, as shown for example in FIGS. 13A-13B, where the jaws (1302, 1304) of a grasper (1300) form a space (1316) from the pivot point (1308) to the contact surfaces (1312, 1314).

Another example is shown in FIGS. 14A-14D, which depicts side (FIGS. 14A-14B) and perspective views (FIGS. 14C-14D) of grasper (1400) in closed (FIGS. 14A and 14C) and open (FIGS. 14B and 14D) configurations. A grasper (1400) may comprise a first jaw (1402), a second jaw (1404), and a main body (1406) having the same features as grasper (1300) described herein, including a space (1416) formed by the first and second jaws when in the closed configuration. The space (1416) may extend from the pivot point (1408) to the contact surfaces (1412, 1414).

Figure 13D:
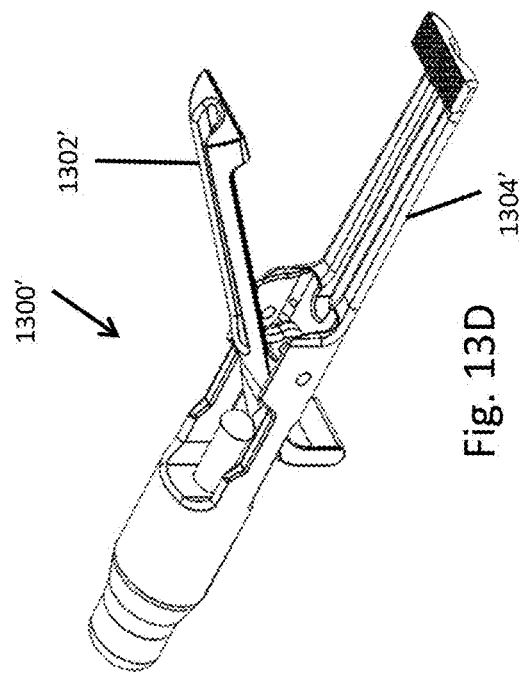
Figure 15C:
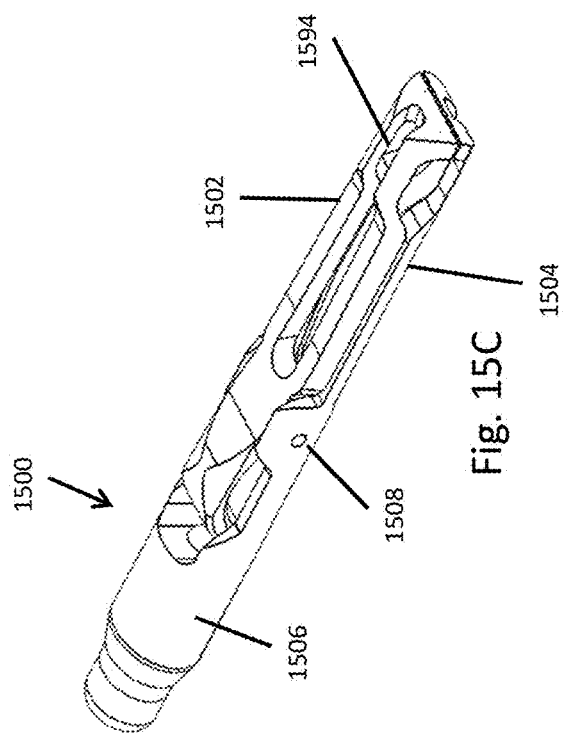
FIGS. 15A-15B and 15C-15D depict side and perspective views, respectively, of an illustrative variation of a grasper as described here.
Figure 15D:
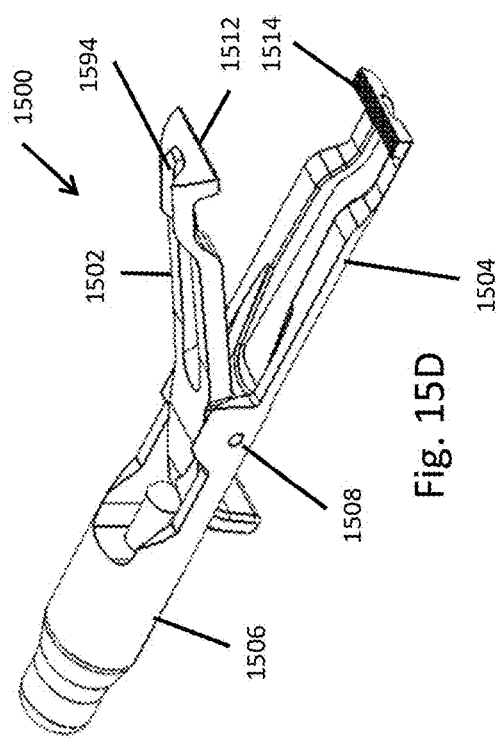
Figure 15A:
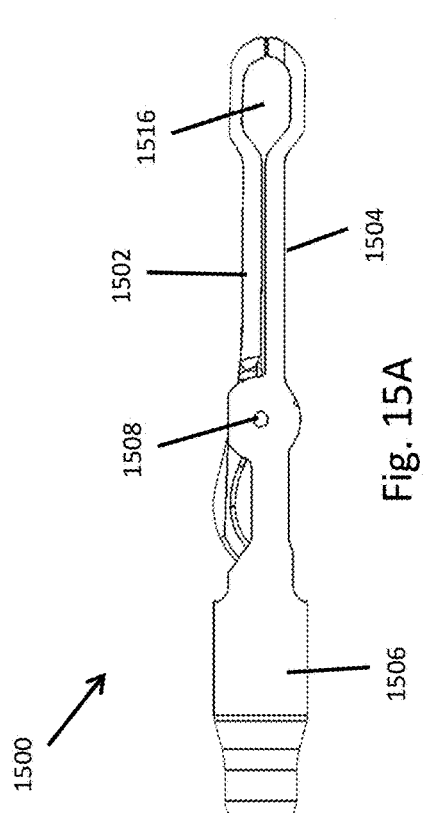
Figure 15B:
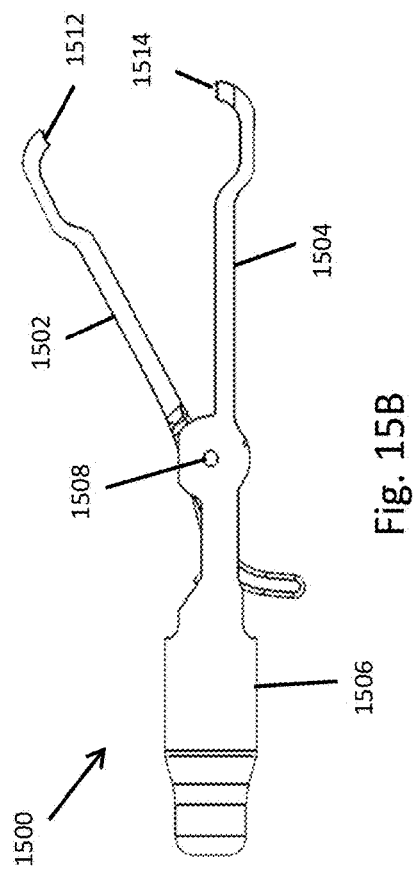

As can be seen in comparing graspers (1300) and (1400), the jaws may have any suitable length. Whereas the pivot point (1308) in grasper (1300) is located approximately in the middle of grasper (1300), the pivot point (1408) in grasper (1400) is located closer to the distal end; that is, the jaws are shorter in grasper (1400) and form a shorter space (1416). Particular jaws designs may be desirable in order to create spaces of particular sizes (e.g., in order to hold particular tissues). It may also be desirable for the jaws to have different shapes. While the grasper (1300) in FIGS. 13A-13C comprises first and second jaws (1302, 1304) that slightly taper toward the distal end of the jaws (best shown in FIG. 13C), in other variations the jaws may have a uniform width from their proximal to distal ends. For example, FIG. 13D shows a grasper (1300'), which has first and second jaws (1302', 1304') having a uniform width from their proximal to distal ends.

In other variations, the jaws may be configured to form a space only at the distal end of the jaws and not between a pivot point and the distal end. For example, FIGS. 15A-15D show a grasper (1500) having a first jaw (1502), a second jaw (1504), and a main body (1506) having similar features as grasper (1300) described herein, including a space (1516) between the closed jaws (1502, 1504). However, unlike grasper (1300), the first and second jaws (1502, 1504) may contact each other immediately distal to the pivot point (1508). Thus, the space (1516) is located closer to the distal end of the jaws (1502, 1504), and extends from an intermediate location along the jaws (1502, 1504) to the contact surfaces (1512, 1514). Particular locations of the space (1516) relative to the rest of the grasper (1500) may be desirable to control the distance between tissues. For example, when the grasper is located within a body cavity and a magnetic field of an external control element holds the grasper in a perpendicular configuration with the proximal end of the grasper body against the cavity wall, the location of the space (1516) along the jaws (1502, 1504) may determine the distance of the tissue held in the space to the cavity wall.

In some variations, one or more jaws of the graspers described here may include a longitudinal recess extending at least partially through the jaws. With reference to FIG. 6C for example, grasper (600) may include a recess (694) extending at least partially through the grasping surface (690) and some of the teeth (692). Similarly, graspers (1300), (1400), and (1500) may include recesses (1394), (1494), and (1594), respectively, extending at least partially through each of first and second jaws (1302, 1304), (1402, 1404) and (1502, 1504), respectively. In these variations, when the jaws are used to grasp tissue therebetween, tissue may be squeezed or captured into or otherwise enter the recess of each jaw, which may help to provide a more secure hold between the grasper and the tissue. The size and placement of the recesses may also influence the effect of a magnetic field on the graspers, as described in more derail below.

In some variations of the graspers described here, the grasper may comprise one or more coatings which may help to smooth discontinuities in the contours of the grasper and may act to provide one or more atraumatic surfaces of the grasper. The one or more coatings may comprise silicone, urethane, one or more nylon blends, polyethylenes, fluoropolymers, combinations thereof and the like. It may also be desirable to use certain coatings and/or materials in or on all or a portion of the grasper in order to reduce the occurrence of unintended electrical current flowing through the grasper. For example, in a surgical procedure involving electrical current (e.g., electrocautery), if the grasper contacts an electrocautery instrument, the electrical current may flow through the grasper and cause cauterization of, or burns in, the various tissues touching the grasper. This cauterization or burning of the tissue may be unintended and/or undesirable. Thus, non-conducting materials and/or coatings may be used on all or a portion of the grasper (e.g., a portion of the grasper closest to the surgical site) to reduce or eliminate the flow of electrical current through the grasper and thus reduce the likelihood that tissue may be damaged unintentionally by electrical current. For example, and as described in more detail below, in some variations, one of the jaws of a grasper (such as any of the graspers described herein) may be made of non-conducting material. Additionally or alternatively, the distal portion of one or both of the jaws of a grasper (such as any of the graspers described here) may be made of a non-conducting material. Any suitable non-conductive material (e.g., plastic, or the like) and/or non-conductive coating (e.g., paints, plastic tubing, co-molded thermoplastic elastomers, a combination thereof, or the like) may be used. In some instances, materials used for non-conductive properties may be the same as those used for non-magnetic properties (e.g., plastic), which are described in more detail below.

B. Maneuvering the Grasper

As mentioned above, the graspers described here may be used to provide remote manipulation of tissue during a minimally-invasive procedure. During such a procedure, it may be desirable to maneuver and/or control the grasper using one or more elements located outside of the body (e.g., one or more control elements), so that the delivery devices described here may be withdrawn, and the access ports may be utilized for other tools and/or instruments. It may also be desirable to maneuver another tool, such as a visualization device (e.g., camera, light source) using one or more elements located outside of the body (e.g., one or more control elements), so that the position and/or orientation of the visualization device can be controlled without occupying an access port.

Maneuvering and/or controlling the grasper using one or more elements located outside the body, and not through a physical connection via an access port, may additionally or alternatively allow for force to be applied to the grasper (and in turn to tissue) in a direction different from the direction of force that may be applied through an access port. This may allow force to be applied to the grasper (and in turn to tissue) in a greater number of directions. Additionally or alternatively, maneuvering and/or controlling the grasper using one or more elements located outside the body, and not through a physical connection via an access port, may allow for improved visualization of a region of interest. In some variations, it may be desirable to control an orientation of the grasper using one or more elements located outside of the body (e.g., one or more control elements) to increase maneuverability and control of the grasper.

Generally, the graspers and/or visualization devices may be maneuvered using one or more attractive and/or repulsive forces. Specifically, the graspers and/or visualization devices may be configured to be attracted to and/or repelled by one or more magnetic elements positioned externally of the body. Attractive and/or repulsive forces originating from outside the body may be used to move, reposition, and/or hold the grasper and/or visualization device. These forces may in turn move, hold, and/or provide traction for the tissue held by the grasper. In some instances, it may be desirable to configure the grasper and/or visualization device and the control element such that their magnetic attributes and/or those of the control element do not affect other instruments that are not intended to be part of the magnetically controlled grasping system described herein.

The graspers described here may generally comprise a combination of materials having different magnetic behavior. Varying the type of materials in the grasper, where they are located in and/or on the grasper, and the configuration of those materials, may serve several purposes. Generally, the arrangement of non-magnetic, ferromagnetic, ferrimagnetic, and/or diamagnetic materials within an instrument may alter the behavior of the instrument when it is exposed to a magnetic field. The use of a combination of these materials may provide increased control over the movements of the grasper and the tissue held within its jaws, as compared to a grasper made from only one type of material. The configuration of the materials within the grasper—for example, the type, amount, polarity, and location of the materials—may alter how the grasper responds to and/or interacts with a control element. It should be appreciated that the types, location, and configuration of materials with respect to graspers described herein may also be implemented with respect to visualization devices such as cameras and/or light sources as appropriate to affect the behavior of the tool when exposed to a magnetic field. The use of combinations of materials may similarly provide increased control, for example, over the movements of a camera and the orientation of its field of view.

For example, using both magnetic and non-magnetic materials may affect which portions of the grasper or visualization device (e.g., camera, light source) are attracted to, unaffected by, or repelled by magnetic fields generated by the control element (and may affect which portions of the grasper or visualization device may create magnetic fields that may attract, not affect, or repel portions of the control element).

As another example, increasing the amount of magnetic material located in a specific portion of the grasper or visualization device (e.g., camera, light source) may increase the attractive or repulsive force between that portion of the grasper/visualization device and a control element. Similarly, removing magnetic material from a specific portion of the grasper or visualization device and replacing it with a non-magnetic material may decrease the attractive or repulsive force between that portion of the grasper/visualization device and the control element. Varying the type of materials and where they are located may also modify the distribution of the mass of the grasper or visualization device, which may contribute to a user's ability to control and maneuver the grasper or visualization device. As mentioned above, this may provide for better control over the grasper and the tissue within its jaws, as described in more detail below.

As another example, the response of a grasper to an applied magnetic field may also be altered by removing material entirely to leave an air gap (in instances where the material is not required for the grasper to hold tissue as desired). With reference to FIG. 6C for example, grasper (600) may include a recess (694) extending at least partially through the grasping surface (690) and some of the teeth (692) of the first jaw (602). In variations in which the jaws (602, 604) comprise a material attracted to a magnetic field, when a magnetic field is applied to grasper (600), a greater force may be generated on the second jaw (604) than the first jaw (602), since the second jaw (604) comprises more material. As a result, when the grasper (600) is located in a body cavity and controlled by a magnetic field from an external control element, the grasper (600) may have an increased tendency to lie parallel to the cavity wall with the second jaw (604) against the cavity wall.

Figure 16:
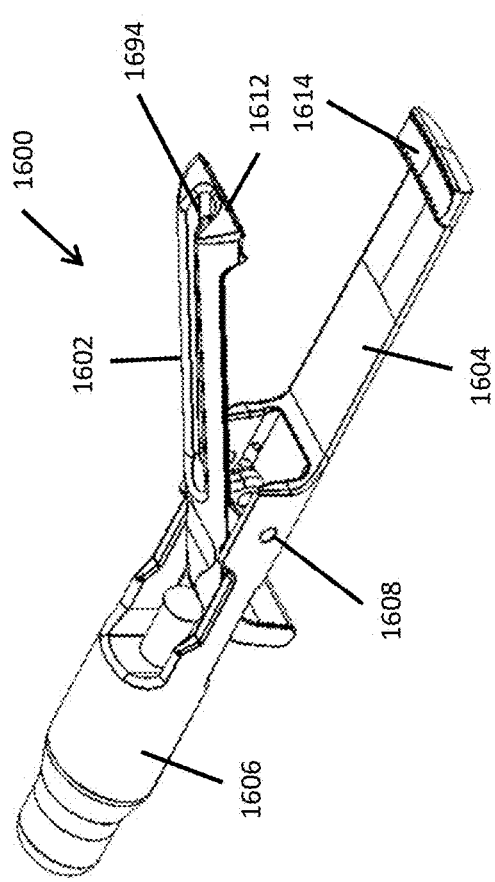
FIG. 16 depicts a perspective view of an illustrative variation of a grasper as described here.

The recess may have any suitable configuration or placement. For example, FIG. 16 depicts a grasper (1600) comprising a first jaw (1602) having a recess (1694) extending through and along the length of the first jaw, a second jaw (1604) not having a recess, and a main body (1606). In variations in which the jaws (1602, 1604) comprise a material attracted to a magnetic field, when a magnetic field is applied to the grasper (1600), a greater force may be generated on the second jaw (1604) than the first jaw (1602), since the second jaw (1604) comprises more material. As a result, under application of a magnetic field, the grasper (1600) may have an increased tendency to lie parallel to the cavity wall with the second jaw (1604) against the cavity wall.

As another example, graspers (1300), (1400), and (1500) shown in FIGS. 13A-13D, 14A-14D, and 15A-15D may comprise recesses (1394), (1494), and (1594), respectively, extending through and along the length of each of the first and second jaws. As a result, in variations in which the jaws and body of the graspers are made from a material attracted to a magnetic field, when a magnetic field is applied to graspers, a greater force may be generated on the main bodies (1306), (1406), and (1506) of the graspers than on the jaws. As a result, when the graspers are located in a body cavity and controlled by a magnetic field from an external control element, the graspers may have an increased tendency to be perpendicular to the cavity wall, with the bodies of the graspers against the cavity wall.

Additionally or alternatively, employing both magnetic and non-magnetic materials may allow for control over the grasper from outside the body while decreasing the likelihood that other surgical instruments will be attracted to and/or will stick to the grasper. These other instruments, when attracted to and/or stuck on the grasper, may interfere with the ability to execute fine motions that may be required during a surgical procedure, and may cause delays during surgical procedures caused by the need to separate surgical instruments that may have been inadvertently attracted to and/or become stuck on the grasper. To reduce these undesired effects, parts of the grasper may for example be composed of non-magnetic materials (e.g., 300-series stainless steel, plastic, or the like) and/or be coated with a non-magnetic coating, including but not limited to, non-magnetic paints, plastic tubing, co-molded thermoplastic elastomers, a combination thereof, and the like. These non-magnetic materials anti/or coatings may reduce or eliminate the attraction between the grasper and other instruments, while maintaining the ability to control the grasper from outside the body.

For example, in some variations a portion of the grasper may be made from plastic (e.g., both jaws, one jaw, a distal portion of one or both jaws, a proximal portion of one or both jaws, a combination thereof, or the like) while the remainder of the grasper may comprise a ferromagnetic material. In these variations, the plastic portion of the grasper will not attract surgical tools, but the grasper may still be controlled using an external control element.

In variations in which a non-magnetic coating may be applied to a magnetic material, the coating may increase the distance between the magnetic material and the surgical instruments, and may prevent close contact between the magnetic material and the instruments. This may decrease the attractive force between the coated portion of the grasper and the surgical instruments, but may still allow the grasper to be controlled by an external control element. In some instances, it may be desirable to use non-magnetic materials and/or coatings on the portion of the grasper closest to the surgical site (e.g., all or a portion of the jaws, such as a proximal portion); however, such materials and/or coatings may be utilized at any location on the grasper that does not interfere with the control of the grasper or the coupling of the delivery devices using a coupling magnet, as described above. Generally, thicker coatings will decrease the force between the grasper and the other instruments, and coatings of any suitable thickness may be used to achieve a desired force profile. In some variations, it may also be possible to use diamagnetic materials and/or coatings to reduce the likelihood that other surgical instruments will be attracted to and/or will stick to the grasper. A visualization device such as a camera and/or light source may also be in part composed of non-magnetic materials and/or comprise a non-magnetic coating for similar reasons.

The control elements described here may optionally comprise a combination of magnetic and non-magnetic materials. The configuration of the magnetic and non magnetic materials within the control element, for example, the size, type, quantity, polarity, and location of the materials, may alter the behavior of the grasper or visualization device (e.g., camera, light source). The control elements described here may also have a surface that, in use, may be placed on or near an external surface of a patient's body cavity and that may be parallel to the external surface of the patient's body cavity. The grasper and the control element may be configured to yield a desired grasper position and/or movement within the body. For example, in some variations, the control element and the grasper may be configured to rotate, move, and/or hold the grasper such that it is in a perpendicular configuration relative to the internal wall of the patient's body cavity or the surface of the control element, i.e., with its longitudinal axis transverse to, and in some instances, substantially perpendicular to, the surface of the cavity wall or of the control element. Similarly, a visualization device (e.g., camera, light source) and control element may be configured to yield a desired visualization device position and/or movement within the body. For example, the control element and visualization device may be configured to rotate, move, and/or hold the visualization device such that it is in a perpendicular configuration relative to the internal wall of the patient's body cavity or the surface of the control element, i.e., with its longitudinal axis transverse to, and in some instances, substantially perpendicular to, the surface of the cavity wall or of the control element.

In other variations, the control element and the grasper may be configured to rotate, move, and/or hold the grasper in a parallel configuration, i.e., in a configuration in which its longitudinal axis extends in the same direction as, or in some instances, is substantially parallel to, the surface of the cavity wall or of the control element. In some instances, the control element and the grasper may be configured to rotate, move, and/or hold the grasper such that its longitudinal axis forms an angle between about 5 and about 85 degrees with the surface of the cavity wall or of the control element. In some instances, the control element and the grasper may be configured to move the jaws of the grasper while maintaining the positioning of the proximal end of the grasper. Similarly, in other variations, the control element and a visualization device (e.g., camera, light source) may be configured to rotate, move, and/or hold the visualization device in a parallel configuration, i.e., in a configuration in which its longitudinal axis extends in the same direction as, or in some instances, is substantially parallel to, the surface of the cavity wall or of the control element. In some instances, the control element and the visualization device may be configured to rotate, move, and/or hold the visualization device such that its longitudinal axis forms an angle between about 5 and about 85 degrees with the surface of the cavity wall or of the control element.

As mentioned above, the graspers (and visualization device, such as a camera and/or light source) and control elements described here comprise magnetic elements. Generally, at least one of the elements in either the grasper (or visualization device) or the control element comprises a permanent magnet, an electromagnet, or an electro-permanent magnet. The remaining magnetic elements in the graspers (or visualization devices) and control elements may comprise permanent magnets, electromagnets, or electro-permanent magnets, and/or may comprise other materials that are attracted to, and/or repelled by a magnetic field, including, but not limited to ferromagnetic materials, ferrimagnetic materials, diamagnetic materials, a combination thereof, and the like. In some variations both the grasper (or visualization device) and the control element may comprise one or more permanent magnets. For example, they may both comprise permanent magnets oriented such that the dissimilar poles of the magnets attract each other when the grasper (or visualization device) and control element are in the desired configurations. However, the grasper (or visualization device) and control element need not both comprise permanent magnets. For example, in some variations, the grasper (or visualization device) may comprise a magnetic element comprising a ferromagnetic or ferrimagnetic material (e.g., iron, cobalt, nickel, and the like) that is attracted to a magnetic field but does not independently generate a magnetic field, and the control element may comprise a magnetic element (e.g., a permanent magnet) that generates a magnetic field that attracts the ferromagnetic or ferrimagnetic material.

In some surgical procedures, or at times during a surgical procedure, it may be desirable for the grasper to move to and/or be held in a perpendicular or angled configuration with respect to the control element and/or the wall of a patient's body cavity (e.g., an abdominal cavity). FIG. 8A depicts a cross-sectional side view of a variation of a grasper (800) configured to be used with a control element located outside of the body to place the grasper in a perpendicular orientation relative to the cavity wall, and FIG. 8B depicts a variation of a system comprising a control element (816) and the grasper (800) of FIG. 8A positioned in a perpendicular configuration relative to the body cavity.

As shown in FIG. 8A, the grasper (800) may comprise a first jaw (802) rotatably coupled to a main body (806), a second jaw (804) fixed relative to the main body (806), a proximal end (810), a distal end (808), a longitudinal axis (814), and a magnetic element (812). In this variation, the magnetic element (812) may be located in or on the main body (806) at a proximal end (810) of the grasper (800). When the grasper (800) is exposed to a magnetic field generated by a control element (816) comprising a magnet, the proximal end (810) of the grasper (800) may be attracted to the control element (816). The remainder of the grasper (800) (aside from the magnetic element), including, for example, the remainder of the main body (806) and the first and second jaws (802, 804), may in some instances comprise a non-magnetic material. In other instances, all or a portion of the remainder of the main body (806) and the first and second jaws (802, 804) may comprise a second magnetic element that experiences a repulsive force when placed close to the control element (816), for example, a diamagnetic material (e.g., copper, zinc, lead, and the like) or a permanent magnet having a polarity causing it to be repelled by the control element.

Turning back to FIG. 8A, in the embodiment shown there, the magnetic element (812) may comprise a magnet with north and south poles oriented axially within the grasper (800) such that the poles are positioned along the longitudinal axis (814) of the grasper (800). More particularly, the south pole (represented by the letter "S" throughout the figures) of the magnetic element (812) faces a proximal end of the grasper (800) and the north pole (represented by the letter "N" throughout the figures) faces a distal end of the grasper (800). FIG. 8B depicts the grasper (800) of FIG. 8A in use with a control element (816) comprising a longitudinal axis (820). Shown there is a cross-sectional side view of the cavity wall (822), the grasper (800) located within the body, and the control element (816) located outside of the body. The control element (816) is depicted as a magnet comprising poles that face toward and away from the cavity wall (822). As depicted, the north pole of the control element (816) faces downward, or toward the cavity wall (822), and the south pole of the control element (816) faces upward, or away from the cavity wall (822). While the control element (816) is depicted as a magnet itself, it need not be. In some variations, the control element (816) may comprise a combination of one or more non-magnetic materials (e.g., plastics, paramagnetic materials such as titanium, and the like) and one or more magnets.

As depicted in FIG. 8B, the attractive forces between the control element (816) and the magnetic element (812) may move the proximal end (810) of the grasper toward the control element (816). More specifically, the south pole of the magnetic element (812) in the grasper (800) may be attracted to the north pole of the control element (816). The attractive forces between the magnetic element (812) in the grasper (800) and the control element (816) may cause the proximal end (810) of the grasper (800) to be attracted to and move toward the control element (816) and the cavity wall (822), while the distal end (808) of the grasper (800) may be repelled by and move away from the control element (816) and the cavity wall (822). Accordingly, the attractive forces between the magnetic element (812) and the control element (816) may cause the grasper (800) to rotate and/or move into a position in which its longitudinal axis (814) is transverse, and substantially perpendicular to, the surface of the cavity wall (822). In this position, the first and second jaws (802, 804) of the grasper may be facing posteriorly (i.e., inward toward the body) and away from the cavity wall (822). Additionally, if the control element (816) is moved relative to the cavity wall (822) (e.g., moving the control element (816) along the exterior of the body), the grasper (800) may be moved relative to the cavity wall by a corresponding amount by the attractive forces between the magnetic element (812) and the control element (816).

In some variations, the grasper (800), magnetic element (812), and the control element (816) may be configured such that the attractive forces between the magnetic element (812) and the control element (816) cause the grasper (800) to rotate and/or move into a position in which the longitudinal axis (814) of the grasper (800) is located at an angle that is less than 90 degrees with respect to the surface of the cavity wall (822). It should be appreciated that in use there may be many variables that may affect the angular orientation of the graspers described here with respect to a cavity wall, including but not limited to, the location, number, orientation and strength of the magnetic elements in the grasper and the control element, the material of the grasper, gravity, and/or the tension force from organs or other tissue held by the grasper. The grasper (800) and the control element (816) may be configured to have an attractive force between them that places the grasper in a desired angular orientation considering these variables.

Figure 9A:
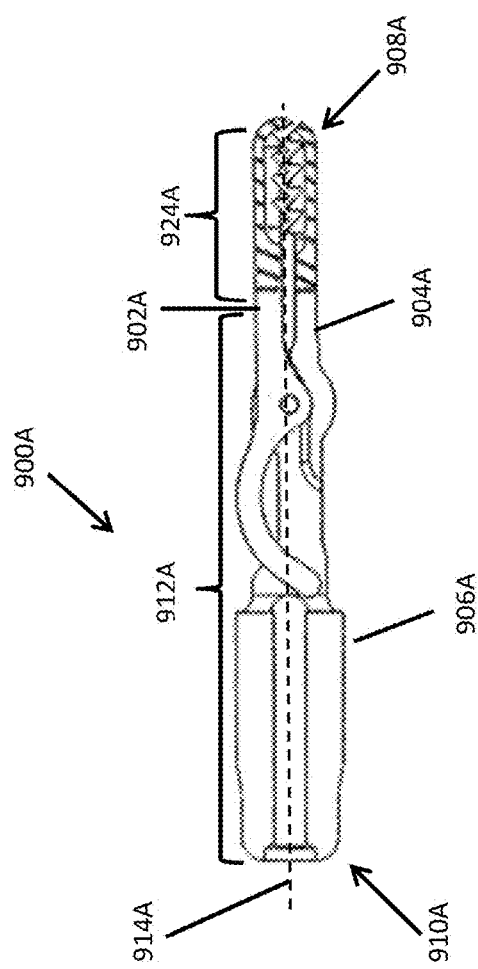
FIGS. 9A and 9B depict cross-sectional sides view of illustrative variations of a grasper described here.
Figure 9B:
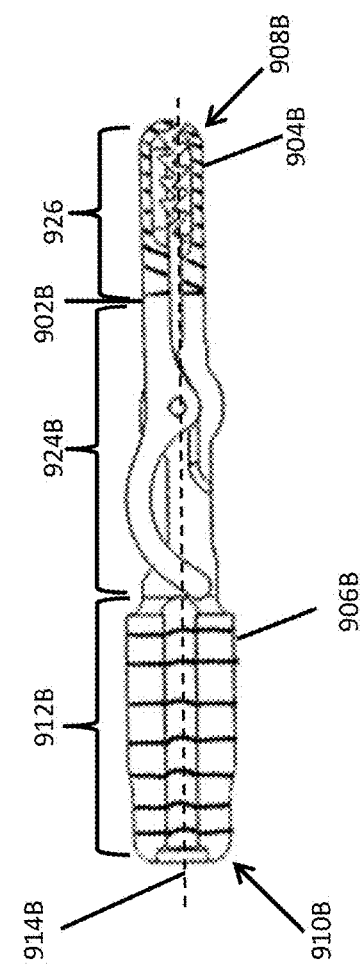

In some variations, the material used to fabricate the grasper may itself be the magnetic element. For example, the graspers (900A, 900B) depicted in FIGS. 9A and 9B are similar to the grasper (800) of FIG. 8A, except that the magnetic element (912A, 912B) of the graspers (900A, 900B) in FIGS. 9A and 9B is the material used to create a portion of the grasper (900A, 900B). Put another way, the material used to create a portion of the grasper (900A, 900B) may be attracted to a portion of the control element (e.g., control element (916) in FIG. 9C). As such, the control element (916) may be used to control and/or maneuver the grasper (900A, 900B). As depicted in FIGS. 9A and 9B, the graspers (900A, 900B) may comprise a first jaw (902A, 902B), a second jaw (904A, 904B), a main body (906A, 906B), a longitudinal axis (914A, 914B), a distal end (908A, 908B), a proximal end (910A, 910B), and a magnetic element (912A, 912B).

In some instances, the grasper may comprise a magnetic element and one additional material, while in other variations the grasper may comprise a magnetic element and multiple additional materials. For example, FIG. 9A depicts a grasper (900A) comprising a magnetic element (912A), a second material (924A), a main body (906A), and first and second jaws (902A, 904A). In this variation, the magnetic element (912A) may be the material of the main body (906A) and a proximal portion of the first and second jaws (902A, 904A), while a distal portion of the first and second jaws (902A, 904A) may be a second material (924A). In some instances, the first magnetic element (912A) may be a ferromagnetic material (e.g., 400-series stainless steel or the like) and the second material (924A) may comprise a non-magnetic material (e.g., 300-series stainless steel, plastic or the like).

In some variations, more or less of the grasper may be made from the magnetic element (912A) (e.g., any portion of the main body (906A) and/or more or less of the proximal portion of the first and second jaws (902A 904A)). For example, in some instances, the top half of the grasper (i.e., the portion above the longitudinal axis (914A)) may be made from the magnetic element (912A), while the bottom half of the grasper (i.e., the portion below the longitudinal axis (914A)) may be made from a non-magnetic material. As another example, one jaw may be made from a non-magnetic material, while the other jaw may be made partially from a ferromagnetic material and partially from a non-magnetic material (e.g., a distal end may be made from a non-magnetic material). In some of these instances in which one jaw is rotatable relative to the main body and one jaw is fixed relative to the main body, the rotatable jaw may be made from a non-magnetic material, while the fixed jaw may be made partially from a ferromagnetic material and partially from a non-magnetic material. For example, with reference to FIG. 9A, first jaw (902A) may be made from a non-magnetic material, while second jaw (904A) may be made partially from a ferromagnetic material and partially from a non-magnetic material. More particularly, in some variations the distal end of the second jaw (904A) may be made from a non-magnetic material, while the remainder of the second jaw (904A) proximal to the distal end may be made from a ferromagnetic material. It should be appreciated that in other instances in which one jaw is rotatable relative to the main body and one jaw is fixed relative to the main body, the fixed jaw may be made from a non-magnetic material, while the rotatable jaw may be made partially from a ferromagnetic material and partially from a non-magnetic material. In some cases, non-magnetic material may also be replaced with a recess, as described in more detail above. In still other variations, the second material (924A) may be a material that experiences a repulsive force when exposed to the control element (916).

In some instances, and as depicted in FIG. 9B, a proximal portion of the grasper (900B) may comprise a magnetic element (912B), a central portion of the grasper (900B) may comprise a second material (924B), and a distal portion of the grasper (900B) may comprise a third material (926). The second and third materials (924B, 926) may comprise a non-magnetic material (e.g., plastic or the like), a magnetic material coated with a non-magnetic material, a combination thereof, or the like.

Additionally or alternatively, the magnetic element (912B), the second material (924B), and the third material (926) need not have the same mass, and it may be desirable to vary the mass of the materials (912B, 924B, 926) to achieve better control over the grasper (900B). For example, varying the mass in different portions of the grasper may also vary the gravitational force that may counteract an attractive force between a specific portion of the grasper and the control element.

Additionally or alternatively, as described in more detail herein, in some variations, decreasing the mass of some portions of the grasper (e.g., by removing material) may also decrease the attractive force between that portion and the control element. In some embodiments, the second and/or third material (924B, 926) may also comprise magnetic elements. In some of these embodiments, the second and/or third materials (924B, 926) may be materials that experience a repulsive force when exposed to the control element (916). It should be appreciated that the second and third materials (924B, 926) need not be in the locations or proportions indicated in FIG. 9B, and may instead have any locations and proportions that facilitate maneuvering the grasper (900B) with the control element (916).

FIG. 9C depicts the grasper (900A) of FIG. 9A in use with a control element (916) comprising a longitudinal axis (920). A cross-sectional side view of the cavity wall (922) can also be seen, with the grasper (900A) located within the body, and the control element (916) located outside of the body. The attractive force between the control element (916) and the magnetic element (912A) may move the proximal end (910A) of the grasper (900A) towards the control element (916). The grasper (900A) may then be in a similar perpendicular position to that described with respect to FIG. 8B. In variations in which a proximal portion of the grasper (900A) comprises a material that is repelled by the control element (916), the repulsive force may also contribute to the movement of the grasper (900A) and may aid in positioning the grasper (900A) in the perpendicular configuration.

Likewise, in some surgical procedures, it may be desirable for the grasper to move to and/or be held such that its longitudinal axis lies parallel to the cavity wall. FIG. 10A depicts a cross-sectional side view of a variation of a grasper (1000) configured to be used with a control element located outside of the body to place the grasper in a parallel configuration. FIGS. 10B and 10C depict variations of a system comprising a control element (1016, 1026) and the grasper (1000) of FIG. 10A in a parallel configuration. FIG. 10A depicts a variation of a grasper (1000) comprising a first jaw (1002), a second jaw (1004), a main body (1006), a proximal end (1010), a distal end (1008), a longitudinal axis (1014) and a magnetic element (1012). In some variations, the magnetic element (1012) may have north and south poles. The north and south poles may be oriented along the axial length of the grasper (1000) (i.e., along its longitudinal axis (1014)). The remainder of the grasper (1000) (aside from the magnetic element (1012)) including, for example, the remainder of the main body (1006) and the first and second jaws (1002, 1004), may comprise a non-magnetic material, ferromagnetic material, ferrimagnetic material, a combination thereof, or the like. In some instances, the grasper (1000) may comprise a second magnetic element in a portion of the remainder of the grasper (1000) that may comprise a material that experiences a repulsive force when exposed to a magnetic field generated by the control element (1016, 1026) (e.g., a diamagnetic material).

The grasper (1000) depicted in FIGS. 10A-10C may comprise a magnetic element (1012) in the form of a magnet positioned axially along the length of the grasper (1000). The magnetic element (1012) has a north pole and a south pole and is oriented such that its north and south poles face the proximal and distal ends (1010, 1008) of the grasper (1000), respectively. FIG. 10B depicts a system comprising the grasper (1000) depicted in FIG. 10A and a control element (1016) comprising a longitudinal axis (1020) and a magnetic element (1024). As shown, the magnetic element (1024) in the control element (1016) may comprise a magnet having north and south poles. The north and south poles may be positioned along the longitudinal axis (1020) of the control element (1026). In the configuration shown, the south pole faces the proximal end of the control element (1016) (i.e., the left side as depicted in FIG. 10B) and the north pole faces the distal end of the control element (1016) (i.e., the right side as depicted in FIG. 10B).

In use, the attractive force between the control element (1016) and the magnetic element (1012) may move the grasper (1000) toward the control element (1016) such that the longitudinal axis (1014) of the grasper is substantially parallel to the longitudinal axis (1020) of the control element. More specifically, the north and south poles of the magnetic element (1012) in the grasper (1000) may be attracted to the south and north poles, respectively, of the magnetic element (1024) in the control element (1016). In this variation, the magnetic element (1012) of the grasper (1000) is of a sufficient length, or is spread along the grasper across a sufficient length, to cause both the proximal and distal ends (1010, 1008) of the grasper (1000) to be drawn to the control element (1016) and the cavity wall (1022). In this configuration, the longitudinal axis (1014) of the grasper (1000) may be substantially parallel to both the longitudinal axis (1020) of the surface of the cavity wall such that the first and second jaws (1002, 1004) are near the cavity wall. Once in the parallel configuration, the direction of the jaws may be manipulated by rotating the control element, which may in turn cause rotation of the magnetic element (1012) in the grasper (1000). Additionally, if the control element (1016) is moved relative to the cavity wall (1022) (e.g., moving the control element (1016) along the exterior of the body), the grasper (1000) may be moved relative to the cavity wall by a corresponding amount by the attractive forces between the magnetic element (1024) and the control element (1012).

FIG. 10C depicts another variation of a system for grasping tissue comprising the grasper (1000) depicted in FIG. 10A and a control element (1026). In this variation, the control element (1026) may comprise a first magnetic element (1028) and a second magnetic element (1030). As shown there, the first and second magnetic elements (1028, 1030) may be magnets having north and south poles. The first and second magnetic elements (1028, 1030) may be oriented such that their poles are perpendicular to the longitudinal axis (1020) of the control element (1016) and the cavity wall (1024), and have opposite polarities.

For example, as shown in FIG. 10C, the first magnetic element (1028) may be oriented such that its north pole is anteriorly positioned and its south pole is posteriorly positioned, while the second magnetic element (1030) may be oriented so that its north pole is posteriorly positioned and its south pole is anteriorly positioned. In use, the first magnetic element (1028) may attract the north pole of the magnetic element (1012) of the grasper (1000) and the second magnetic element (1030) may attract the south pole of the magnetic element (1012) of the grasper (1000). Additionally, if the control element (1026) is moved or rotated relative to the cavity wall (1022) (e.g., moving or rotating the control element (1026) along the exterior of the body), the grasper (1000) may be moved or rotated relative to the cavity wall by a corresponding amount by the attractive forces between the magnetic elements (1028, 1030) and the control element (1012).

It should be appreciated that the configurations of the magnetic elements (1012, 1028, 1030) may be modified. For example, the poles of the first and second magnetic elements (1028, 1030) and the magnetic element (1012) of the grasper (1000) may be rotated such that they face the opposite direction (e.g., the north pole of the first magnetic element (1028) may be posteriorly positioned and the north pole of the second magnetic element (1030) may be anteriorly positioned). The magnetic elements (1012, 1028, 1030) may have any suitable shape, and need not be cylinders as depicted.

Figure 11B:
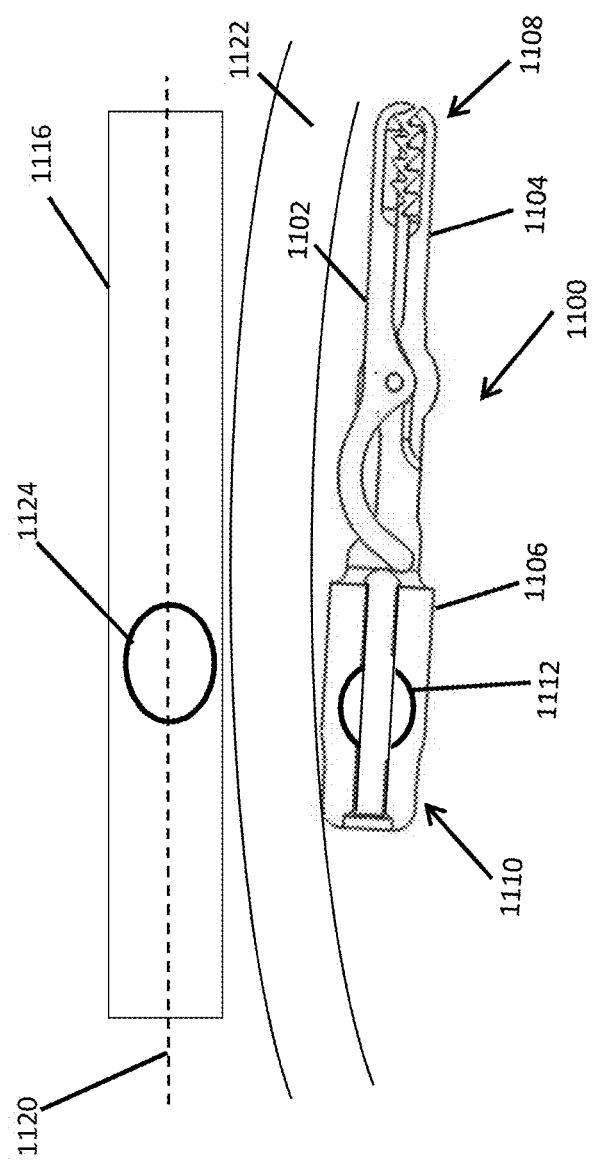
FIGS. 11B and 11C depict a cross-sectional side view and an inside-the-patient view, respectively, of the grasper of FIG. 11A in use with a control element.
Figure 11C:
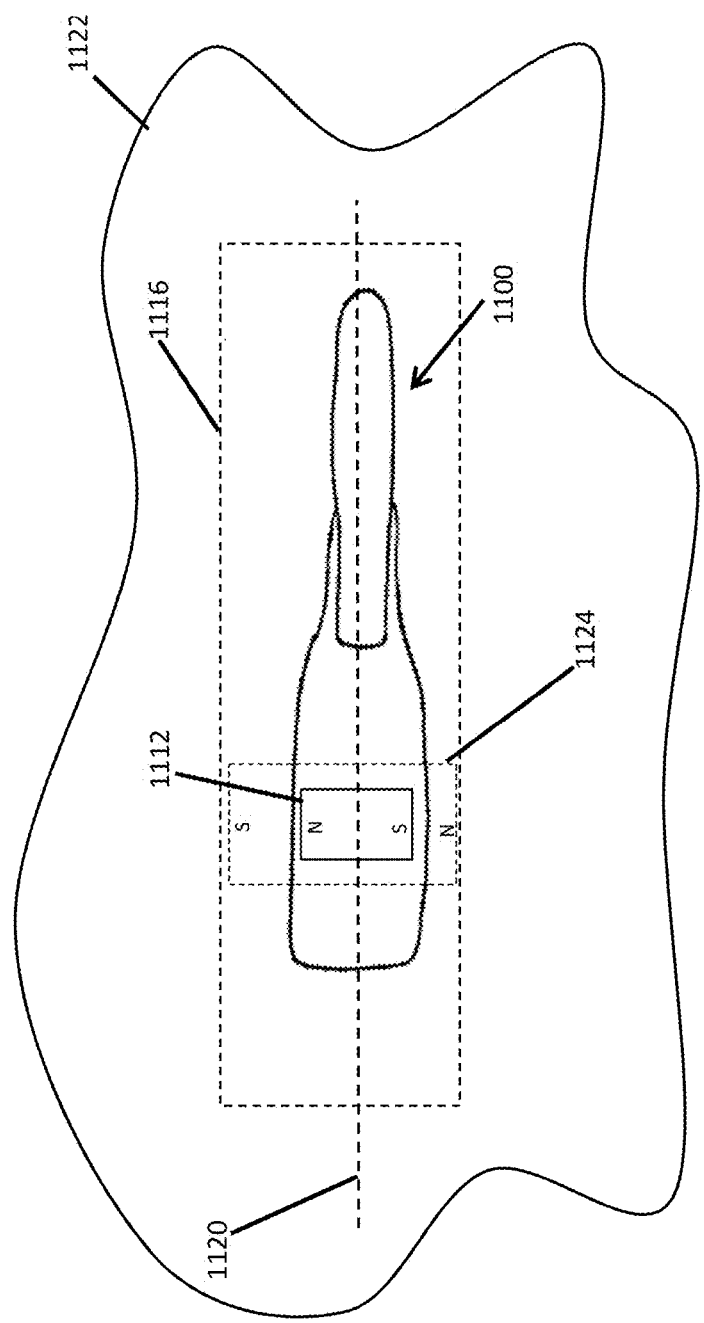

In some embodiments, the grasper and/or the control element may comprise magnetic elements that have poles that are perpendicular to the longitudinal axis of the grasper and the control element, but are parallel to the surface of the cavity wall. For example, FIGS. 11A-11C depict a variation of a system (with like elements labeled as above) comprising a grasper (1100) and a control element (1116), each comprising a magnetic element (1112, 1124). In this variation, the magnetic elements (1112, 1124) may comprise magnets having a north pole and a south pole. The magnetic elements (1112, 1124) may be positioned within the grasper (1100) and the control element (1116) so that their poles are perpendicular to the longitudinal axis of the grasper (1100) and the control element (1116) respectively, and are parallel to the cavity wall (1122).

FIG. 11C may more clearly depict the orientation of the magnetic elements (1112, 1124) in the grasper (1100) and the control element (1116). Shown there is a view from within a patient with a grasper (1100) within the body cavity, and the control element (1116), indicated by dashed lines, outside of the body and above the cavity wall (1122). In use, the north pole of the magnetic element (1112) of the grasper may be attracted to the south pole of the magnetic element (1124) of the control element (1116), which may pull or otherwise move the grasper (1100) toward, and substantially parallel to, the cavity wall (1122).

For example, as depicted in FIG. 11C, if the longitudinal axis (1120) of the control element (1116) is placed along the longitudinal midline of a patient, the north pole of the magnetic element (1124) of the control element (1116) may face the right side of the patient and the south pole of the magnetic element (1124) of the control element (1116) may face the left side of the patient, or vice versa. In this orientation, the north and south poles of the magnetic element (1112) of the grasper (1100) may be attracted to the south and north poles of the magnetic element (1124) of the control element (1116) respectively, which may bring the grasper (1100) into a parallel configuration. While in the parallel configuration, the grasper (1100) may be in a first orientation in which its proximal end (1110) faces a first direction and its distal end (1108) faces a second direction.

The grasper (1100) may be rotated while remaining in the parallel configuration by rotating the control element (1116). For example, the grasper (1100) may be rotated by 180 degrees to place it in a second orientation in which its proximal end (1110) faces the second direction and its distal end (1108) faces the first direction. It should be appreciated that the grasper (1100) may be rotated by any desired angle while remaining in the parallel configuration by rotating the control element (1116). Additionally, if the control element (1116) is moved relative to the cavity wall (1122) (e.g., moving the control element (1116) along the exterior of the body), the grasper (1100) may be moved relative to the cavity wall by a corresponding amount by the attractive forces between the magnetic element (1112) and the control element (1116).

It should be appreciated that a visualization device such as a camera and/or light source may also have a similar configuration of magnetic elements as described with respect to graspers in FIGS. 8A-11C. For example, a visualization device having a similar configuration of magnetic elements as grasper (800) may be used with a control element (816) similar to as shown in FIGS. 8A-8B in order to hold and/or move a visualization device in a perpendicular or angled configuration with respect to the control element and/or the wall of a patient's body cavity. For example, a visualization device may comprise a magnetic element comprising a magnet with north and south poles oriented axially within the visualization device, such that the poles are positioned along a longitudinal axis of the visualization device, as described above with respect to grasper (800). Control element (816) may then be used to control the position and/or movement of the visualization device similarly as described with respect to the grasper (800). As another example, a visualization device having similar configuration of magnetic elements as grasper (1000) and may be used with a control element (1000) similar to as shown in FIGS. 10A-10B in order to hold and/or move the visualization device in a parallel configuration, as described in more detail with respect to grasper (1000).

As mentioned above, in some variations, the grasper may comprise more than one magnetic element. A visualization device (e.g., camera, light source) may similarly comprise more than one magnetic element. Using a grasper (or visualization device) with multiple magnetic elements may provide more control over the movement of the grasper, especially with respect to relative locations of the proximal and distal ends of the grasper (or visualization device). For instance, utilizing a grasper (or visualization device) with multiple magnets may make it easier to rotate the distal end of the grasper (or visualization device) relative to its proximal end and may allow for better control over the grasper (or visualization device) once it is in the parallel configuration. Additionally, employing a grasper (or visualization device) with multiple magnetic elements may make it easier to attract the proximal and/or distal end of the grasper (or visualization device) to the control element (e.g., by repelling the opposite end) and/or control the angle at which the grasper (or visualization device) approaches the control dement and/or tissue (e.g., perpendicular, parallel, any angle between perpendicular and parallel).

Figure 12A:
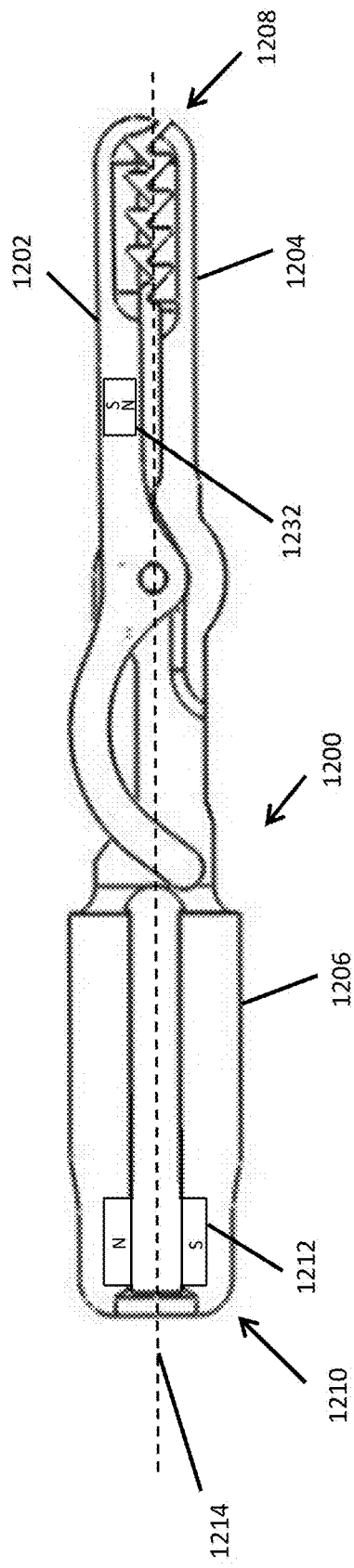
FIG. 12A depicts a cross-sectional side view of another illustrative variation of a grasper described here.
Figure 12B:
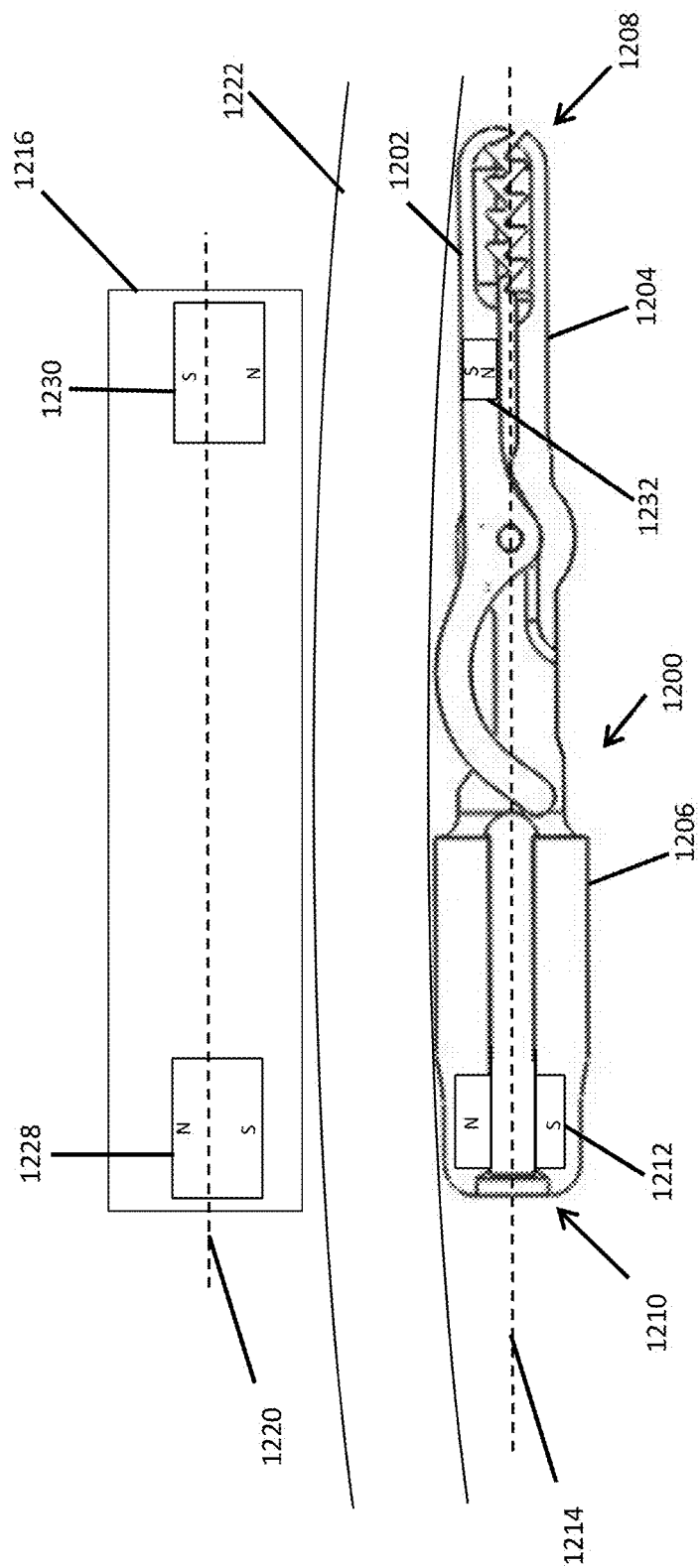
FIGS. 12B and 12C depict a cross-sectional side view and an inside-the-patient view, respectively, of the grasper of FIG. 12A in use with a control element.
Figure 12C:
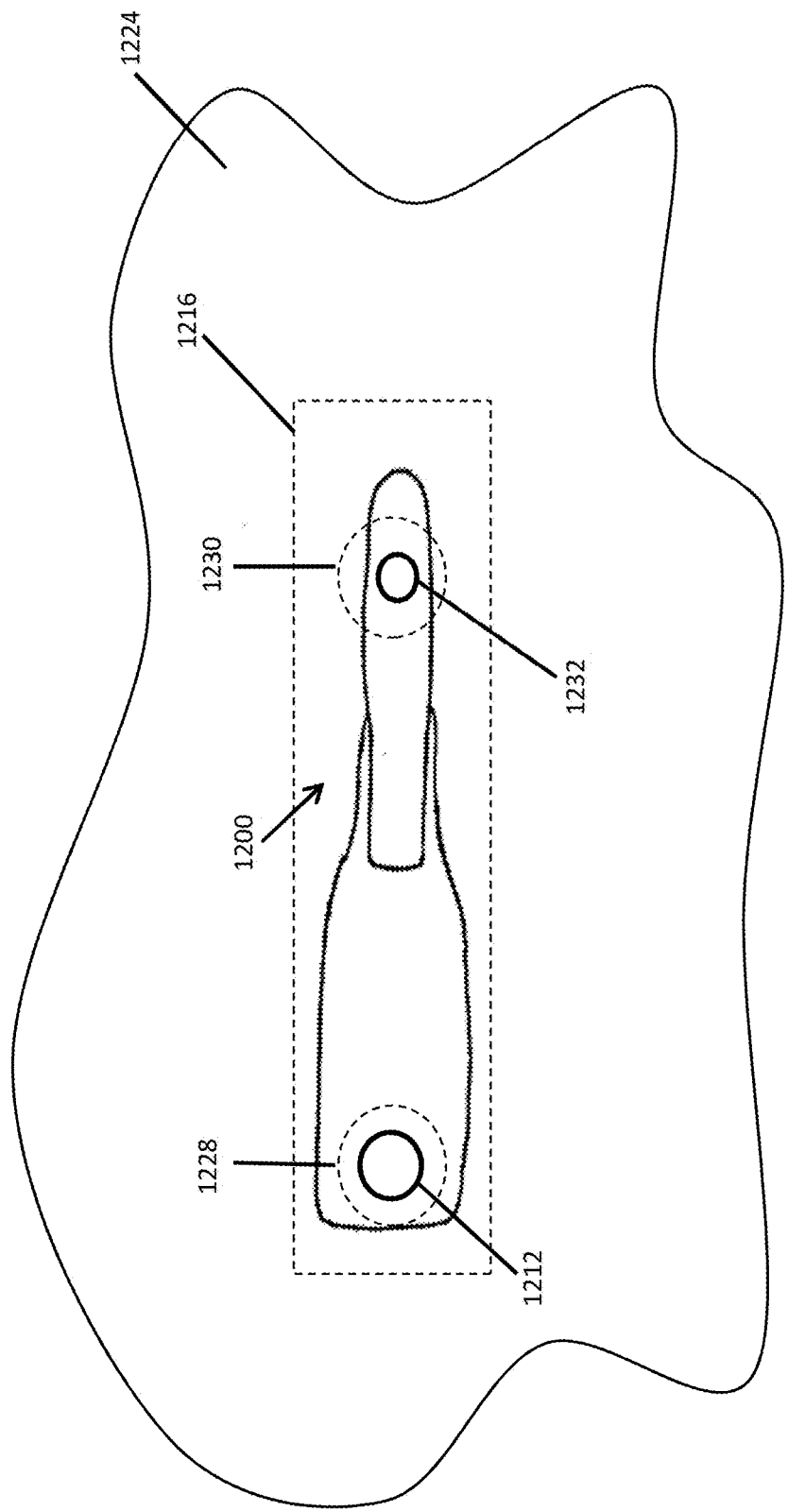

FIGS. 12A-12C depict a variation of the systems described here comprising a grasper (1200) with two magnetic elements (1212, 1232) and a control element (1206). As shown there, the grasper (1200) may comprise a first jaw (1202), a second jaw (1204), a main body (1206), a proximal end (1210), a distal end (1208), a longitudinal axis (1214), a first magnetic element (1212), and a second magnetic element (1232). The first magnetic element (1212) may be located at the proximal end (1210) of the grasper (1200) in the main body (1206), and the second magnetic element (1232) may be located distal to the first magnetic element (1212), for example, in the first jaw (1202). As mentioned above, the first and second magnetic elements (1212, 1232) may comprise magnets having north and south poles. As shown in FIGS. 12A and 12B, the first and second magnetic elements (1212, 1232) may be oriented such that the poles of the first and second magnetic elements (1212, 1232) may be substantially perpendicular to the longitudinal axis (1214) of the grasper (1200) and the cavity wall (1222). For example, the poles of the magnetic elements (1212, 1232) may face posteriorly (toward the cavity wall (1222)) and anteriorly (away from the cavity wall (1222)) when the longitudinal axis (1214) of the grasper (1200) is substantially parallel to the longitudinal axis of a patient.

The first and second magnetic elements (1212, 1232) may be located at any suitable place on or within the grasper (1200), and need not be located as depicted. However, in some instances, it may be desirable to place the first and second magnetic elements (1212, 1232) as close to the proximal and distal ends (1210, 1208) of the grasper as possible, as doing so may assist in steering or otherwise controlling the grasper (1200).

Additionally or alternatively, in instances in which the magnetic elements (1212, 1232) may exert forces on each other, placing them farther away from each other, or with more non-magnetic material between them, may decrease any unwanted effect they may have on each other and/or on the grasper (1200). The First and second magnetic elements (1212, 1232) may have any suitable cross-sectional shape, for example, circle, square, oval, rectangle, hexagon, and the like, and need not comprise the same cross-sectional shape.

FIGS. 12B and 12C depict a cross-sectional side view and an inside-the-patient view, respectively, of the grasper (1200) within the body. The grasper (1200) may be used with a control element (1216) that also comprises two magnetic elements including a first magnetic element (1228) and a second magnetic element (1230). The first and second magnetic elements (1228, 1230) may be located at the proximal and distal ends of the control element (1216) respectively, and the control element (1216) may comprise non-magnetic material between the first and second magnetic elements (1228, 1230). In some variations, the poles of the first and second magnetic elements (1228, 1230) of the control element (1216) may be perpendicular to the longitudinal axis (1220) of the control element (1216) and the cavity wall (1222). While the magnetic elements (1228, 1230) are depicted at the proximal and distal ends of the control element (1216), they need not be. The magnetic elements (1228, 1230) may be located anywhere on or within the control element (1216). Alternatively, while the control element (1216) is depicted with two magnetic elements (1228, 1230), in some variations, it may only comprise one magnetic element.

In use, the opposite poles of the first and second magnetic elements (1212, 1232) in the grasper (1200) and the first and second magnetic elements (1228, 1230) in the control element (1216) may be attracted to each other, respectively, which may place the grasper (1200) in the parallel configuration, as shown in FIGS. 12B and 12C. As depicted there, the north pole of the first magnetic element (1212) in the grasper (1200) faces anteriorly (i.e., toward the cavity wall (1222) and the control element (1216)), and the north pole of the second magnetic element (1232) in the grasper (1200) faces posteriorly (i.e., away from the cavity wall (1222) and the control element (1216)). The north pole of the first magnetic element (1228) in the control element (1216) faces anteriorly (i.e., away from the cavity wall (1222)), and the north pole of the second magnetic element (1230) in the control element (1216) faces posteriorly (e.g., toward the cavity wall (1222)). If the control element (1216) is moved relative to the cavity wall (1222) (e.g., moving the control element (1216) along the exterior of the body), the grasper (1200) may be moved relative to the cavity wall by a corresponding amount by the attractive forces between the magnetic element (1212) and the control element (1216).

While the first and second magnetic elements in both the grasper (1200) and the control element (1216) are depicted with the poles of the first magnetic element facing the opposite direction as the poles of the second magnetic element, this need not be the case. For example, the first and second magnetic elements may be positioned such that the north poles of both of the magnetic elements face the same direction.

Additionally, while depicted as permanent magnets comprising north and south poles, the magnetic elements (1212, 1232) need not be and may comprise any of the magnetic elements described above that result in attractive forces between the magnetic elements (1212, 1232) in the grasper (1200) and the magnetic elements (1228, 1230) in the control element (1216). For example, in some instances, either (but not both) the magnetic element (1212) in the grasper (1200) or the magnetic element (1228) in the control element (1216) may be a material attracted to a magnetic field but may not generate a magnetic field (e.g., a ferrimagnetic or ferromagnetic material); similarly, either (but not both) the magnetic element (1232) in the grasper (1200) or the magnetic element (1230) in the control element (1216) may be a material attracted to a magnetic field but may not generate a magnetic field (e.g., a ferrimagnetic or ferromagnetic material).

Figure 12D:
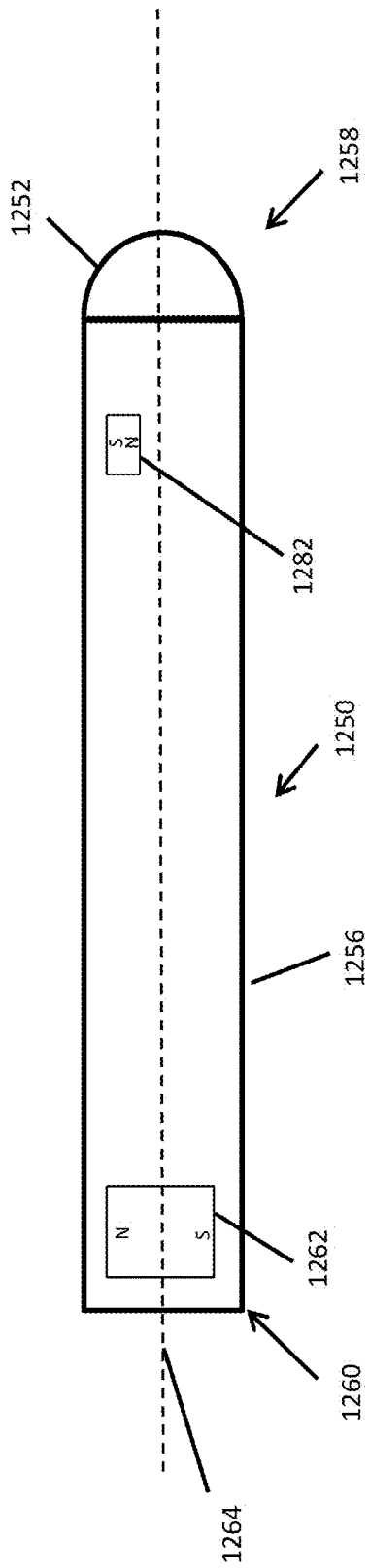
FIG. 12D depicts a cross-sectional side view of another illustrative depiction of a camera described here.

FIG. 12D depicts a variation of the systems described here comprising a camera (1250) with two magnetic elements (1262, 1282). As shown there, the camera (1250) may comprise a lens (1252), a main body (1256), a proximal end (1260), a distal end (1258), a longitudinal axis (1264), a first magnetic element (1262), and a second magnetic element (1282). It should be appreciated that the main body of the camera may have any suitable shape, and that the lens may have any suitable configuration and need not be located at the distal end of the camera (e.g., the lens may be located along the main body and be facing radially outward). The first magnetic element (1262) may be located at the proximal end (1260) of the camera (1250) in the main body (1256), and the second magnetic element (1282) may be located distal to the first magnetic element (1262), for example, adjacent the lens (1252). The first and second magnetic elements (1262, 1282) may comprise magnets having north and south poles.

As shown in FIG. 12D, the first anti second magnetic elements (1262, 1282) may be oriented such that the poles of the first and second magnetic elements (1262, 1282) may be substantially perpendicular to the longitudinal axis (1264) of the camera (1250). The first and second magnetic elements (1262, 1282) may be located at any suitable place on or within the camera (1250), and need not be located as depicted. However, in some instances, it may be desirable to place the first and second magnetic elements (1262, 1282) as close to the proximal and distal ends (1260, 1258) of the camera (1250) as possible, as doing so may assist in positioning or otherwise controlling the camera (1250).

Additionally or alternatively, in instances in which the magnetic elements (1262, 1282) may exert forces on each other, placing them farther away from each other, or with more non-magnetic material between them, may decrease any unwanted effect they may have on each other and/or on the camera (1250). The first and second magnetic elements (1262, 1282) may have any suitable cross-sectional shape, for example, circle, square, oval, rectangle, hexagon, and the like, and need not comprise the same cross-sectional shape.

Additionally, while depicted as permanent magnets comprising north and south poles, the magnetic elements (1262, 1282) need not be and may comprise any of the magnetic elements described above that result in attractive forces between the magnetic elements (1262, 1282) in the camera (1250). For example, in some instances, the magnetic elements (1262, 1282) in the camera (1250) may be a material attracted to a magnetic field but may not generate a magnetic field (e.g., a ferrimagnetic or ferromagnetic material).

The camera (1250) may be used with a control element in a similar manner as described with respect to grasper (1200) and control element (1216) in FIGS. 12B-12C. For example, camera (1250) may be used with control element (1216) such that the opposite poles of the first and second magnetic elements (1262, 1282) in the camera (1250) and the first and second magnetic elements (1228, 1230) in the control element (1216) may be attracted to each other, respectively, which may place the camera (1250) in the parallel configuration, similarly to the configuration of the grasper (1200) shown in FIGS. 12B and 12C. That is, the north pole of the first magnetic element (1262) in the camera (1250) may face anteriorly (i.e., toward the cavity wall (1222) and the control element (1216)), and the north pole of the second magnetic element (1282) in the camera (1250) may face posteriorly (i.e., away from the cavity wall (1222) and the control element (1216)). The north pole of the first magnetic element (1228) in the control element (1216) may face anteriorly (i.e., away from the cavity wall (1222)), and the north pole of the second magnetic element (1230) in the control element (1216) may face posteriorly (e.g., toward the cavity wall (1222)). If the control element (1216) is moved relative to the cavity wall (1222) (e.g., moving the control element (1216) along the exterior of the body), the camera (1250) may be moved relative to the cavity wall by a corresponding amount by the attractive forces between the magnetic element (1262) and the control element (1216).

Figure 19A:
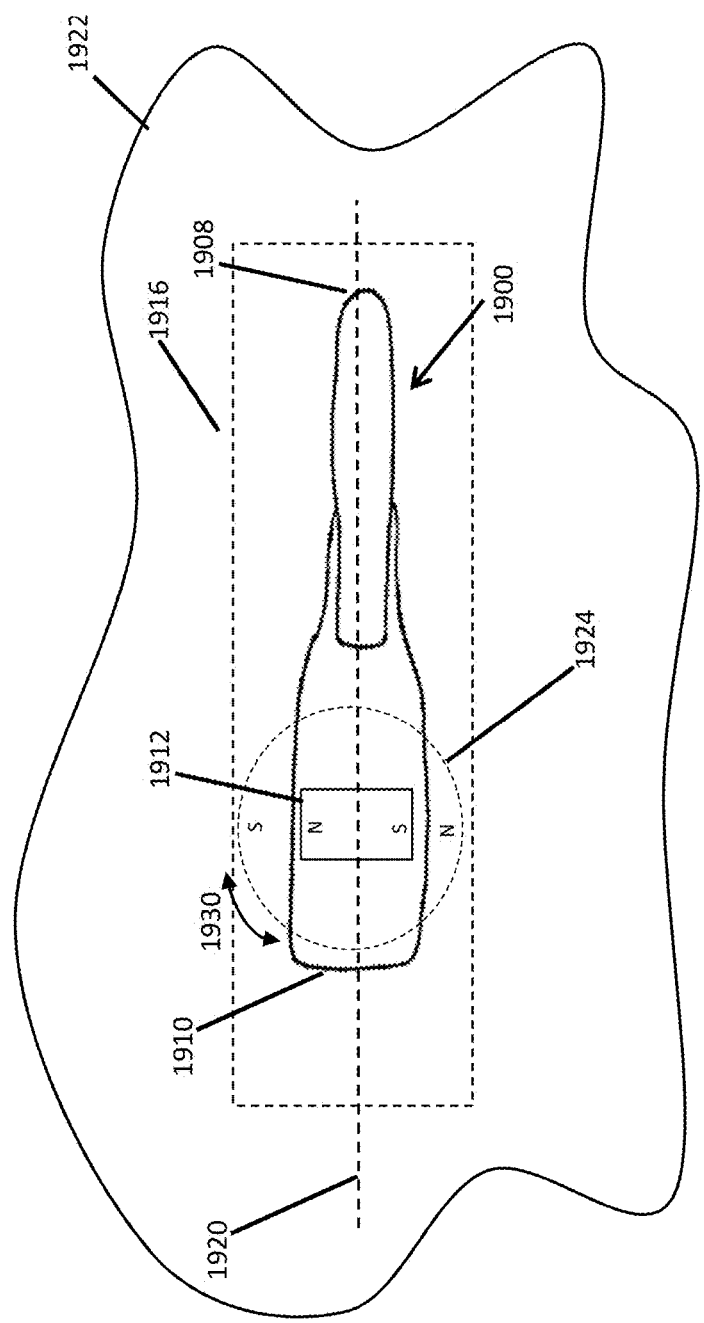
FIGS. 19A-19B depict inside-the-patient views of an illustrative variation of a grasper in use with a control element.
Figure 19B:
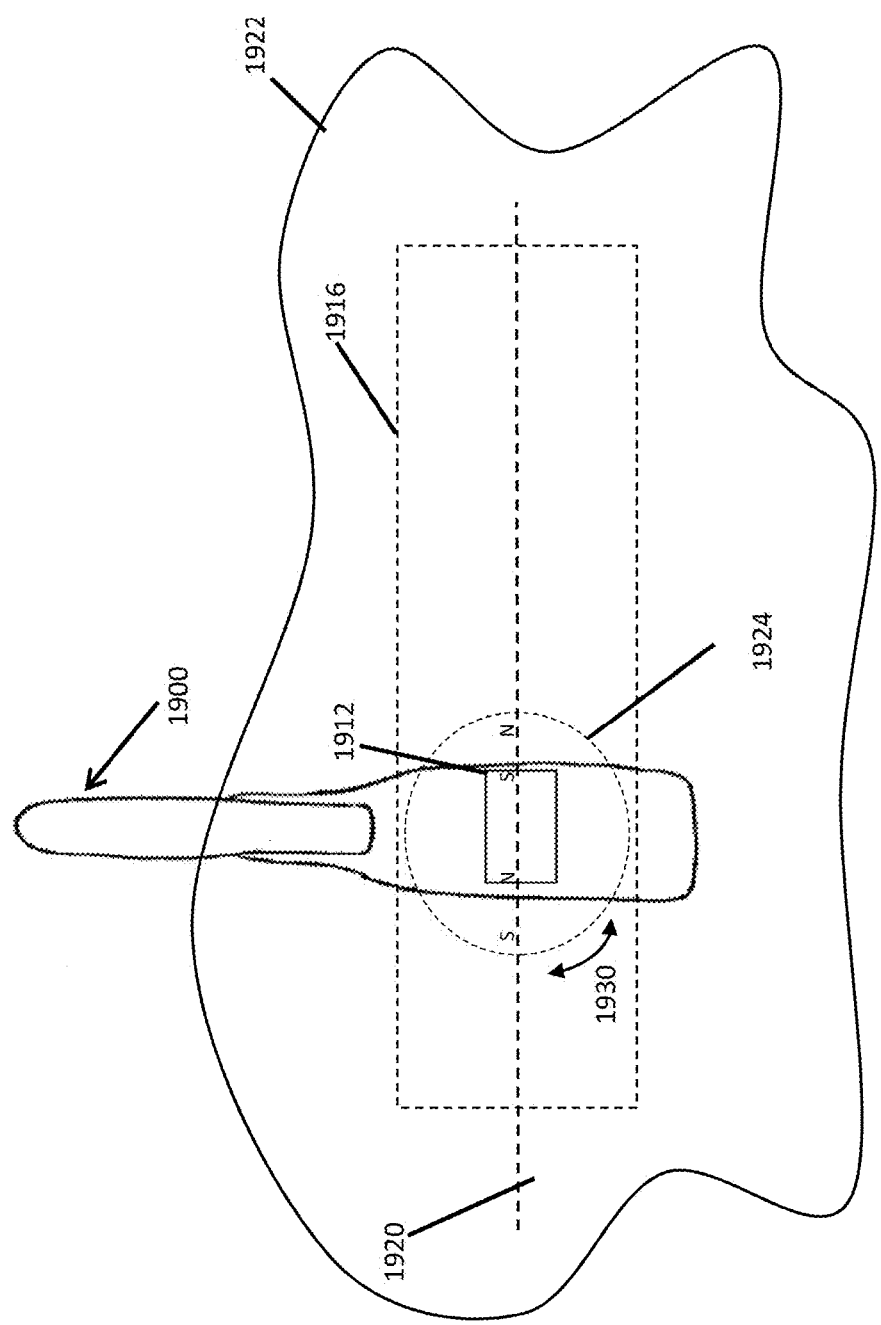

In yet other variations, an orientation of a grasper or visualization device (e.g., camera, light source) may be manipulated by a control element located outside of the body. In some variations, the grasper or visualization device and the control element may be configured to yield a desired change in position and/or orientation of the grasper or visualization device without movement of the control element relative to the body. For example, as shown in FIGS. 18A-18B, a control element (1816) and a grasper (1800) may be configured to rotate the grasper between a perpendicular configuration (FIG. 18A) and a parallel configuration (FIG. 18B) relative to the internal wall of the patient's body cavity (1822) and/or the surface of the control element without moving the control element (1816) relative to the body cavity (1822). As another example, FIGS. 19A-19B illustrates a 90 degree yaw rotation of a grasper (1900) about an axis perpendicular to the grasper (1900) through rotation (1930) of a magnetic housing (1924) while the control element (1916) itself remains stationary externally on a patient body cavity wall (1922).

In some surgical procedures, or at times during a surgical procedure, it may be desirable for the grasper or visualization device to move between a perpendicular or angled configuration and a substantially parallel configuration with respect to the wall of a patient's body cavity (e.g., an abdominal cavity) through manipulation of a control element. FIG. 18A depicts a variation of a system comprising a control element (1816) and a grasper (1800) positioned in a perpendicular configuration relative to the cavity wall (1822). FIG. 18B depicts the grasper (1800) positioned in a substantially parallel configuration relative to the cavity wall (1822).

As shown in FIG. 18A, the grasper (1800) may comprise a first jaw (1802) rotatably coupled to a main body (1806), a second jaw (1804) fixed relative to the main body (1806), a proximal end (1810), a distal end (1808), and a magnetic element (1812). In this variation, the magnetic element (1812) may be located in or on the main body (1806) at or towards a proximal end (1810) of the grasper (1800). When the grasper (1800) is exposed to a force generated by control element (1816) comprising a magnet (1824), the proximal end (1810) of the grasper (1800) may be attracted to the control element (1816). The remainder of the grasper (1800) (aside from the magnetic element), including, for example, the remainder of the main body (1806) and the first and second jaws (1802, 1804), may in some instances comprise a non-magnetic material. In other instances, all or a portion of the remainder of the main body (1806) and the first and second jaws (1802, 1804) may comprise a second magnetic element that is ferromagnetic, that experiences a repulsive force when placed close to the control element (1816), for example, a diamagnetic material (e.g., copper, zinc, lead, and the like), or that is a permanent magnet having a polarity causing it to be repelled by the control element.

As shown in FIG. 18A, the magnetic element (1812) may comprise a magnet with north and south poles oriented axially within the grasper (1800) such that the poles are positioned along a longitudinal axis of the grasper (1800). More particularly, the south pole of the magnetic element (1812) faces a proximal end (1810) of the grasper (1800) and the north pole faces a distal end (1808) of the grasper (1800). Shown in FIG. 18A is the grasper (1800) within the body and separated from a control element (1816) by the body cavity wall (1822). The control element (1816) is provided outside the body and comprises a longitudinal axis (1820). It should be appreciated that the longitudinal axis (1820) of the control element (1816) need not be substantially parallel to the cavity wall (1822), and may be provided perpendicular to or at an angle relative to the cavity wall (1822). In other words, the shape of the control element (1816) is not particularly limited. Likewise, the magnet (1824) may have any suitable cross-sectional shape, for example, circle, square, oval, triangle, rectangle, hexagon, and the like.

The control element may comprise a control element housing (1816) enclosing a magnet housing (1824) comprising a magnet. As discussed below, the magnet housing (1824) may be rotatable (arrow 1830) relative to the control element housing (1816). In FIG. 18A, the magnet housing (1824) is positioned relative to the control element housing (1816) in a first configuration such that the poles of the magnetic material face toward and away from the cavity wall (1822). As depicted, the north pole of the magnetic material faces downward, or toward the cavity wall (1822), and the south pole of the magnetic material faces upward, or away from the cavity wall (1822). In some instances, the magnet housing (1824) in this position may be rotated (1830) 90° relative to the control element housing (1816) to orient the magnet housing (1824) in a configuration perpendicular to the first configuration where the north and south poles are aligned along a longitudinal axis (1820) of the control element. Of course, the magnet housing (1824) may be rotated (1830) by other amounts, such as show n in FIG. 18B as discussed in further detail below.

While the control element housing (1816) is depicted as enclosing the magnet housing (1824), it need not be, so long as the magnet housing (1824) is rotatable relative to the control element housing (1816). Furthermore, while the magnet housing (1824) is depicted as having a circular cross-sectional shape, the magnet housing (1824) may comprise any shape allowing rotation or other reorientation of the magnet housing (1824) relative to the control element housing (1816), in order to change the magnetic field applied to the grasper (1800). Similarly, the magnetic material within the magnet housing (1824) may comprise any desirable shape within the magnet housing (1824). In some variations, the magnetic material may be provided without a magnet housing, and the magnetic material may be rotatable relative to the control element housing. In some variations, the control element housing (1816) may comprise a combination of one or more non-magnetic materials (e.g., plastics, paramagnetic materials such as titanium, and the like) and one or more magnets.

As depicted in FIG. 18A, the attractive forces between the control element in a first position as shown and the magnetic element (1812) may move the proximal end (1810) of the grasper (1800) toward the control element housing (1816). More specifically, the south pole of the magnetic element (1812) in the grasper (1800) may be attracted to the north pole of the magnet housing (1824). The attractive forces between the magnetic element (1812) in the grasper (1800) and the control element housing (1816) may cause the proximal end (1810) of the grasper (1800) to be attracted to and move toward the control element housing (1816) and the cavity wall (1822), while the distal end (1808) of the grasper (1800) may be repelled by and move away from the control element housing (1816) and the cavity wall (1822). Accordingly, the attractive forces between the magnetic element (1812) and the control element housing (1816) may cause the grasper (1800) to rotate and/or move into a position in which its longitudinal axis is transverse, and substantially perpendicular to, the surface of the cavity wall (1822) and longitudinal axis (1820) of the control element housing (1816). In this position, the first and second jaws (1802, 1804) of the grasper (1800) may be facing away from the cavity wall (1822).

Instead of the first position, shown in FIG. 18A, it may be desirable for the grasper (1800) to move to and/or be held in a different orientation (e.g., such that its longitudinal axis lies parallel to the cavity wall (1822)), as depicted in FIG. 18B. In particular, FIG. 18B depicts a second configuration of the magnet housing (1824) where the north and south poles are oriented along the longitudinal axis (1820) of the control element housing (1816). In the second configuration shown, the north pole of the magnetic element (1812) faces the proximal end of the control element housing (1816) (i.e., the left side as depicted in FIG. 18B) and the south pole of the magnetic element (1812) faces the distal end of the control element housing (1816) (i.e., the right side as depicted in FIG. 18B).

In the second configuration, the attractive force between the control element housing (1816) and the magnetic element (1812) may move the grasper (1800) toward the control element housing (1816) in a second position such that the grasper (1800) may be substantially parallel to the longitudinal axis (1820) of the control element housing (1816). More specifically, the north and south poles of the magnetic element (1812) in the grasper (1800) may be attracted to the south and north poles, respectively, of the magnet in the magnet housing (1824). As such, as the magnet housing (1824) of the control element housing (1816) is rotated from a first configuration (FIG. 18A) to the second configuration (FIG. 18B), the change in the magnetic field will likewise rotate the grasper (1800) from a first position perpendicular to the cavity wall (1822) to a second position parallel to the cavity wall (1822).

It should be appreciated that the grasper (1800), the magnetic element (1812), and the control element housing (1816) may be configured such that the attractive forces between the magnetic element (1812) and the control element housing (1816) cause the grasper (1800) to rotate and/or move into a position in which the longitudinal axis of the grasper (1800) is located at an angle that is less than 90 degrees with respect to the surface of the cavity wall (1822) due to factors such as the orientation and strength of the magnetic elements in the grasper (1800) and the control element housing (1816), the material of the grasper (1800), gravity, and/or the tension force from organs or other tissue held by the grasper (1800). The grasper (1800) and the control element housing (1816) may be configured to have an attractive force between them that places the grasper (1800) in a desired angular orientation considering these variables.

It should further be appreciated that a change in configuration of a grasper may be provided through a combination of manipulation of the entire control element housing (1816) relative to the grasper and of a magnet relative to the control element housing.

As another example, FIG. 18C depicts a variation of a system comprising a control element (1816) and a visualization device comprising a camera (1850) positioned in a perpendicular configuration relative to the cavity wall (1822). FIG. 18B depicts the camera (1850) positioned in a substantially parallel configuration relative to the cavity wall (1822).

As shown in FIGS. 18C-18D, camera (1850) may comprise a lens (1852) coupled to a main body (1856), a proximal end (1860), a distal end (1858), and a magnetic element (1862). In this variation, the magnetic element (1862) may be located in or on the main body (1856) at or towards a proximal end (1860) of the camera (1850). It should be appreciated that the main body of the camera may have any suitable shape, and that the lens may have any suitable configuration and need not be located at the distal end of the camera (e.g., the lens may be located along the main body and be facing radially outward). When the camera (1850) is exposed to a force generated by control element (1816) as described above, the proximal end (1860) of the camera (1850) may be attracted to the control element (1816). The remainder of the camera (1850) (aside from the magnetic element), including, for example, the remainder of the main body (1856) and the lens (1852), may in some instances comprise a non-magnetic material. In other instances, all or a portion of the remainder of the main body (1856) may comprise a second magnetic element that is ferromagnetic, or that is a permanent magnet as described.

As shown in FIG. 18C, the magnetic element (1862) may comprise a magnet with north and south poles oriented axially within the camera (1850) such that the poles are positioned along a longitudinal axis of the camera (1850). More particularly, the south pole of the magnetic element (1862) faces a proximal end (1860) of the camera (1850) and the north pole faces a distal end (1858) of the camera (1850). Shown in FIG. 18C is the camera (1850) within the body and separated from a control element (1816) by the body cavity wall (1822). It should be noted that description of the structure and operation of control element (1816) in FIGS. 18C and 18D is similar to FIGS. 18A and 18B and is omitted for the sake of brevity.

As depicted in FIG. 18C, the attractive forces between the control element in a first position as shown and the magnetic element (1862) may move the proximal end (1860) of the camera (1850) toward the control element housing (1816). More specifically, the south pole of the magnetic element (1862) in the camera (1850) may be attracted to the north pole of the magnet housing (1824). The attractive forces between the magnetic element (1862) in the camera (1850) and the control element housing (1816) may cause the proximal end (1860) of the camera (1850) to be attracted to and move toward the control element housing (1816) and the cavity wall (1822), while the distal end (1858) of the camera (1850) may be repelled by and move away from the control element housing (1816) and the cavity wall (1822). Accordingly, the attractive forces between the magnetic element (1862) and the control element housing (1816) may cause the camera (1850) to rotate and/or move into a position in which its longitudinal axis is transverse, and substantially perpendicular to, the surface of the cavity wall (1822) and longitudinal axis (1820) of the control element housing (1816). In this position, the lens (1852) of the camera (1850) may be facing away from the cavity wall (1822).

Instead of the first position, shown in FIG. 18C, it may be desirable for the camera (1850) to move to and/or be held in a different orientation (e.g., such that its longitudinal axis lies parallel to the cavity wall (1822)), as depicted in FIG. 18D. In particular, FIG. 18D depicts a second configuration of the magnet housing (1824) where the north and south poles are oriented along the longitudinal axis (1820) of the control element housing (1816). In the second configuration shown, the north pole of the magnetic element (1862) faces the proximal end of the control element housing (1816) (i.e., the left side as depicted in FIG. 18D) and the south pole of the magnetic element (1812) faces the distal end of the control element housing (1816) (i.e., the right side as depicted in FIG. 18D).

In the second configuration, the attractive force between the control element housing (1816) and the magnetic element (1862) may move the camera (1850) toward the control element housing (1816) in a second position such that the camera (1850) may be substantially parallel to the longitudinal axis (1820) of the control element housing (1816). More specifically, the north and south poles of the magnetic element (1862) in the camera (1850) may be attracted to the south and north poles, respectively, of the magnet in the magnet housing (1824). As such, as the magnet housing (1824) of the control element housing (1816) is rotated from a first configuration (FIG. 18C) to the second configuration (FIG. 18D), the change in the magnetic field will likewise rotate the camera (1850) from a first position perpendicular to the cavity wall (1822) to a second position parallel to the cavity wall (1822).

It should be appreciated that the camera (1850), the magnetic element (1862), and the control element housing (1816) may be configured such that the attractive forces between the magnetic element (1862) and the control element housing (1816) cause the camera (1850) to rotate and/or move into a position in which the longitudinal axis of the camera (1850) is located at an angle that is less than 90 degrees with respect to the surface of the cavity wall (1822) due to factors such as the orientation and strength of the magnetic elements in the camera (1850) and the control element housing (1816), the material of the camera (1850), gravity, and/or the force from organs or other tissue abutting the camera (1850). The camera (1850) and the control element housing (1816) may be configured to have an attractive force between them that places the camera (1850) in a desired angular orientation considering these variables.

It should further be appreciated that a change in configuration of a visualization device may be provided through a combination of manipulation of the entire control element housing relative to the visualization device and of a magnet relative to the control element housing.

In some variations, the grasper and/or the control element may comprise magnetic elements that have poles that are perpendicular to the longitudinal axis of the grasper and the control element (as shown in FIGS. 19A-19B). In these variations, the grasper and the control element may be configured to yield a desired change in position and/or rotation of the grasper. For example, in some instances, the control element and the grasper may be configured such that the control element can cause the grasper to rotate about an axis perpendicular to a cavity wall to provide the grasper yaw rotation where, for example, the grasper maintains a parallel configuration relative to the internal wall of the patient's body cavity or the surface of the control element. In other instances, the control element may be configured to cause roll rotation of the grasper about the longitudinal axis of the grasper while the grasper is perpendicular to the cavity wall.

For example, FIGS. 19A-19B depict a variation of a system comprising a grasper (1900) comprising a magnetic element (1912). The control element may comprise a control element housing (1916) enclosing a magnet housing (1924) comprising a magnet. In this variation, the magnetic element (1912) and magnet housing (1924) may each comprise magnets each having a north pole and a south pole. The magnetic element (1912) anti magnet housing (1924) may be positioned within the grasper (1900) and the control element housing (1916), respectively, so that their poles are perpendicular to the longitudinal axis (1920) of the grasper (1900) and the control element housing (1916) respectively. As shown in FIGS. 19A-19B, the grasper and control element may be placed such that the poles are parallel to the cavity wall (1922).

FIG. 19A depicts the orientation of the magnetic element (1912) and magnet housing (1924) in the grasper (1900) and the control element housing (1916), respectively. Shown there is a view from within a patient's body cavity. Grasper (1900) is shown within the body cavity, and the control element housing (1916), indicated by dashed lines, is shown outside of the body and above the cavity wall (1922). In use, the north pole of the magnetic element (1912) of the grasper may be attracted to the south pole of the magnet housing (1924) of the control element housing (1916), which may pull or otherwise move the grasper (1900) toward, and substantially parallel to, the cavity wall (1922).

For example, as depicted in FIG. 19A, if the longitudinal axis (1920) of the control element housing (1916) is placed along the longitudinal midline of a patient, the north pole of the magnet housing (1924) of the control element housing (1916) may face the right side of the patient and the south pole of the magnet housing (1924) of the control element housing (1916) may face the left side of the patient, or vice versa. In this orientation, the north and south poles of the magnet housing (1912) of the grasper (1900) may be attracted to the south and north poles of the magnet housing (1924) of the control element housing (1916) respectively, which may bring the grasper (1900) into a parallel configuration.

While in the parallel configuration, the grasper (1900) may be in a first orientation in which its proximal end (1910) faces a first direction and its distal end (1908) faces a second direction. The grasper (1900) may be rotated while remaining in the parallel configuration by rotating (arrow 1930) magnet (1924) relative to the control element housing (1916). For example, the grasper (1900) may be rotated by 180 degrees to place it in a second orientation in which its proximal end (1910) faces the second direction and its distal end (1908) faces the first direction.

As another example, FIG. 19B illustrates the grasper (1900) rotated (1930) by 90 degrees by rotation of the magnet housing (1924) relative to the control element housing (1916) such that the longitudinal axis of the grasper (1900) is perpendicular to the longitudinal axis (1920) of the control element housing (1916). It should be appreciated that the grasper (1900) may be rotated by any desired angle while remaining in the substantially parallel configuration by rotating the magnet housing (1924) relative to the control element housing (1916). Furthermore, the magnet housing (1924) and control element housing (1916) need not have the cross-sectional shapes as depicted in FIGS. 19A-19B, and may have any configuration that allows rotation of the magnet relative to the control element.

It should be appreciated that a visualization device (e.g., camera, light source) and/or control element may also have a similar configuration of magnetic elements as described with respect to the graspers and control elements in FIGS. 19A-19B. In some variations, the visualization device and/or the control element may comprise magnetic elements that have poles that are perpendicular to the longitudinal axis of the visualization device and the control element similar to as shown in FIGS. 19A-19B. In these variations, the visualization device and the control element may be configured to yield a desired change in position and/or rotation of the visualization device. For example, in some instances, the control element and the visualization device may be configured such that the control element can cause the visualization device to rotate about an axis perpendicular to a cavity wall to provide the visualization device yaw rotation where, for example, the visualization device maintains a parallel configuration relative to the internal wall of the patient's body cavity or the surface of the control element. In other instances, the control element may be configured to cause roll rotation of the visualization device about the longitudinal axis of the visualization device while the visualization device is perpendicular to the cavity wall.

Figure 20:
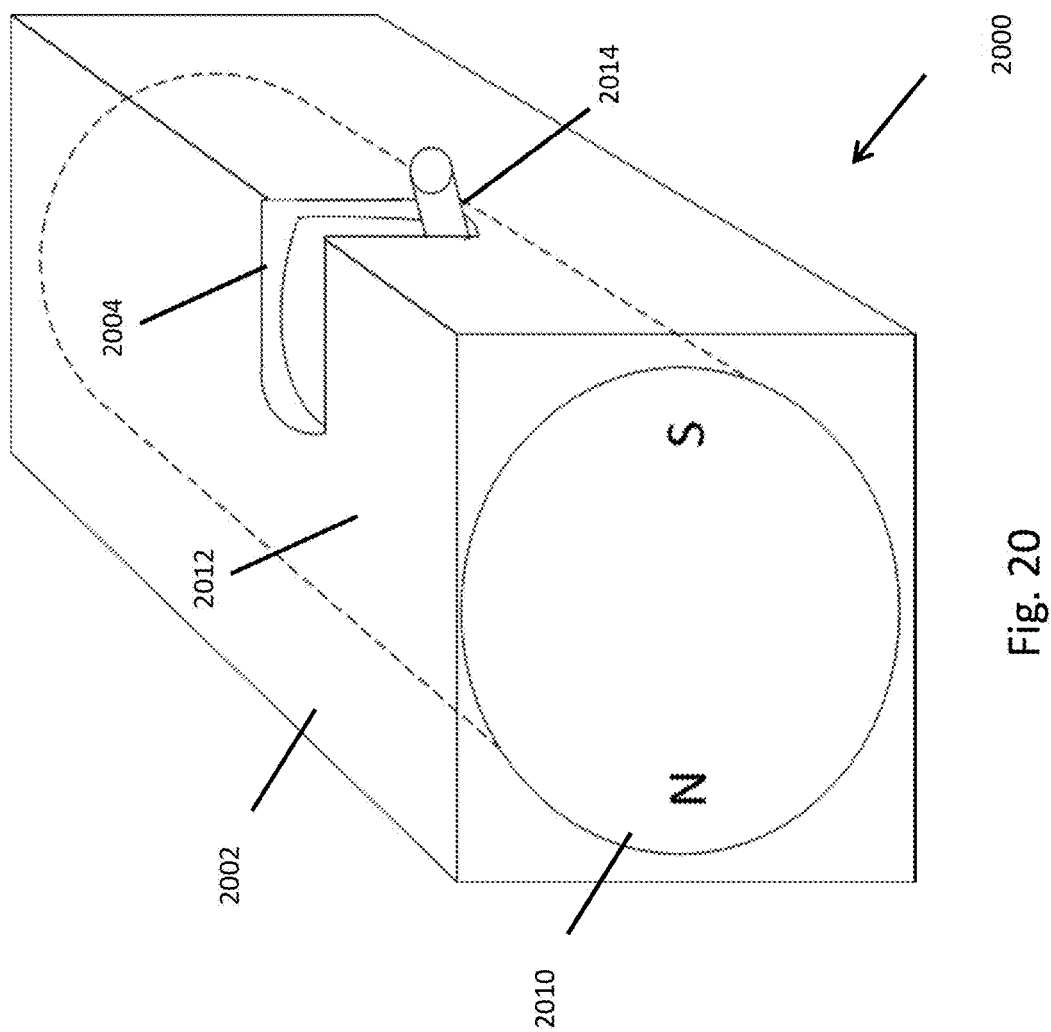
FIG. 20 depicts a perspective view of an illustrative variation of a control element.

FIG. 20 depicts an illustrative variation of a control element providing a variable magnetic field. The control element (2000) comprises a magnet that rotates relative to the control element housing such that the control element may be stationary as the magnetic field applied to a grasper is modified. A control element (2000) may comprise a control element housing (2002) enclosing a magnet housing (2012) comprising a magnet (2010) and a magnet control (2014). Movement of the magnet control (2014) within a control element opening (2004) may provide corresponding rotation of the magnet housing (2012) and in turn the magnet (2010). The magnet (2010) may comprise a diamagnetic material and may comprise opposing north and south poles. The control element housing (2002) may have one or more openings that define a range of motion of the magnet control (2014). In FIG. 20, movement of the magnet control (2014) through its range of motion will rotate the magnet (2010) by 90 degrees to change the direction of the poles.

It should be appreciated that one or more of the magnet (2010) and magnet housing (2012) may comprise a sphere, bar, axially-magnetized cylinder, or a set of magnets. The magnet (2010) illustrated in FIG. 20 may be rotated about a longitudinal axis of the control element (2000). In other variations, the poles may be oriented axially within the control element (2000) such that the poles are positioned along a longitudinal axis of the control element (2000). In still other variations, the magnet (2010) may have additional degrees of freedom. For instance, the magnet housing (2012) may be spherical and the magnet control (2014) may be manipulated to provide three degrees of freedom. If the control element opening (2004) is spherical for example, then the magnet control (2014) may be manipulated like a joystick. It should be appreciated that the magnet housing (2012) and control element housing (2002) may comprise different shapes and/or materials. The magnet (2010) and magnet housing (2012) may comprise any shape that allows rotation and/or movement relative to the control element (2000).

While the variation of the grasper that is described above with respect to FIGS. 6A-6D and FIGS. 7A-7D is depicted in FIGS. 8A-12C, 18A-18B, and 19A-19B, it should be appreciated that any suitable grasper, visualization device, and/or delivery systems described here may be configured with magnetic and non-magnetic materials as described in FIGS. 8A-12D and 18A-19B. Additionally, it should be appreciated that the magnetic and non-magnetic materials described with respect to FIGS. 8A-12D and 18A-19B may be designed to work concurrently with the delivery devices described above, and in some variations, the coupling magnet and the magnetic element may comprise the same material and/or be the same magnet.

II. Methods

The graspers, visualization devices (e.g., cameras, light sources), and systems described herein may be used in minimally invasive procedures. These may include any suitable minimally invasive procedure, such as but not limited to abdominal procedures, thorascopic procedures, bariatric procedures, or urological/gynecological procedures. Generally, as mentioned above, to provide suspension of tissue, a grasper as described herein may be advanced into the body, may be releasably connected to a tissue in the body, and may be suspended using one or more magnetic elements positioned externally to the body to move and suspend the tissue. In some variations, the connection between the grasper and the tissue may be released, and the grasper may be repositioned and reconnected to tissue (either the same tissue or different tissue). In some variations, to provide visualization of a surgical procedure from a desired position and orientation within a body cavity, a visualization device such as a camera and/or light source as described herein may be advanced into the body, and may be suspended using one or more magnetic elements positioned externally to the body.

The grasper may be advanced into the body in any suitable manner. In some variations, the grasper may be advanced into the body through a port as part of a minimally invasive procedure. In some instances, the minimally invasive procedure may be a reduced port technique or single-incision procedure. In some variations, the grasper may be advanced into the body using a delivery device, such as the delivery device (100) described above with respect to FIGS. 1A-1C and 2A-2F. In these variations, the grasper may be releasably coupled to a distal engagement portion of the delivery device, and the distal engagement portion of the delivery device may be advanced into the body to advance and position the grasper within the body.

Once the grasper is positioned in the body, it may be releasably connected to tissue. To connect the grasper to tissue, the grasper may first be placed in an open configuration, in which a first jaw of the grasper is rotated away from a second jaw of the grasper. In some variations, the grasper may be placed in an open configuration using the delivery device carrying the grasper (e.g., by advancing an actuation rod through a barrel portion of the grasper, such as described in more detail above with respect to FIGS. 2A-2F) or by a grasping device which may engage and move the grasper to the open configuration (as described in more detail above). With the grasper in the open configuration, the grasper may be manipulated to position the tissue between the first jaw and the second jaw. The grasper may be returned to a closed configuration, in which the first jaw rotates toward the second jaw to hold the tissue between the jaws. The grasper may then be released from the delivery device and/or grasping device, and these devices may be removed from the body.

Figure 5B:
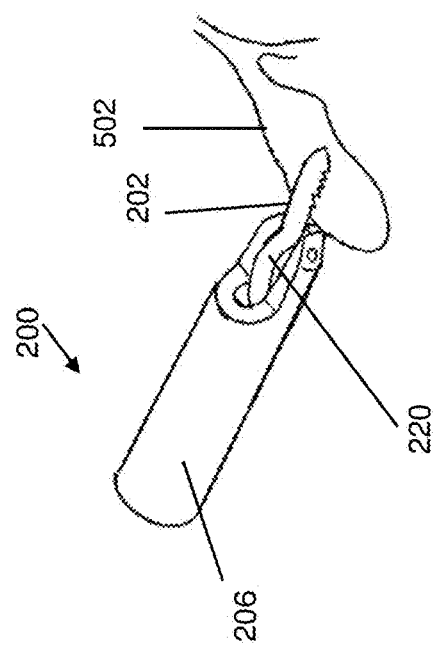
FIGS. 5A-5E depict illustrative variations of the methods described here.
Figure 5A:
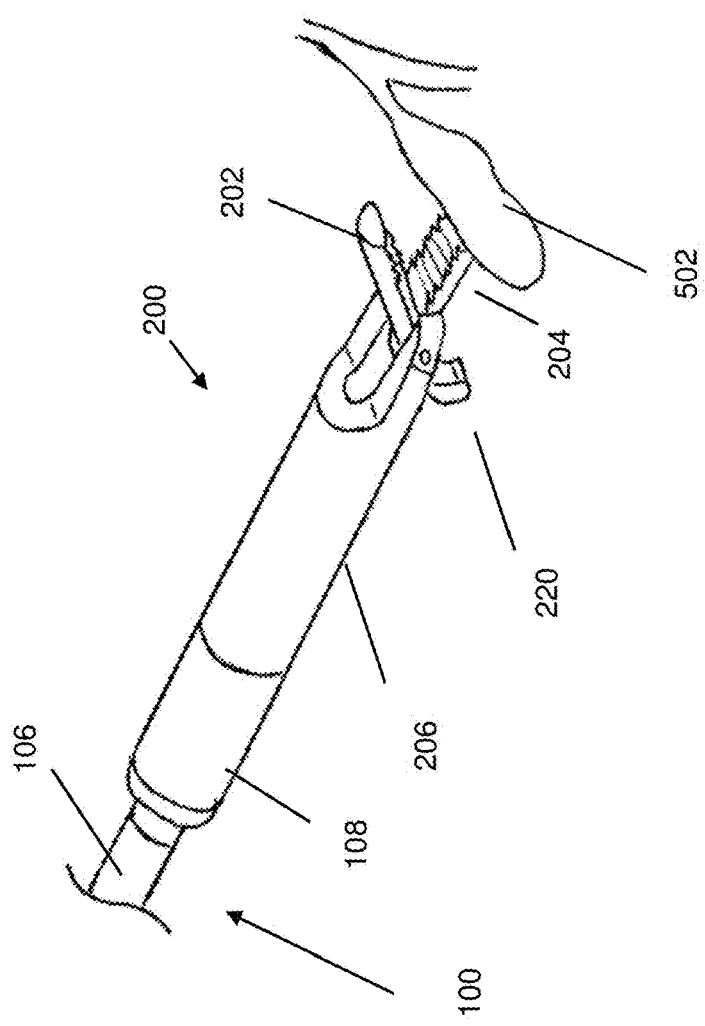

With the grasper releasably connected to the tissue (either by gripping the tissue or by capturing it in a space between the jaws), a control element comprising one or more magnetic elements, as described above, may be positioned externally of the body and may attract and/or repulse the grasper to reposition and/or hold the grasper. For example, FIGS. 5A-5D depict an illustrative method by which a grasper (200) may be used to reposition and/or hold tissue. While the variations of the grasper (200) and the delivery device (100) that are described above with respect to FIGS. 1A-1C and 2A-2F are depicted in FIGS. 5A-5D, it should be appreciated that any suitable graspers, and/or delivery systems as described here may perform the steps discussed below. Specifically, as shown in FIG. 5A, the grasper (200) may be advanced into the body toward a target tissue (502) (shown in FIG. 5 as a gallbladder, although it should be appreciated that the graspers described here may be releasably connected to any suitable tissue), and positioned in an open configuration. To advance the grasper (200), the grasper (200) may be releasably coupled to a distal engagement portion (108) of a delivery device (100), and a user may advance the distal engagement portion (108) into the body to position the grasper (200). The tissue (502) may be positioned between the first jaw (202) and second (204) jaw of the grasper (200), and the grasper (200) may be moved to a closed configuration to releasably couple the grasper (200) to the tissue (502), as shown in FIG. 5B. Once connected to the tissue (502), the grasper (200) may be released from the delivery device (100), and the delivery device (100) may be removed from the body.

Figure 5C:
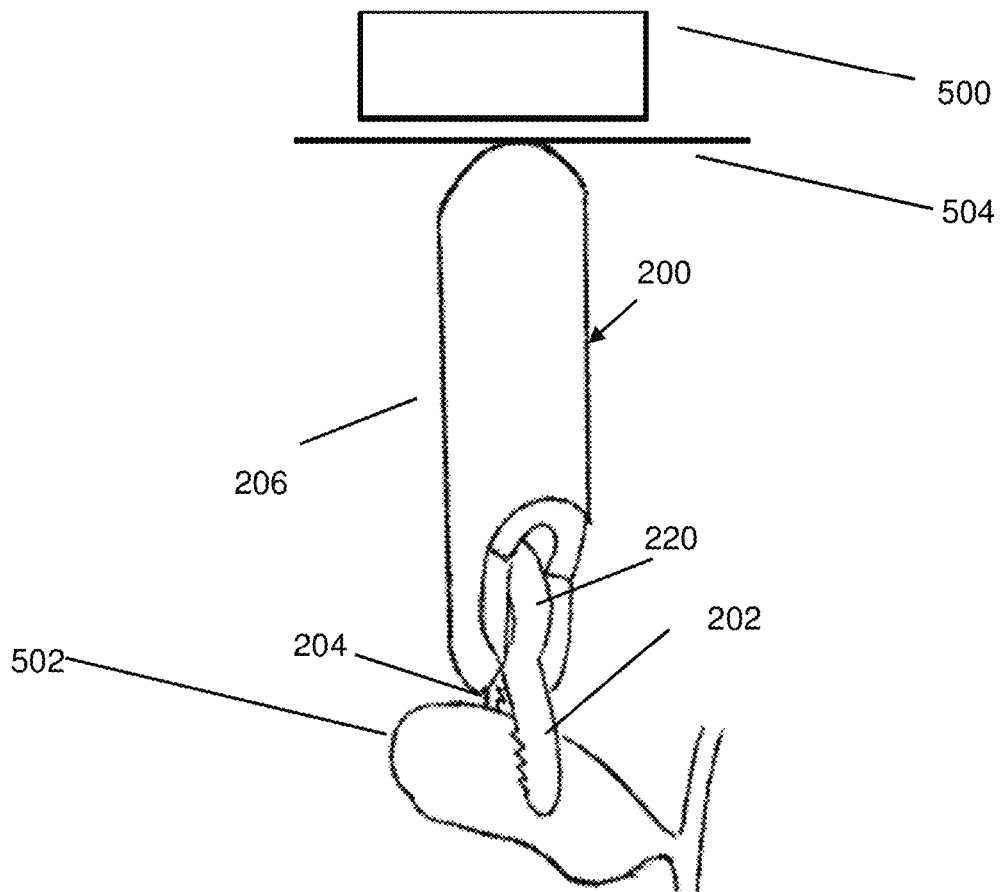

As described above with respect to FIGS. 8A-12C and shown in FIG. 5C, a control element (500) may be positioned externally of the body (e.g., cavity wall (504) and may attract the grasper (200) and lift the grasper toward the control element (500). When the grasper (200) is placed in the abdomen, this may lift the grasper toward the cavity wall (504). The control element (500) may be further manipulated (e.g., moved axially, laterally, and/or rotated) to reposition the grasper (200) and the tissue (502). In some variations, as shown in FIGS. 18A-18B, 19A-19B, and 20, a magnet of a control element may be manipulated (e.g., using a magnet control) to rotate and/or reposition the grasper and without moving the control element. For example, the grasper may be rotate in one or more of pitch, yaw, and roll through manipulation of the magnet relative to the control element.

Figure 5D:
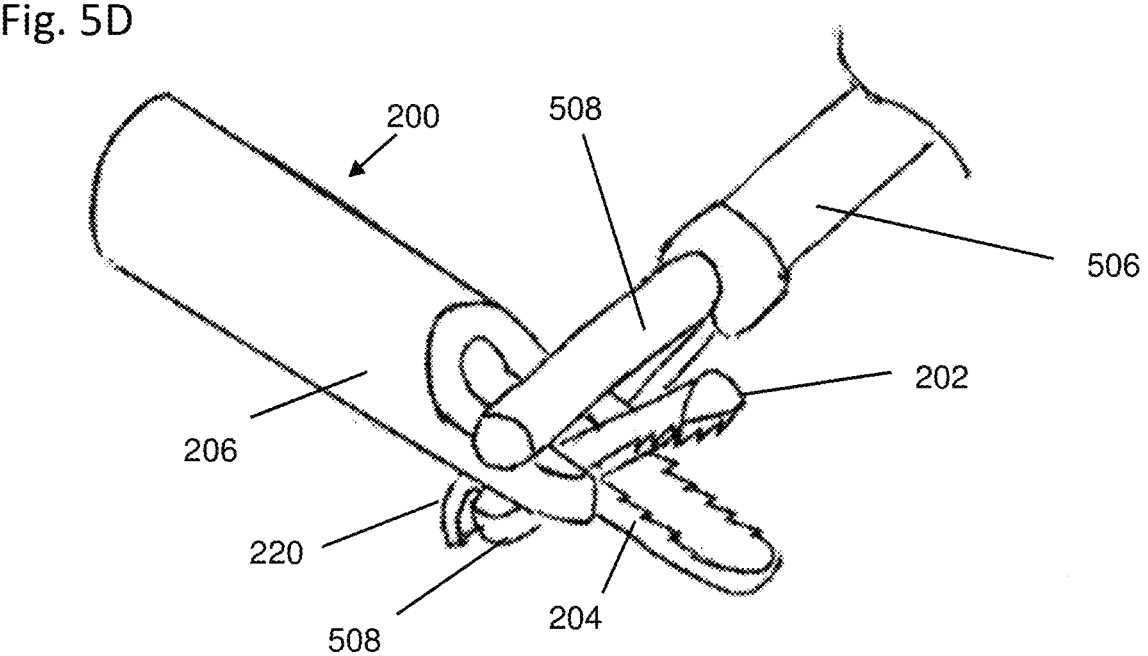

As mentioned above, in some instances it may be desirable to release the connection between the grasper (200) and the tissue (502). For example, in some instances it may be desirable to connect the grasper to a different portion of the tissue (502). In these instances, the grasper (200) may be returned to an open configuration (either using one of the delivery devices described here or a grasping device, as discussed above) to release the grasper (200) from the tissue (502). For example, FIG. 5D shows a grasping device (506) having opposing jaws (508) which may grab a proximal arm (220) and the main body (206) of the grasper (200) to rotate the first jaw (202) away from the second jaw (204), which may release the tissue (502) from the grasper (200). The grasper (200) may be repositioned to again place the tissue (502) between the jaws (202, 204) of the grasper (200), and the grasper (200) may then be placed in the closed configuration to reconnect the grasper (200) to the tissue (502). In some variations, the grasper may release the tissue, be repositioned at a second tissue, and may then be placed in the closed configuration to connect to the second tissue. In other instances, the grasper (200) may be decoupled from the tissue, and removed from the body.

Figure 5E:
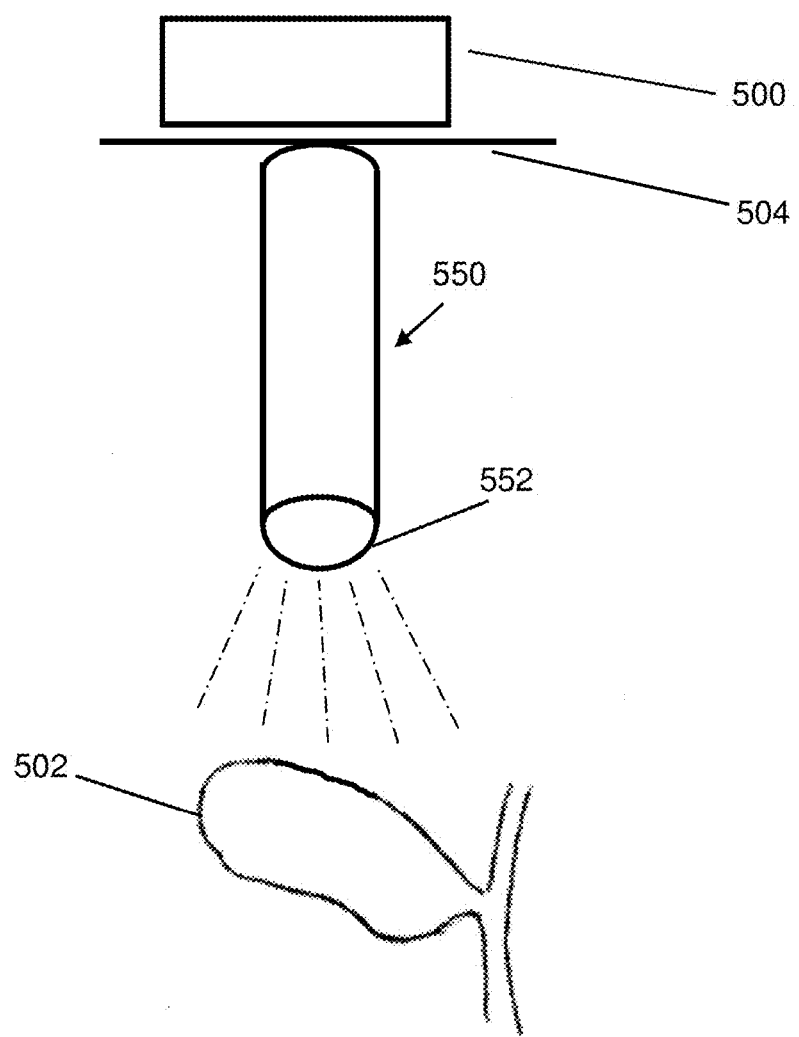

In some variations, a visualization device comprising a camera (550) may be advanced into the body with a lens (552) directed towards a target tissue (502) (shown in FIG. 5E as a gallbladder, although it should be appreciated that the cameras described here may image any tissue). To advance the camera (550), the camera (550) may be releasably coupled to a distal engagement portion of a delivery device, and a user may advance the distal engagement portion into the body to position the camera (550). Once in position, the camera (550) may be released from the delivery device, and the delivery device may be removed from the body.

As shown in FIG. 5E, a control element (500) may be positioned externally of the body (e.g., cavity wall (504)) and may attract the camera (550) and lift the camera (550) toward the control element (500). When the camera (550) is placed in the abdomen, this may lift the camera (550) toward the cavity wall (504). The control element (500) may be further manipulated (e.g., moved axially, laterally, and/or rotated) to reposition the camera (550). In some variations, as shown in FIGS. 18C-18D and 20, a magnet of a control element may be manipulated (e.g., using a magnet control) to rotate and/or reposition the camera (550) without moving the control element. For example, the camera (550) may be rotated in one or more of pitch, yaw, and roll through manipulation of the magnet relative to the control element.

Some methods may involve the delivery of two or more graspers as described herein. For example, a first grasper may be advanced into the body through a port using a delivery device, releasably connected to tissue (either by gripping the tissue or by capturing it in a space between the jaws), and released from the delivery device. A first control element may then be positioned externally of the body to attract and lift the first grasper toward the first control element. A second grasper may be advanced into the body through the same port (or a second port) using the same delivery device (or a second delivery device), releasably connected to tissue (either by gripping the tissue or by capturing it in a space between the jaws), and released from the delivery device. A second control element may then be positioned externally to the body to attract and lift the second grasper toward the second control element.

Figure 17:
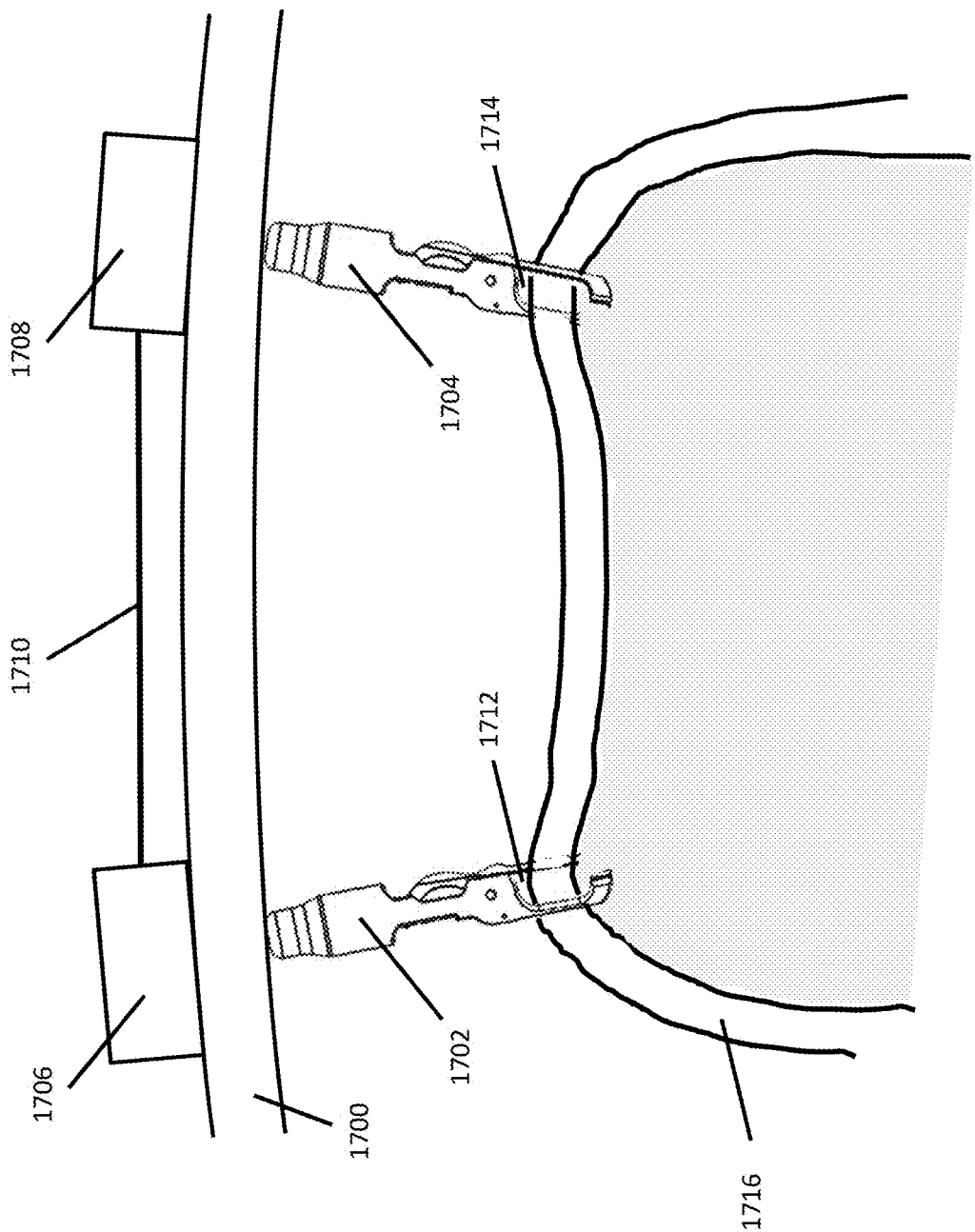
FIG. 17 depicts a side view of an illustrative variation of two graspers in use with two control elements.

It may in some variations be desirable to have a linkage connected to both the first and second control elements to prevent the magnetic fields generated by the control elements from affecting their relative positions. FIG. 17, illustrates an exemplary resulting configuration, with a first grasper (1702) positioned approximately perpendicular to an abdominal wall (1700) and attracted by a first control element (1706), and a second grasper (1704) positioned approximately perpendicular to the abdominal wall and attracted by a second control element (1708), with the first and second control elements (1706, 1708) connected by a linkage (1710). The first and second graspers (1702, 1704) may each hold tissue within a respective space (1712, 1714) between the two jaws of the graspers. As shown, the graspers (1702, 1704) may each hold different portions of the same tissue (1716) (e.g., colon), although it should be appreciated that the graspers (1702, 1704) may hold distinct pieces of tissue. Similarly, more than two graspers may be used in the same procedure, such as but not limited to three, four, five, or six graspers, or more. In some variations, the methods may comprise delivery of one or more graspers in combination with one or more additional instruments (e.g., one or more visualization devices such as camera and/or light source), delivery of two or more visualization devices, or the like. For example, in combination with advancement of a first grasper as described above, a camera may be advanced into the body through a port using a delivery device and released from the delivery device. A control element may then be positioned externally of the body to attract and lift the camera toward the first control element.

While the inventive devices, systems, and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims.

We claim:

1. A method for performing a surgical procedure, comprising:
grasping tissue in a grasper;
magnetically repulsing the grasper away from a control element across an abdominal wall;
repositioning the grasped tissue by manipulating a magnetic element of the control element; and
magnetically attracting a proximal end of the grasper to the control element across the abdominal wall and magnetically repulsing a distal end of the grasper away from the control element across the abdominal wall.

2. The method of claim 1, further comprising:
advancing the grasper into a body cavity using a delivery device; and
disconnecting the delivery device from the grasper.

3. The method of claim 2, wherein the grasper is advanced into the body cavity prior to magnetically repulsing the grasper.

4. The method of claim 1, wherein magnetically repulsing the grasper comprises magnetically repulsing a proximal end of the grasper away from the control element across an abdominal wall.

5. The method of claim 1, wherein magnetically repulsing the grasper comprises magnetically repulsing the grasper after grasping the tissue in the grasper.

6. The method of claim 1, wherein the grasper comprises a magnetic element having a pole orientation substantially perpendicular to a longitudinal axis of the grasper.

7. The method of claim 1, wherein magnetically repulsing the grasper comprises manipulating the control element.

8. The method of claim 1, wherein the grasper comprises a magnetic element having a pole orientation substantially parallel to a longitudinal axis of the grasper.

9. The method of claim 1, wherein magnetically repulsing the grasper comprises yawing the grasper about a yaw axis perpendicular to a longitudinal axis of the grasper.

10. The method of claim 1, wherein magnetically repulsing the grasper comprises rolling the grasper about a longitudinal axis of the grasper.

11. The method of claim 1, wherein the grasper comprises a main body, a first jaw, and a second jaw, and comprises a closed configuration and an open configuration, wherein in the closed configuration, the first jaw and the second jaw form a space configured to hold tissue.

12. The method of claim 11, wherein magnetically repulsing the grasper comprises magnetically repulsing the first and second jaws away from the control element across an abdominal wall.

13. The method of claim 1, wherein manipulating the magnetic element of the control element comprises rotating the magnetic element relative to the control element.

14. The method of claim 13, wherein the control element remains stationary relative to the abdominal wall while rotating the magnetic element.

15. The method of claim 1, further comprising aligning a longitudinal axis of the grasper substantially transverse to a longitudinal axis of the control element by rotating the magnetic element relative to the control element.

16. The method of claim 1, further comprising aligning a longitudinal axis of the grasper substantially parallel to a longitudinal axis of the control element by rotating the magnetic element relative to the control element.

17. A method for performing a surgical procedure, comprising:
grasping tissue in a grasper;
magnetically repulsing the grasper away from a control element across an abdominal wall;
repositioning the grasped tissue by manipulating a magnetic element of the control element, wherein a proximal end of the grasper comprises a first magnetic portion and a distal end of the grasper comprises a second magnetic portion, wherein the first magnetic portion has a first polarity and the second magnetic portion has a second polarity opposite the first polarity; and magnetically attracting the first magnetic portion to the control element across the abdominal wall and magnetically repulsing the second magnetic portion away from the control element across the abdominal wall.

18. The method of claim 17, further comprising:

advancing the grasper into a body cavity using a delivery device; and disconnecting the delivery device from the grasper.

19. The method of claim 18, wherein the grasper is advanced into the body cavity prior to magnetically repulsing the grasper.

* * * * *